United States Patent
Jensen

(10) Patent No.: US 10,829,556 B2
(45) Date of Patent: Nov. 10, 2020

(54) POLYNUCLEOTIDES ENCODING BISPECIFIC CHIMERIC ANTIGEN RECEPTORS

(71) Applicant: Seattle Children's Hospital, Seattle, WA (US)

(72) Inventor: Michael Jensen, Bainbridge, WA (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 0 days.

(21) Appl. No.: 16/240,652

(22) Filed: Jan. 4, 2019

(65) Prior Publication Data

US 2019/0119382 A1     Apr. 25, 2019

Related U.S. Application Data

(60) Division of application No. 15/233,140, filed on Aug. 10, 2016, now Pat. No. 10,189,903, which is a continuation of application No. 14/376,610, filed as application No. PCT/US2013/025953 on Feb. 13, 2013, now Pat. No. 9,447,194.

(60) Provisional application No. 61/598,216, filed on Feb. 13, 2012.

(51) Int. Cl.

| | |
|---|---|
| *C12N 5/0783* | (2010.01) |
| *C12N 7/00* | (2006.01) |
| *C07K 16/28* | (2006.01) |
| *A61K 47/68* | (2017.01) |
| *C07K 16/46* | (2006.01) |
| *A61K 38/17* | (2006.01) |
| *A61K 35/17* | (2015.01) |
| *C07K 14/725* | (2006.01) |
| *C07K 14/705* | (2006.01) |
| *C07K 14/71* | (2006.01) |
| *A61K 38/00* | (2006.01) |
| *A61K 39/00* | (2006.01) |

(52) U.S. Cl.
CPC .......... *C07K 16/2803* (2013.01); *A61K 35/17* (2013.01); *A61K 38/179* (2013.01); *A61K 47/6849* (2017.08); *C07K 14/7051* (2013.01); *C07K 14/70517* (2013.01); *C07K 14/70521* (2013.01); *C07K 14/70578* (2013.01); *C07K 14/71* (2013.01); *C07K 16/2887* (2013.01); *C07K 16/2896* (2013.01); *C07K 16/468* (2013.01); *C12N 5/0636* (2013.01); *C12N 7/00* (2013.01); *A61K 38/00* (2013.01); *A61K 2039/505* (2013.01); *C07K 2317/24* (2013.01); *C07K 2317/31* (2013.01); *C07K 2317/56* (2013.01); *C07K 2317/622* (2013.01); *C07K 2319/03* (2013.01); *C07K 2319/74* (2013.01); *C12N 2510/00* (2013.01); *C12N 2740/15021* (2013.01); *C12N 2740/15043* (2013.01); *Y02A 50/473* (2018.01)

(58) Field of Classification Search
CPC ............ C07K 16/2803; C07K 16/2887; C07K 16/2896; C07K 16/468; C07K 14/7051; C07K 14/70517; C07K 14/70521; C07K 14/70578; C07K 14/71; C07K 14/21; C07K 2319/03; C07K 2319/74; C07K 2317/24; C07K 2317/31; C07K 2317/56; C07K 2317/622; C12N 7/00; C12N 5/0636; C12N 2740/15021; C12N 2740/15043; C12N 2510/00; A61K 35/17; A61K 47/6849; A61K 38/00; A61K 38/179; A61K 2039/505; Y02A 50/473; A61P 35/00

See application file for complete search history.

(56) References Cited

U.S. PATENT DOCUMENTS

| | | |
|---|---|---|
| 5,741,899 A | 4/1998 | Capon et al. |
| 6,103,521 A | 8/2000 | Capon et al. |
| 9,447,194 B2 | 9/2016 | Jensen et al. |
| 10,189,903 B2 | 1/2019 | Jensen |
| 2003/0077249 A1 | 4/2003 | Bebbington et al. |
| 2005/0113564 A1 | 5/2005 | Campana et al. |
| 2010/0135974 A1 | 6/2010 | Eshhar et al. |
| 2010/0189690 A1 | 7/2010 | Buchholz et al. |
| 2010/0323420 A1 | 12/2010 | Crabtree et al. |
| 2011/0044986 A1 | 2/2011 | Biere-Citron et al. |
| 2011/0135657 A1 | 6/2011 | Hu et al. |

(Continued)

FOREIGN PATENT DOCUMENTS

| | | |
|---|---|---|
| AU | 2013221672 | 8/2014 |
| CA | 2861491 | 8/2013 |

(Continued)

OTHER PUBLICATIONS

Lum LG and Thakur A (Dec. 1, 2011) BioDrugs. 25(6):365-379. (doi:10.2165/11595950-000000000-00000).*
Otz T (2009) Leukemia. 23:71-77. (doi:10.1038/leu.2008.271).*
Patel et al., T-Cell Killing of Heterogenous Tumor or Viral Targets with Bispecific Chimeric Immune Receptors, 2000, Cancer Gene Therapy, vol. 7(8), pp. 1127-1134.

(Continued)

*Primary Examiner* — Robert S Landsman
(74) *Attorney, Agent, or Firm* — Nixon Peabody LLP

(57) ABSTRACT

The invention is directed to a bispecific chimeric antigen receptor, comprising: (a) at least two antigen-specific targeting regions; (b) an extracellular spacer domain; (c) a transmembrane domain; (d) at least one co-stimulatory domain; and (e) an intracellular signaling domain, wherein each antigen-specific targeting region comprises an antigen-specific single chain Fv (scFv) fragment, and binds a different antigen, and wherein the bispecific chimeric antigen receptor is co-expressed with a therapeutic control. The invention also provides methods and uses of the bispecific chimeric antigen receptors.

22 Claims, 22 Drawing Sheets

Specification includes a Sequence Listing.

(56) References Cited

U.S. PATENT DOCUMENTS

2011/0223129 A1 9/2011 Jensen
2013/0280220 A1 10/2013 Ahmed et al.

FOREIGN PATENT DOCUMENTS

| EP | 2814846 A1 | 12/2014 |
| EP | 3594245 A1 | 1/2020 |
| HK | 1205144 A1 | 12/2015 |
| JP | 2010502232 A | 1/2010 |
| JP | 2010530737 A | 9/2010 |
| JP | 2011523400 A | 8/2011 |
| JP | 2015513394 A1 | 5/2015 |
| JP | 201955330 A | 6/2019 |
| WO | 2011041093 A1 | 4/2011 |
| WO | 2011056894 | 5/2011 |
| WO | 2013123061 | 8/2013 |

OTHER PUBLICATIONS

Cartellieri et al. Chimeric antigen receptor-engineered T cells for immunotherapy of cancer. J Biomed Biotechnol (2010). 13 pages.
Casucci et al. Suicide Gene Therapy to Increase the Safety of Chimeric Antigen Receptor-Redirected T Lymphocytes. Journal of Cancer (2011). 2:378-382.
Choi et al. Bispecific antibodies engage T cells for antitumor immunotherapy. Expert Opin Biol Ther (2011). 11(7):843-853.
Curran et al. Chimeric antigen receptor for T cell immunotherapy: current understanding and future directions. J Gene Med (2010). 14:405-415.
Grada et al., Targeting the Tumor Heterogeneity in Glioblastoma: A Chimeric Antigen Receptor Molecule Mediates Bispecific Activation and Targeting of T Lymphocytes, Neuro-Oncology, 2011, vol. 13, Supplemental 3, p. iii.115.
Grada et al., A Chimeric Antigen Receptor Molecule Mediates Bispecific Activation and Targeting of T Lymphocytes, Molecular Therapy, 2011, vol. 19, Supplement 2. p. S11.
Jena et al. Redirecting T-cell specificity by introducing a tumor-specific chimeric antigen receptor. Blood (2010). 116(7):1035-1044.
Jensen et al. Antitransgene rejection responses contribute to attenuated persistence of adoptively transferred CD20/CD19-specific chimeric antigen receptor redirected T cells in humans. Biol Blood Marrow Transplant (2010). 16:1245-1256.
Urbanska et al. Targeted cancer immunotherapy via combination of designer bispecific antibody and novel gene-engineered T cells. J Transl Med (2010). 12:347; 12 pages.
Wang et al. A transgene-encoded cell surface polypeptide for selection, in vivo tracking, and ablation of engineered cells. Blood (2011). 118(5):1255-1263.
International Search Report and Written Opinion for PCT/US2013/25953 dated May 21, 2013, 16 pages.
International Preliminary Report on Patentability for PCT/US2013/25953 dated Aug. 19, 2014, 13 pages.
Extended Search Report for European Patent Application No. 13748596.7 dated Oct. 2, 2015, 10 pages.
EP 19173955.6 Extended Search Report dated Dec. 17, 2019, 13 pages.
Grada et al., TanCAR: A Novel Bispecific Chimeric Antigen Receptor for Cancer Immunotherapy, Molecular-Therapy-Nucleic Acids, 2013, vol. 2, pp. 1-11.
Hudecek et al., Naïve CD4+ T Cells Modified to Express a ROR1-Specific CAR Mediate Anti-Tumor Activity and Provide Superior Help to CD8+ ROR1-CAR T Cells, Blood, 2011, vol. 118(21), Abstract No. 643.
Park et al., Adoptive Immunotherapy for B-Cell Malignancies with Autologous Chimeric Antigen Receptor Modified Tumor Targeted T-Cells, Discov Med, 2010, vol. 9(47), pp. 277-288.

* cited by examiner

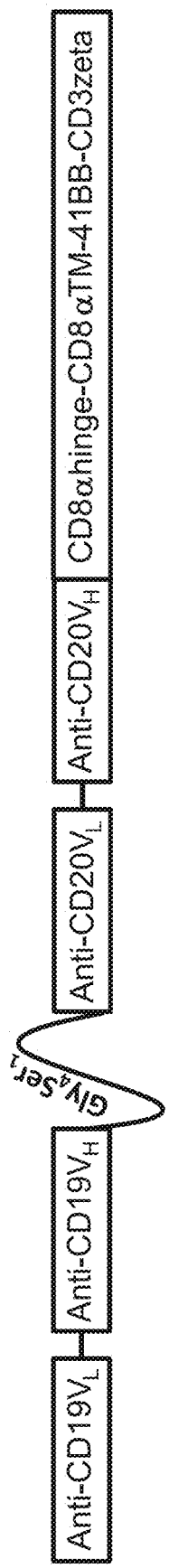

FIG. 3

GMCSFRs.s CD19scFv-Gly4Ser1linker-CD20scFv-IgG4Hinge-CD28tm-41BB-CD3zeta-T2A-EGFRt_epHIV7 atgctgctgctggtgaccagcctgctgctgtgcgagctgccccaccccgcctttctgctgatccccatgacccagaccacctccagcctgagcgccagc
ctgggcgaccgggtgaccatcagctgccgggccagccaggacatcagcaagtacctgaactggtatcagcagaagcccgacggcaccgtcaagctg
ctgatctaccacaccagccggctgcacagcggcgtgcccagccggtttagcggcagcggctccggcaccgactacagcctgaccatctccaacctgga
acaggaagatatcgccacctacttttgccagcagggcaacacactgcccacccttggcggcgggaacaaagctggaaatcaccggcagcacctcc
ggcagcggcaagcctggcagcggcgagggcagcaccaagggcgaggtgaagctgcaggaaagcggccctggcctggtggccccagccagagcct
gagcgtgacctgcaccgtgagcggcgtgagcctgcccgactacggcgtgagctggatccggcagccccccaggaagggcctggaatggctgggcgt
gatctggggcagcgagaccacctactacaacagcgccctgaagagccggctgaccatcatcaaggacaacagcaagagccaggtgttcctgaagat
gaacagcctgcagaccgacgacaccgccatctactactgcgccaagcactactactacggcggcagctacgccatggactactggggccagggcacc
agcgtgaccgtgagcagcggaggtggtggatccgaggtgcagctgcagcagtcgggggctgagctggtgaagcctggggcctcagtgaagatgtcct
gcaaggcttctggctacacatttaccagttacaatatgcactgggtaaagcagacacctggacagggcctggaatggattggagctatttatccagga
aatggtgatacttcctacaatcagaagttcaaaggcaaggccacattgactgcagacaaatcctccagcacagcctacatgcagctcagcagcctga
catctgaggactctgcggactattactgtgcaagatctaattattacggtagtagctactggttcttcgatgtctggggcgcagggaccacggtcaccgt
ctcctcaggcagtactagcggtggtggctccggggggcggttccggtgggggcggcagcagcgacattgtgctgacccaatctccagctatcctgtctgc
atctccaggggagaaggtcacaatgacttgcagggccagctcaagtgtaaattacatggactggtaccagaagaagccaggatcctcccccaaaccc
tggatttatgccacatccaacctggcttctggagtccctgctcgcttcagtggcagtgggtctgggacctcttactctctcacaatcagcagagtggagg
ctgaagatgctgccacttattactgccagcagtggagttttaatccacccacgttcggaggggggaccaagctggaaataaaagagagcaagtacgg
accgccctgccccccttgccctatgttctgggtgctggtggtggtcggaggcgtgctggcctgctacagcctgctggtcaccgtggccttcatcatcttttg
ggtgaaacggggcagaaagaaactcctgtatatattcaaacaaccatttatgagaccagtacaaactactcaagaggaagatggctgtagctgccga
tttccagaagaagaagaaggaggatgtgaactgcgggtgaagttcagcagaagcgccgacgcccctgcctaccagcagggccagaatcagctgtac
aacgagctgaacctgggcagaagggaagagtacgacgtcctggataagcggagaggccgggaccctgagatgggcggcaagcctcggcggaaga
accccaggaaggcctgtataacgaactgcagaaagacaagatggccgaggcctacagcgagatcggcatgaaggcgagcggaggcggggcaa
gggccacgacggcctgtatcagggcctgtccaccgccaccaaggatacctacgacgccctgcacatgcaggccctgcccccaaggctcgagggcggc
ggagagggcagaggaagtcttctaacatgcggtgacgtggaggagaatcccggccctaggatgcttctcctggtgacaagccttctgctctgtgagtt
accacacccagcattcctcctgatcccacgcaaagtgtgtaacggaataggtattggtgaatttaaagactcactctccataaatgctacgaatattaa
acacttcaaaaactgcacctccatcagtggcgatctccacatcctgccggtggcatttagggggtgactccttcacacatactcctcctctggatccacag
gaactggatattctgaaaaccgtaaaggaaatcacaggttttgctgattcaggcttggcctgaaaacaggacggacctccatgcctttgagaacct
agaaatcatacgcggcaggaccaagcaacatggtcagttttctcttgcagtcgtcagcctgaacataacatccttgggattacgctccctcaaggagat
aagtgatggagatgtgataatttcaggaaacaaaaatttgtgctatgcaaatacaataaactggaaaaaactgtttgggacctccggtcagaaaacc
aaaattataagcaacagaggtgaaaacagctgcaaggccacaggccaggtctgccatgccttgtgctcccccgagggctgctggggcccggagccc
agggactgcgtctcttgccggaatgtcagccgaggcagggaatgcgtggacaagtgcaaccttctggagggtgagccaagggagtttgtggagaact
ctgagtgcatacagtgccacccagagtgcctgcctcaggccatgaacatcacctgcacaggacggggaccagacaactgtatccagtgtgcccacta
cattgacggcccccactgcgtcaagacctgcccggcaggagtcatgggagaaaacaacaccctggtctggaagtacgcagacgccgccatgtgtgc
cacctgtgccatccaaactgcacctacggatgcactgggccaggtcttgaaggctgtccaacgaatgggcctaagatcccgtccatcgccactgggat
ggtgggggcccctcctcttgctgctggtggtggccctggggatcggcctcttcatgtga

FIG. 4

GMCSFRs.s CD19scFv-Gly4Ser1linker-CD20scFv-IgG4Hinge-CD28tm-41BB-CD3zeta-T2A-EGFRt_epHIV7

```
DNA: ATGCTGCTGCTGGTGACCAGCCTGCTGCTGTGCGAGCTGCCCCACCCCGCC
 AA: M   L   L   L   V   T   S   L   L   L   C   E   L   P   H   P   A
DNA: TTTCTGCTGATCCCCATGACCCAGACCACCTCCAGCCTGAGCGCCAGCCTG
 AA: F   L   L   I   P   M   T   Q   T   T   S   S   L   S   A   S   L
DNA: GGCGACCGGGTGACCATCAGCTGCCGGGCCAGCCAGGACATCAGCAAGTAC
 AA: G   D   R   V   T   I   S   C   R   A   S   Q   D   I   S   K   Y
DNA: CTGAACTGGTATCAGCAGAAGCCCGACGGCACCGTCAAGCTGCTGATCTAC
 AA: L   N   W   Y   Q   Q   K   P   D   G   T   V   K   L   L   I   Y
DNA: CACACCAGCCGGCTGCACAGCGGCGTGCCCAGCCGGTTTAGCGGCAGCGGC
 AA: H   T   S   R   L   H   S   G   V   P   S   R   F   S   G   S   G
DNA: TCCGGCACCGACTACAGCCTGACCATCTCCAACCTGGAACAGGAAGATATC
 AA: S   G   T   D   Y   S   L   T   I   S   N   L   E   Q   E   D   I
DNA: GCCACCTACTTTTGCCAGCAGGGCAACACACTGCCCTACACCTTTGGCGGC
 AA: A   T   Y   F   C   Q   Q   G   N   T   L   P   Y   T   F   G   G
DNA: GGAACAAAGCTGGAAATCACCGGCAGCACCTCCGGCAGCGGCAAGCCTGGC
 AA: G   T   K   L   E   I   T   G   S   T   S   G   S   G   K   P   G
DNA: AGCGGCGAGGGCAGCACCAAGGGCGAGGTGAAGCTGCAGGAAAGCGGCCCT
 AA: S   G   E   G   S   T   K   G   E   V   K   L   Q   E   S   G   P
DNA: GGCCTGGTGGCCCCCAGCCAGAGCCTGAGCGTGACCTGCACCGTGAGCGGC
 AA: G   L   V   A   P   S   Q   S   L   S   V   T   C   T   V   S   G
DNA: GTGAGCCTGCCCGACTACGGCGTGAGCTGGATCCGGCAGCCCCCCAGGAAG
 AA: V   S   L   P   D   Y   G   V   S   W   I   R   Q   P   P   R   K
DNA: GGCCTGGAATGGCTGGGCGTGATCTGGGGCAGCGAGACCACCTACTACAAC
 AA: G   L   E   W   L   G   V   I   W   G   S   E   T   T   Y   Y   N
DNA: AGCGCCCTGAAGAGCCGGCTGACCATCATCAAGGACAACAGCAAGAGCCAG
 AA: S   A   L   K   S   R   L   T   I   I   K   D   N   S   K   S   Q
DNA: GTGTTCCTGAAGATGAACAGCCTGCAGACCGACGACACCGCCATCTACTAC
 AA: V   F   L   K   M   N   S   L   Q   T   D   D   T   A   I   Y   Y
DNA: TGCGCCAAGCACTACTACTACGGCGGCAGCTACGCCATGGACTACTGGGGC
 AA: C   A   K   H   Y   Y   Y   G   G   S   Y   A   M   D   Y   W   G
DNA: CAGGGCACCAGCGTGACCGTGAGCAGCGGAGGTGGTGGATCCGAGGTGCAG
 AA: Q   G   T   S   V   T   V   S   S   G   G   G   G   S   E   V   Q
DNA: CTGCAGCAGTCTGGGGCTGAGCTGGTGAAGCCTGGGGCCTCAGTGAAGATG
 AA: L   Q   Q   S   G   A   E   L   V   K   P   G   A   S   V   K   M
DNA: TCCTGCAAGGCTTCTGGCTACACATTTACCAGTTACAATATGCACTGGGTA
 AA: S   C   K   A   S   G   Y   T   F   T   S   Y   N   M   H   W   V
DNA: AAGCAGACACCTGGACAGGGCCTGGAATGGATTGGAGCTATTTATCCAGGA
 AA: K   Q   T   P   G   Q   G   L   E   W   I   G   A   I   Y   P   G
DNA: AATGGTGATACTTCCTACAATCAGAAGTTCAAAGGCAAGGCCACATTGACT
 AA: N   G   D   T   S   Y   N   Q   K   F   K   G   K   A   T   L   T
DNA: GCAGACAAATCCTCCAGCACAGCCTACATGCAGCTCAGCAGCCTGACATCT
 AA: A   D   K   S   S   S   T   A   Y   M   Q   L   S   S   L   T   S
DNA: GAGGACTCTGCGGACTATTACTGTGCAAGATCTAATTATTACGGTAGTAGC
 AA: E   D   S   A   D   Y   Y   C   A   R   S   N   Y   Y   G   S   S
DNA: TACTGGTTCTTCGATGTCTGGGGCGCAGGGACCACGGTCACCGTCTCCTCA
 AA: Y   W   F   F   D   V   W   G   A   G   T   T   V   T   V   S   S
DNA: GGCAGTACTAGCGGTGGTGGCTCCGGGGGCGGTTCCGGTGGGGCGGCAGC
 AA: G   S   T   S   G   G   G   S   G   G   G   S   G   G   G   S
DNA: AGCGACATTGTGCTGACCCAATCTCCAGCTATCCTGTCTGCATCTCCAGGG
 AA: S   D   I   V   L   T   Q   S   P   A   I   L   S   A   S   P   G
DNA: GAGAAGGTCACAATGACTTGCAGGGCCAGCTCAAGTGTAAATTACATGGAC
 AA: E   K   V   T   M   T   C   R   A   S   S   S   V   N   Y   M   D
```

FIG. 4 continued

```
DNA: TGGTACCAGAAGAAGCCAGGATCCTCCCCCAAACCCTGGATTTATGCCACA
 AA:  W  Y  Q  K  K  P  G  S  S  P  K  P  W  I  Y  A  T
DNA: TCCAACCTGGCTTCTGGAGTCCCTGCTCGCTTCAGTGGCAGTGGGTCTGGG
 AA:  S  N  L  A  S  G  V  P  A  R  F  S  G  S  G  S  G
DNA: ACCTCTTACTCTCTCACAATCAGCAGAGTGGAGGCTGAAGATGCTGCCACT
 AA:  T  S  Y  S  L  T  I  S  R  V  E  A  E  D  A  A  T
DNA: TATTACTGCCAGCAGTGGAGTTTTAATCCACCCACGTTCGGAGGGGGGACC
 AA:  Y  Y  C  Q  Q  W  S  F  N  P  P  T  F  G  G  G  T
DNA: AAGCTGGAAATAAAAGAGAGCAAGTACGGACCGCCCTGCCCCCCTTGCCCT
 AA:  K  L  E  I  K  E  S  K  Y  G  P  P  C  P  P  C  P
DNA: ATGTTCTGGGTGCTGGTGGTGGTCGGAGGCGTGCTGGCCTGCTACAGCCTG
 AA:  M  F  W  V  L  V  V  V  G  G  V  L  A  C  Y  S  L
DNA: CTGGTCACCGTGGCCTTCATCATCTTTTGGGTGAAACGGGGCAGAAAGAAA
 AA:  L  V  T  V  A  F  I  I  F  W  V  K  R  G  R  K  K
DNA: CTCCTGTATATATTCAAACAACCATTTATGAGACCAGTACAAACTACTCAA
 AA:  L  L  Y  I  F  K  Q  P  F  M  R  P  V  Q  T  T  Q
DNA: GAGGAAGATGGCTGTAGCTGCCGATTTCCAGAAGAAGAAGAAGGAGGATGT
 AA:  E  E  D  G  C  S  C  R  F  P  E  E  E  E  G  G  C
DNA: GAACTGCGGGTGAAGTTCAGCAGAAGCGCCGACGCCCCTGCCTACCAGCAG
 AA:  E  L  R  V  K  F  S  R  S  A  D  A  P  A  Y  Q  Q
DNA: GGCCAGAATCAGCTGTACAACGAGCTGAACCTGGGCAGAAGGGAAGAGTAC
 AA:  G  Q  N  Q  L  Y  N  E  L  N  L  G  R  R  E  E  Y
DNA: GACGTCCTGGATAAGCGGAGAGGCCGGGACCCTGAGATGGGCGGCAAGCCT
 AA:  D  V  L  D  K  R  R  G  R  D  P  E  M  G  G  K  P
DNA: CGGCGGAAGAACCCCCAGGAAGGCCTGTATAACGAACTGCAGAAAGACAAG
 AA:  R  R  K  N  P  Q  E  G  L  Y  N  E  L  Q  K  D  K
DNA: ATGGCCGAGGCCTACAGCGAGATCGGCATGAAGGGCGAGCGGAGGCGGGGC
 AA:  M  A  E  A  Y  S  E  I  G  M  K  G  E  R  R  R  G
DNA: AAGGGCCACGACGGCCTGTATCAGGGCCTGTCCACCGCCACCAAGGATACC
 AA:  K  G  H  D  G  L  Y  Q  G  L  S  T  A  T  K  D  T
DNA: TACGACGCCCTGCACATGCAGGCCCTGCCCCAAGGCTCGAGGGCGGCGGA
 AA:  Y  D  A  L  H  M  Q  A  L  P  P  R  L  E  G  G  G
DNA: GAGGGCAGAGGAAGTCTTCTAACATGCGGTGACGTGGAGGAGAATCCCGGC
 AA:  E  G  R  G  S  L  L  T  C  G  D  V  E  E  N  P  G
DNA: CCTAGGATGCTTCTCCTGGTGACAAGCCTTCTGCTCTGTGAGTTACCACAC
 AA:  P  R  M  L  L  L  V  T  S  L  L  L  C  E  L  P  H
DNA: CCAGCATTCCTCCTGATCCCACGCAAAGTGTGTAACGGAATAGGTATTGGT
 AA:  P  A  F  L  L  I  P  R  K  V  C  N  G  I  G  I  G
DNA: GAATTTAAAGACTCACTCTCCATAAATGCTACGAATATTAAACACTTCAAA
 AA:  E  F  K  D  S  L  S  I  N  A  T  N  I  K  H  F  K
DNA: AACTGCACCTCCATCAGTGGCGATCTCCACATCCTGCCGGTGGCATTTAGG
 AA:  N  C  T  S  I  S  G  D  L  H  I  L  P  V  A  F  R
DNA: GGTGACTCCTTCACACATACTCCTCCTCTGGATCCACAGGAACTGGATATT
 AA:  G  D  S  F  T  H  T  P  P  L  D  P  Q  E  L  D  I
DNA: CTGAAAACCGTAAAGGAAATCACAGGGTTTTTGCTGATTCAGGCTTGGCCT
 AA:  L  K  T  V  K  E  I  T  G  F  L  L  I  Q  A  W  P
DNA: GAAAACAGGACGGACCTCCATGCCTTTGAGAACCTAGAAATCATACGCGGC
 AA:  E  N  R  T  D  L  H  A  F  E  N  L  E  I  I  R  G
DNA: AGGACCAAGCAACATGGTCAGTTTTCTCTTGCAGTCGTCAGCCTGAACATA
 AA:  R  T  K  Q  H  G  Q  F  S  L  A  V  V  S  L  N  I
DNA: ACATCCTTGGGATTACGCTCCCTCAAGGAGATAAGTGATGGAGATGTGATA
 AA:  T  S  L  G  L  R  S  L  K  E  I  S  D  G  D  V  I
DNA: ATTTCAGGAAACAAAAATTTGTGCTATGCAAATACAATAAACTGGAAAAAA
 AA:  I  S  G  N  K  N  L  C  Y  A  N  T  I  N  W  K  K
DNA: CTGTTTGGGACCTCCGGTCAGAAAACCAAAATTATAAGCAACAGAGGTGAA
 AA:  L  F  G  T  S  G  Q  K  T  K  I  I  S  N  R  G  E
```

FIG. 4 continued

```
DNA: AACAGCTGCAAGGCCACAGGCCAGGTCTGCCATGCCTTGTGCTCCCCGAG
 AA: N   S   C   K   A   T   G   Q   V   C   H   A   L   C   S   P   E
DNA: GGCTGCTGGGGCCCGGAGCCCAGGGACTGCGTCTCTTGCCGGAATGTCAGC
 AA: G   C   W   G   P   E   P   R   D   C   V   S   C   R   N   V   S
DNA: CGAGGCAGGGAATGCGTGGACAAGTGCAACCTTCTGGAGGGTGAGCCAAGG
 AA: R   G   R   E   C   V   D   K   C   N   L   L   E   G   E   P   R
DNA: GAGTTTGTGGAGAACTCTGAGTGCATACAGTGCCACCCAGAGTGCCTGCCT
 AA: E   F   V   E   N   S   E   C   I   Q   C   H   P   E   C   L   P
DNA: CAGGCCATGAACATCACCTGCACAGGACGGGGACCAGACAACTGTATCCAG
 AA: Q   A   M   N   I   T   C   T   G   R   G   P   D   N   C   I   Q
DNA: TGTGCCCACTACATTGACGGCCCCCACTGCGTCAAGACCTGCCCGGCAGGA
 AA: C   A   H   Y   I   D   G   P   H   C   V   K   T   C   P   A   G
DNA: GTCATGGGAGAAAACAACACCCTGGTCTGGAAGTACGCAGACGCCGGCCAT
 AA: V   M   G   E   N   N   T   L   V   W   K   Y   A   D   A   G   H
DNA: GTGTGCCACCTGTGCCATCCAAACTGCACCTACGGATGCACTGGGCCAGGT
 AA: V   C   H   L   C   H   P   N   C   T   Y   G   C   T   G   P   G
DNA: CTTGAAGGCTGTCCAACGAATGGGCCTAAGATCCCGTCCATCGCCACTGGG
 AA: L   E   G   C   P   T   N   G   P   K   I   P   S   I   A   T   G
DNA: ATGGTGGGGGCCCTCCTCTTGCTGCTGGTGGTGGCCCTGGGGATCGGCCTC
 AA: M   V   G   A   L   L   L   L   L   V   V   A   L   G   I   G   L
DNA: TTCATGTGA
 AA: F   M   *
```

FIG. 7

IgG4hinge-CD28tm-41BB-CD3Zeta gagagcaagtacggaccgccctgccccccttgccctatgttctgggtgctggtggtggtcggaggcgtgctggcctgctacagc
ctgctggtcaccgtggccttcatcatcttttgggtgaaacggggcagaaagaaactcctgtatatattcaaacaaccatttatgaga
ccagtacaaactactcaagaggaagatggctgtagctgccgatttccagaagaagaagaaggaggatgtgaactgcgggtgaa
gttcagcagaagcgccgacgcccctgcctaccagcagggccagaatcagctgtacaacgagctgaacctgggcagaaggga
agagtacgacgtcctggataagcggagaggccgggaccctgagatgggcggcaagcctcggcggaagaaccccaggaa
ggcctgtataacgaactgcagaaagacaagatggccgaggcctacagcgagatcggcatgaagggcgagcggaggcgggg
caagggccacgacggcctgtatcagggcctgtccaccgccaccaaggatacctacgacgccctgcacatgcaggccctgccc
ccaagg

```
DNA: GAGAGCAAGTACGGACCGCCCTGCCCCCCTTGCCCTATGTTCTGGGTGCTG
 AA: E   S   K   Y   G   P   P   C   P   P   C   P   M   F   W   V   L

DNA: GTGGTGGTCGGAGGCGTGCTGGCCTGCTACAGCCTGCTGGTCACCGTGGCC
 AA: V   V   V   G   G   V   L   A   C   Y   S   L   L   V   T   V   A

DNA: TTCATCATCTTTTGGGTGAAACGGGGCAGAAAGAAACTCCTGTATATATTC
 AA: F   I   I   F   W   V   K   R   G   R   K   K   L   L   Y   I   F

DNA: AAACAACCATTTATGAGACCAGTACAAACTACTCAAGAGGAAGATGGCTGT
 AA: K   Q   P   F   M   R   P   V   Q   T   T   Q   E   E   D   G   C

DNA: AGCTGCCGATTTCCAGAAGAAGAAGAAGGAGGATGTGAACTGCGGGTGAAG
 AA: S   C   R   F   P   E   E   E   E   G   G   C   E   L   R   V   K

DNA: TTCAGCAGAAGCGCCGACGCCCCTGCCTACCAGCAGGGCCAGAATCAGCTG
 AA: F   S   R   S   A   D   A   P   A   Y   Q   Q   G   Q   N   Q   L

DNA: TACAACGAGCTGAACCTGGGCAGAAGGGAAGAGTACGACGTCCTGGATAAG
 AA: Y   N   E   L   N   L   G   R   R   E   E   Y   D   V   L   D   K

DNA: CGGAGAGGCCGGGACCCTGAGATGGGCGGCAAGCCTCGGCGGAAGAACCCC
 AA: R   R   G   R   D   P   E   M   G   G   K   P   R   R   K   N   P

DNA: CAGGAAGGCCTGTATAACGAACTGCAGAAAGACAAGATGGCCGAGGCCTAC
 AA: Q   E   G   L   Y   N   E   L   Q   K   D   K   M   A   E   A   Y

DNA: AGCGAGATCGGCATGAAGGGCGAGCGGAGGCGGGGCAAGGGCCACGACGGC
 AA: S   E   I   G   M   K   G   E   R   R   R   G   K   G   H   D   G

DNA: CTGTATCAGGGCCTGTCCACCGCCACCAAGGATACCTACGACGCCCTGCAC
 AA: L   Y   Q   G   L   S   T   A   T   K   D   T   Y   D   A   L   H

DNA: ATGCAGGCCCTGCCCCCAAGG
 AA: M   Q   A   L   P   P   R
```

FIG. 8

GMCSFRss-CD19scFv-Gly4ser linker-CD20scFv-huIgG4hinge/CH2/CH3-CD28tm/CD28cyto-41BB-CD3Zeta atgctgctgctggtgaccagcctgctgctgtgcgagctgccccacccccgcctttctgctgatccccgacatccagatgacccaga
ccacctccagcctgagcgccagcctgggcgaccgggtgaccatcagctgccgggccagccaggacatcagcaagtacctga
actggtatcagcagaagcccgacggcaccgtcaagctgctgatctaccacaccagccggctgcacagcggcgtgcccagcc
ggtttagcggcagcggctccggcaccgactacagcctgaccatctccaacctggaacaggaagatatcgccacctactttgcc
agcagggcaacacactgccctacacctttggcggcggaacaaagctggaaatcaccggcagcacctccggcagcggcaagc
ctggcagcggcgagggcagcaccaagggcgaggtgaagctgcaggaaagcggccctggcctggtggcccccagccagag
cctgagcgtgacctgcaccgtgagcggcgtgagcctgcccgactacggcgtgagctggatccggcagccccccaggaaggg
cctggaatggctgggcgtgatctggggcagcgagacccactactacaacagcgccctgaagagccggctgaccatcatcaag
gacaacagcaagagccaggtgttcctgaagatgaacagcctgcagaccgacgacaccgccatctactactgcgccaagcact
actactacggcggcagctacgccatggactactggggccagggcaccagcgtgaccgtgagcagcggaggtggtggatccg
aggtgcagctgcagcagtctggggctgagctggtgaagcctggggcctcagtgaagatgtcctgcaaggcttctggctacacat
ttaccagttacaatatgcactgggtaaagcagacacctggacagggcctggaatggattggagctatttatccaggaaatggtga
tacttcctacaatcagaagttcaaaggcaaggccacattgactgcagacaaatcctccagcacagcctacatgcagctcagcag
cctgacatctgaggactctgcggactattactgtgcaagatctaattattacggtagtagctactggttcttcgatgtctggggcgca
gggaccacggtcaccgtctcctcaggcagtactagcggtggtggctccggggggcggttccggtgggggcggcagcagcgac
attgtgctgacccaatctccagctatcctgtctgcatctccaggggagaaggtcacaatgacttgcagggccagctcaagtgtaa
attacatggactggtaccagaagaagccaggatcctcccccaaaccctggatttatgccacatccaacctggcttctggagtccct
gctcgcttcagtggcagtgggtctgggacctcttactctctcacaatcagcagagtggaggctgaagatgctgccacttattactg
ccagcagtggagttttaatccacccacgttcggaggggggaccaagctggaaataaaagagagcaagtacggaccgccctgc
cccccttgccctgccccgagttcctgggcggacccagcgtgttcctgttcccccccaagcccaaggacaccctgatgatcagc
cggacccccgaggtgacctgcgtggtggtggacgtgagccaggaagatcccgaggtccagttcaattggtacgtggacggcg
tggaagtgcacaacgccaagaccaagcccagagaggaacagttcaacagcacctacccgggtggtgtctgtgctgaccgtgct
gcaccaggactggctgaacggcaaagaatacaagtgcaaggtgtccaacaagggcctgcccagcagcatcgaaagaccat
cagcaaggccaagggccagcctcgcgagccccaggtgtacaccctgcctccctccaggaagagatgaccaagaaccaggt
gtccctgacctgcctggtgaagggcttctaccccagcgacatcgccgtggagtgggagagcaacggccagcctgagaacaac
tacaagaccacccctcccgtgctggacagcgacggcagcttcttcctgtacagccggctgaccgtggacaagagccggtggc
aggaaggcaacgtctttagctgcagcgtgatgcacgaggccctgcacaaccactacacccagaagagcctgagcctgtccctg
ggcaagatgttctgggtgctggtggtggtgggcggggtgctggcctgctacagcctgctggtgacagtggccttcatcatctttg
ggtgcggagcaagcggagcagaggcggccacagcgactacatgaacatgacccccagacggcctggccccacccggaag
cactaccagccctacgccccacccagggactttgccgcctacagaagcaaacggggcagaaagaaactcctgtatatattcaa
acaaccatttatgagaccagtacaaactactcaagaggaagatggctgtagctgccgatttccagaagaagaagaaggaggat
gtgaactgcgggtgaagttcagcagaagcgccgacgcccctgcctaccagcagggccagaatcagctgtacaacgagctgaa
cctgggcagaagggaagagtacgacgtcctggataagcggagaggccgggaccctgagatgggcggcaagcctcggcgg
aagaaccccaggaaggcctgtataacgaactgcagaaagacaagatggccgaggcctacagcgagatcggcatgaaggg
cgagcggaggcggggcaaggccacgacggcctgtatcagggcctgtccaccgccaccaaggatacctacgacgccctgc
acatgcaggccctgccccaagg

FIG. 9

GMCSFRss-CD19scFv-Gly4ser linker-CD20scFv-huIgG4hinge/CH2/CH3-
CD28tm/CD28cyto-41BB-CD3Zeta

```
DNA: ATGCTGCTGCTGGTGACCAGCCTGCTGCTGTGCGAGCTGCCCCACCCCGCC
AA:   M   L   L   L   V   T   S   L   L   L   C   E   L   P   H   P   A

DNA: TTTCTGCTGATCCCCGACATCCAGATGACCCAGACCACCTCCAGCCTGAGC
AA:   F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:   A   S   L   G   D   R   V   T   I   S   C   R   A   S   Q   D   I

DNA: AGCAAGTACCTGAACTGGTATCAGCAGAAGCCCGACGGCACCGTCAAGCTG
AA:   S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:   L   I   Y   H   T   S   R   L   H   S   G   V   P   S   R   F   S

DNA: GGCAGCGGCTCCGGCACCGACTACAGCCTGACCATCTCCAACCTGGAACAG
AA:   G   S   G   S   G   T   D   Y   S   L   T   I   S   N   L   E   Q

DNA: GAAGATATCGCCACCTACTTTTGCCAGCAGGGCAACACACTGCCCTACACC
AA:   E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:   F   G   G   G   T   K   L   E   I   T   G   S   T   S   G   S   G

DNA: AAGCCTGGCAGCGGCGAGGGCAGCACCAAGGGCGAGGTGAAGCTGCAGGAA
AA:   K   P   G   S   G   E   G   S   T   K   G   E   V   K   L   Q   E

DNA: AGCGGCCCTGGCCTGGTGGCCCCCAGCCAGAGCCTGAGCGTGACCTGCACC
AA:   S   G   P   G   L   V   A   P   S   Q   S   L   S   V   T   C   T

DNA: GTGAGCGGCGTGAGCCTGCCCGACTACGGCGTGAGCTGGATCCGGCAGCCC
AA:   V   S   G   V   S   L   P   D   Y   G   V   S   W   I   R   Q   P

DNA: CCCAGGAAGGGCCTGGAATGGCTGGGCGTGATCTGGGGCAGCGAGACCACC
AA:   P   R   K   G   L   E   W   L   G   V   I   W   G   S   E   T   T

DNA: TACTACAACAGCGCCCTGAAGAGCCGGCTGACCATCATCAAGGACAACAGC
AA:   Y   Y   N   S   A   L   K   S   R   L   T   I   I   K   D   N   S

DNA: AAGAGCCAGGTGTTCCTGAAGATGAACAGCCTGCAGACCGACGACACCGCC
AA:   K   S   Q   V   F   L   K   M   N   S   L   Q   T   D   D   T   A

DNA: ATCTACTACTGCGCCAAGCACTACTACTACGGCGGCAGCTACGCCATGGAC
AA:   I   Y   Y   C   A   K   H   Y   Y   Y   G   G   S   Y   A   M   D

DNA: TACTGGGGCCAGGGCACCAGCGTGACCGTGAGCAGCGGAGGTGGTGGATCC
AA:   Y   W   G   Q   G   T   S   V   T   V   S   S   G   G   G   S

DNA: GAGGTGCAGCTGCAGCAGTCTGGGGCTGAGCTGGTGAAGCCTGGGGCCTCA
AA:   E   V   Q   L   Q   Q   S   G   A   E   L   V   K   P   G   A   S

DNA: GTGAAGATGTCCTGCAAGGCTTCTGGCTACACATTTACCAGTTACAATATG
AA:   V   K   M   S   C   K   A   S   G   Y   T   F   T   S   Y   N   M
```

FIG. 9 continued

```
DNA: CACTGGGTAAAGCAGACACCTGGACAGGGCCTGGAATGGATTGGAGCTATT
AA:  H  W  V  K  Q  T  P  G  Q  G  L  E  W  I  G  A  I

DNA: TATCCAGGAAATGGTGATACTTCCTACAATCAGAAGTTCAAAGGCAAGGCC
AA:  Y  P  G  N  G  D  T  S  Y  N  Q  K  F  K  G  K  A

DNA: ACATTGACTGCAGACAAATCCTCCAGCACAGCCTACATGCAGCTCAGCAGC
AA:  T  L  T  A  D  K  S  S  S  T  A  Y  M  Q  L  S  S

DNA: CTGACATCTGAGGACTCTGCGGACTATTACTGTGCAAGATCTAATTATTAC
AA:  L  T  S  E  D  S  A  D  Y  Y  C  A  R  S  N  Y  Y

DNA: GGTAGTAGCTACTGGTTCTTCGATGTCTGGGGCGCAGGGACCACGGTCACC
AA:  G  S  S  Y  W  F  F  D  V  W  G  A  G  T  T  V  T

DNA: GTCTCCTCAGGCAGTACTAGCGGTGGTGGCTCCGGGGGCGGTTCCGGTGGG
AA:  V  S  S  G  S  T  S  G  G  G  S  G  G  G  S  G  G

DNA: GGCGGCAGCAGCGACATTGTGCTGACCCAATCTCCAGCTATCCTGTCTGCA
AA:  G  G  S  S  D  I  V  L  T  Q  S  P  A  I  L  S  A

DNA: TCTCCAGGGGAGAAGGTCACAATGACTTGCAGGGCCAGCTCAAGTGTAAAT
AA:  S  P  G  E  K  V  T  M  T  C  R  A  S  S  S  V  N

DNA: TACATGGACTGGTACCAGAAGAAGCCAGGATCCTCCCCCAAACCCTGGATT
AA:  Y  M  D  W  Y  Q  K  K  P  G  S  S  P  K  P  W  I

DNA: TATGCCACATCCAACCTGGCTTCTGGAGTCCCTGCTCGCTTCAGTGGCAGT
AA:  Y  A  T  S  N  L  A  S  G  V  P  A  R  F  S  G  S

DNA: GGGTCTGGGACCTCTTACTCTCTCACAATCAGCAGAGTGGAGGCTGAAGAT
AA:  G  S  G  T  S  Y  S  L  T  I  S  R  V  E  A  E  D

DNA: GCTGCCACTTATTACTGCCAGCAGTGGAGTTTTAATCCACCCACGTTCGGA
AA:  A  A  T  Y  Y  C  Q  Q  W  S  F  N  P  P  T  F  G

DNA: GGGGGGACCAAGCTGGAAATAAAAGAGAGCAAGTACGGACCGCCCTGCCCC
AA:  G  G  T  K  L  E  I  K  E  S  K  Y  G  P  P  C  P

DNA: CCTTGCCCTGCCCCCGAGTTCCTGGGCGGACCCAGCGTGTTCCTGTTCCCC
AA:  P  C  P  A  P  E  F  L  G  G  P  S  V  F  L  F  P

DNA: CCCAAGCCCAAGGACACCCTGATGATCAGCCGGACCCCCGAGGTGACCTGC
AA:  P  K  P  K  D  T  L  M  I  S  R  T  P  E  V  T  C

DNA: GTGGTGGTGGACGTGAGCCAGGAAGATCCCGAGGTCCAGTTCAATTGGTAC
AA:  V  V  V  D  V  S  Q  E  D  P  E  V  Q  F  N  W  Y

DNA: GTGGACGGCGTGGAAGTGCACAACGCCAAGACCAAGCCCAGAGAGGAACAG
AA:  V  D  G  V  E  V  H  N  A  K  T  K  P  R  E  E  Q

DNA: TTCAACAGCACCTACCGGGTGGTGTCTGTGCTGACCGTGCTGCACCAGGAC
AA:  F  N  S  T  Y  R  V  V  S  V  L  T  V  L  H  Q  D

DNA: TGGCTGAACGGCAAAGAATACAAGTGCAAGGTGTCCAACAAGGGCCTGCCC
AA:  W  L  N  G  K  E  Y  K  C  K  V  S  N  K  G  L  P
```

FIG. 9 continued

```
DNA: AGCAGCATCGAAAAGACCATCAGCAAGGCCAAGGGCCAGCCTCGCGAGCCC
AA:   S  S  I  E  K  T  I  S  K  A  K  G  Q  P  R  E  P

DNA: CAGGTGTACACCCTGCCTCCCTCCCAGGAAGAGATGACCAAGAACCAGGTG
AA:   Q  V  Y  T  L  P  P  S  Q  E  E  M  T  K  N  Q  V

DNA: TCCCTGACCTGCCTGGTGAAGGGCTTCTACCCCAGCGACATCGCCGTGGAG
AA:   S  L  T  C  L  V  K  G  F  Y  P  S  D  I  A  V  E

DNA: TGGGAGAGCAACGGCCAGCCTGAGAACAACTACAAGACCACCCCTCCCGTG
AA:   W  E  S  N  G  Q  P  E  N  N  Y  K  T  T  P  P  V

DNA: CTGGACAGCGACGGCAGCTTCTTCCTGTACAGCCGGCTGACCGTGGACAAG
AA:   L  D  S  D  G  S  F  F  L  Y  S  R  L  T  V  D  K

DNA: AGCCGGTGGCAGGAAGGCAACGTCTTTAGCTGCAGCGTGATGCACGAGGCC
AA:   S  R  W  Q  E  G  N  V  F  S  C  S  V  M  H  E  A

DNA: CTGCACAACCACTACACCCAGAAGAGCCTGAGCCTGTCCCTGGGCAAGATG
AA:   L  H  N  H  Y  T  Q  K  S  L  S  L  S  L  G  K  M

DNA: TTCTGGGTGCTGGTGGTGGTGGGCGGGGTGCTGGCCTGCTACAGCCTGCTG
AA:   F  W  V  L  V  V  V  G  G  V  L  A  C  Y  S  L  L

DNA: GTGACAGTGGCCTTCATCATCTTTTGGGTGCGGAGCAAGCGGAGCAGAGGC
AA:   V  T  V  A  F  I  I  F  W  V  R  S  K  R  S  R  G

DNA: GGCCACAGCGACTACATGAACATGACCCCCAGACGGCCTGGCCCCACCCGG
AA:   G  H  S  D  Y  M  N  M  T  P  R  R  P  G  P  T  R

DNA: AAGCACTACCAGCCCTACGCCCCACCCAGGGACTTTGCCGCCTACAGAAGC
AA:   K  H  Y  Q  P  Y  A  P  P  R  D  F  A  A  Y  R  S

DNA: AAACGGGGCAGAAAGAAACTCCTGTATATATTCAAACAACCATTTATGAGA
AA:   K  R  G  R  K  K  L  L  Y  I  F  K  Q  P  F  M  R

DNA: CCAGTACAAACTACTCAAGAGGAAGATGGCTGTAGCTGCCGATTTCCAGAA
AA:   P  V  Q  T  T  Q  E  E  D  G  C  S  C  R  F  P  E

DNA: GAAGAAGAAGGAGGATGTGAACTGCGGGTGAAGTTCAGCAGAAGCGCCGAC
AA:   E  E  E  G  G  C  E  L  R  V  K  F  S  R  S  A  D

DNA: GCCCCTGCCTACCAGCAGGGCCAGAATCAGCTGTACAACGAGCTGAACCTG
AA:   A  P  A  Y  Q  Q  G  Q  N  Q  L  Y  N  E  L  N  L

DNA: GGCAGAAGGGAAGAGTACGACGTCCTGGATAAGCGGAGAGGCCGGGACCCT
AA:   G  R  R  E  E  Y  D  V  L  D  K  R  R  G  R  D  P

DNA: GAGATGGGCGGCAAGCCTCGGCGGAAGAACCCCCAGGAAGGCCTGTATAAC
AA:   E  M  G  G  K  P  R  R  K  N  P  Q  E  G  L  Y  N

DNA: GAACTGCAGAAAGACAAGATGGCCGAGGCCTACAGCGAGATCGGCATGAAG
AA:   E  L  Q  K  D  K  M  A  E  A  Y  S  E  I  G  M  K

DNA: GGCGAGCGGAGGCGGGGCAAGGGCCACGACGGCCTGTATCAGGGCCTGTCC
AA:   G  E  R  R  R  G  K  G  H  D  G  L  Y  Q  G  L  S
```

FIG. 9 continued

```
DNA: ACCGCCACCAAGGATACCTACGACGCCCTGCACATGCAGGCCCTGCCCCCA
 AA: T   A   T   K   D   T   Y   D   A   L   H   M   Q   A   L   P   P

DNA: AGG
 AA: R
```

FIG. 10

GMCSFRss-CD19scFv-Gly4ser linker-CD20scFv-CD8alphaHinge-CD8alphaTM-41BB-CD3Zeta-T2A-EGFRt atgctgctgctggtgaccagcctgctgctgtgcgagctgccccaccccgcctttctgctgatccccgacatccagatgacccaga
ccacctccagcctgagcgccagcctgggcgaccgggtgaccatcagctgccgggccagccaggacatcagcaagtacctga
actggtatcagcagaagcccgacggcaccgtcaagctgctgatctaccacaccagccggctgcacagcggcgtgcccagcc
ggtttagcggcagcggctccggcaccgactacagcctgaccatctccaacctggaacaggaagatatcgccacctactttgcc
agcagggcaacacactgccctacacctttggcggcggaacaaagctggaaatcaccggcagcacctccggcagcggcaagc
ctggcagcggcgagggcagcaccaagggcgaggtgaagctgcaggaaagcggccctggcctggtggcccccagccagag
cctgagcgtgacctgcaccgtgagcggcgtgagcctgcccgactacggcgtgagctggatccggcagccccccaggaaggg
cctggaatggctgggcgtgatctgggcagcgagaccacctactacaacagcgccctgaagagccggctgaccatcatcaag
gacaacagcaagagccaggtgttcctgaagatgaacagcctgcagaccgacgacaccgccatctactactgcgccaagcact
actactacggcggcagctacgccatggactactggggccagggcaccagcgtgaccgtgagcagcggaggtggtggatccg
aggtgcagctgcagcagtctggggctgagctggtgaagcctggggcctcagtgaagatgtcctgcaaggcttctggctacacat
taccagttacaatatgcactgggtaaagcagacacctggacagggcctggaatggattggagctatttatccaggaaatggtga
tacttcctacaatcagaagttcaaaggcaaggccacattgactgcagacaaatcctccagcacagcctacatgcagctcagcag
cctgacatctgaggactctgcggactattactgtgcaagatctaattattacggtagtagctactggttcttcgatgtctggggcgca
gggaccacggtcaccgtctcctcaggcagtactagcggtggtggctccggggcggttccggtgggggcggcagcagcgac
attgtgctgacccaatctccagctatcctgtctgcatctccaggggagaaggtcacaatgacttgcagggccagctcaagtgtaa
attacatgcactggtaccagaagaagccaggatcctcccccaaaccctggatttatgccacatccaacctggcttctggagtccct
gctcgcttcagtggcagtgggtctgggacctcttactctctcacaatcagcagagtggaggctgaagatgctgccacttattactg
ccagcagtggagttttaatccacccacgttcggaggggggaccaagctggaaataaaagagagcaagtacggaccgccctgc
cccccttgccctaagcctaccaccacccctgcccctagacctccaacacccgccccaacaatcgccagccagcctctgtctctg
aggcccgaggcttgtagaccagctgctggcggagccgtgcacaccagaggactggatttcgcctgcgacatctacatctgggc
ccctctggccggcacatgtggcgtgctgctgctgagcctcgtgatcaccaagcgggggcagaaagaaactgctgtacatcttaa
gcagcccttcatgcggcccgtgcagaccacccaggaagaggacggctgctcctgcagattccccgaggaagaagaaggcgg
ctgcgagctgagagtgaagttcagcagatccgccgacgcccctgcctaccagcagggacagaaccagctgtacaacgagctg
aacctgggcagacgggaagagtacgacgtgctggacaagcggagaggccgggaccctgagatgggcggaaagcccagaa
gaaagaacccccaggaaggcctgtataacgaactgcagaaagacaagatggccgaggcctacagcgagatcggaatgaag
ggcgagcggagaagaggcaaggccacgatggcctgtaccagggcctgagcaccgccaccaaggacacctatgacgccct
gcacatgcaggccctgcctccaagactcgagggcggcggagagggcagaggaagtcttctaacatgcggtgacgtggagga
gaatcccggccctaggatgcttctcctggtgacaagccttctgctctgtgagttaccacacccagcattcctcctgatcccacgca
aagtgtgtaacggaataggtattggtgaatttaaagactcactctccataaatgctacgaatattaaacacttcaaaaactgcacctc
catcagtggcgatctccacatcctgccggtggcatttaggggtgactccttcacacatactcctcctctggatccacaggaactgg
atattctgaaaaccgtaaaggaaatcacagggttttgctgattcaggcttggcctgaaaacaggacggacctccatgcctttgag
aacctagaaatcatacgcggcaggaccaagcaacatggtcagttttctcttgcagtcgtcagcctgaacataacatccttgggatt
acgctccctcaaggagataagtgatggagatgtgataatttcaggaaacaaaaatttgtgctatgcaaatcaataaactggaaaa
aactgtttgggacctccggtcagaaaaccaaaattataagcaacagaggtgaaaacagctgcaaggccacaggccaggtctgc
catgccttgtgctcccccgagggctgctggggcccggagcccagggactgcgtctcttgccggaatgtcagccgaggcaggg
aatgcgtggacaagtgcaaccttctggagggtgagccaagggagtttgtggagaactctgagtgcatacagtgccacccagag
tgcctgcctcaggccatgaacatcacctgcacaggacgggaccagacaactgtatccagtgtgcccactacattgacggccc
ccactgcgtcaagacctgcccggcaggagtcatgggagaaaacaacacccctggtctggaagtacgcagacgccggccatgtg
tgccacctgtgccatccaaactgcacctacggatgcactgggccaggtcttgaaggctgtccaacgaatgggcctaagatccg
tccatcgccactgggatggtgggggcccctcctcttgctgctggtggtggccctggggatcggcctcttcatgtga

FIG. 11

GMCSFRss-CD19scFv-Gly4ser linker-CD20scFv-CD8alphaHinge-CD8alphaTM-41BB-CD3Zeta-T2A-EGFRt

```
DNA: ATGCTGCTGCTGGTGACCAGCCTGCTGCTGTGCGAGCTGCCCCACCCCGCC
AA:  M   L   L   L   V   T   S   L   L   L   C   E   L   P   H   P   A

DNA: TTTCTGCTGATCCCCGACATCCAGATGACCCAGACCACCTCCAGCCTGAGC
AA:  F   L   L   I   P   D   I   Q   M   T   Q   T   T   S   S   L   S

DNA: GCCAGCCTGGGCGACCGGGTGACCATCAGCTGCCGGGCCAGCCAGGACATC
AA:  A   S   L   G   D   R   V   T   I   S   C   R   A   S   Q   D   I

DNA: AGCAAGTACCTGAACTGGTATCAGCAGAAGCCCGACGGCACCGTCAAGCTG
AA:  S   K   Y   L   N   W   Y   Q   Q   K   P   D   G   T   V   K   L

DNA: CTGATCTACCACACCAGCCGGCTGCACAGCGGCGTGCCCAGCCGGTTTAGC
AA:  L   I   Y   H   T   S   R   L   H   S   G   V   P   S   R   F   S

DNA: GGCAGCGGCTCCGGCACCGACTACAGCCTGACCATCTCCAACCTGGAACAG
AA:  G   S   G   S   G   T   D   Y   S   L   T   I   S   N   L   E   Q

DNA: GAAGATATCGCCACCTACTTTTGCCAGCAGGGCAACACACTGCCCTACACC
AA:  E   D   I   A   T   Y   F   C   Q   Q   G   N   T   L   P   Y   T

DNA: TTTGGCGGCGGAACAAAGCTGGAAATCACCGGCAGCACCTCCGGCAGCGGC
AA:  F   G   G   G   T   K   L   E   I   T   G   S   T   S   G   S   G

DNA: AAGCCTGGCAGCGGCGAGGGCAGCACCAAGGGCGAGGTGAAGCTGCAGGAA
AA:  K   P   G   S   G   E   G   S   T   K   G   E   V   K   L   Q   E

DNA: AGCGGCCCTGGCCTGGTGGCCCCCAGCCAGAGCCTGAGCGTGACCTGCACC
AA:  S   G   P   G   L   V   A   P   S   Q   S   L   S   V   T   C   T

DNA: GTGAGCGGCGTGAGCCTGCCCGACTACGGCGTGAGCTGGATCCGGCAGCCC
AA:  V   S   G   V   S   L   P   D   Y   G   V   S   W   I   R   Q   P

DNA: CCCAGGAAGGGCCTGGAATGGCTGGGCGTGATCTGGGGCAGCGAGACCACC
AA:  P   R   K   G   L   E   W   L   G   V   I   W   G   S   E   T   T

DNA: TACTACAACAGCGCCCTGAAGAGCCGGCTGACCATCATCAAGGACAACAGC
AA:  Y   Y   N   S   A   L   K   S   R   L   T   I   I   K   D   N   S

DNA: AAGAGCCAGGTGTTCCTGAAGATGAACAGCCTGCAGACCGACGACACCGCC
AA:  K   S   Q   V   F   L   K   M   N   S   L   Q   T   D   D   T   A

DNA: ATCTACTACTGCGCCAAGCACTACTACTACGGCGGCAGCTACGCCATGGAC
AA:  I   Y   Y   C   A   K   H   Y   Y   Y   G   G   S   Y   A   M   D

DNA: TACTGGGGCCAGGGCACCAGCGTGACCGTGAGCAGCGGAGGTGGTGGATCC
AA:  Y   W   G   Q   G   T   S   V   T   V   S   S   G   G   G   G   S

DNA: GAGGTGCAGCTGCAGCAGTCTGGGGCTGAGCTGGTGAAGCCTGGGGCCTCA
AA:  E   V   Q   L   Q   Q   S   G   A   E   L   V   K   P   G   A   S

DNA: GTGAAGATGTCCTGCAAGGCTTCTGGCTACACATTTACCAGTTACAATATG
AA:  V   K   M   S   C   K   A   S   G   Y   T   F   T   S   Y   N   M
```

FIG. 11 continued

```
DNA: CACTGGGTAAAGCAGACACCTGGACAGGGCCTGGAATGGATTGGAGCTATT
AA:  H  W  V  K  Q  T  P  G  Q  G  L  E  W  I  G  A  I

DNA: TATCCAGGAAATGGTGATACTTCCTACAATCAGAAGTTCAAAGGCAAGGCC
AA:  Y  P  G  N  G  D  T  S  Y  N  Q  K  F  K  G  K  A

DNA: ACATTGACTGCAGACAAATCCTCCAGCACAGCCTACATGCAGCTCAGCAGC
AA:  T  L  T  A  D  K  S  S  S  T  A  Y  M  Q  L  S  S

DNA: CTGACATCTGAGGACTCTGCGGACTATTACTGTGCAAGATCTAATTATTAC
AA:  L  T  S  E  D  S  A  D  Y  Y  C  A  R  S  N  Y  Y

DNA: GGTAGTAGCTACTGGTTCTTCGATGTCTGGGGCGCAGGGACCACGGTCACC
AA:  G  S  S  Y  W  F  F  D  V  W  G  A  G  T  T  V  T

DNA: GTCTCCTCAGGCAGTACTAGCGGTGGTGGCTCCGGGGGCGGTTCCGGTGGG
AA:  V  S  S  G  S  T  S  G  G  G  S  G  G  G  S  G  G

DNA: GGCGGCAGCAGCGACATTGTGCTGACCCAATCTCCAGCTATCCTGTCTGCA
AA:  G  G  S  S  D  I  V  L  T  Q  S  P  A  I  L  S  A

DNA: TCTCCAGGGGAGAAGGTCACAATGACTTGCAGGGCCAGCTCAAGTGTAAAT
AA:  S  P  G  E  K  V  T  M  T  C  R  A  S  S  S  V  N

DNA: TACATGGACTGGTACCAGAAGAAGCCAGGATCCTCCCCCAAACCCTGGATT
AA:  Y  M  D  W  Y  Q  K  K  P  G  S  S  P  K  P  W  I

DNA: TATGCCACATCCAACCTGGCTTCTGGAGTCCCTGCTCGCTTCAGTGGCAGT
AA:  Y  A  T  S  N  L  A  S  G  V  P  A  R  F  S  G  S

DNA: GGGTCTGGGACCTCTTACTCTCTCACAATCAGCAGAGTGGAGGCTGAAGAT
AA:  G  S  G  T  S  Y  S  L  T  I  S  R  V  E  A  E  D

DNA: GCTGCCACTTATTACTGCCAGCAGTGGAGTTTTAATCCACCCACGTTCGGA
AA:  A  A  T  Y  Y  C  Q  Q  W  S  F  N  P  P  T  F  G

DNA: GGGGGGACCAAGCTGGAAATAAAAGAGAGCAAGTACGGACCGCCCTGCCCC
AA:  G  G  T  K  L  E  I  K  E  S  K  Y  G  P  P  C  P

DNA: CCTTGCCCTAAGCCTACCACCACCCCTGCCCCTAGACCTCCAACACCCGCC
AA:  P  C  P  K  P  T  T  T  P  A  P  R  P  P  T  P  A

DNA: CCAACAATCGCCAGCCAGCCTCTGTCTCTGAGGCCCGAGGCTTGTAGACCA
AA:  P  T  I  A  S  Q  P  L  S  L  R  P  E  A  C  R  P

DNA: GCTGCTGGCGGAGCCGTGCACACCAGAGGACTGGATTTCGCCTGCGACATC
AA:  A  A  G  G  A  V  H  T  R  G  L  D  F  A  C  D  I

DNA: TACATCTGGGCCCCTCTGGCCGGCACATGTGGCGTGCTGCTGCTGAGCCTC
AA:  Y  I  W  A  P  L  A  G  T  C  G  V  L  L  L  S  L

DNA: GTGATCACCAAGCGGGGCAGAAAGAAACTGCTGTACATCTTTAAGCAGCCC
AA:  V  I  T  K  R  G  R  K  K  L  L  Y  I  F  K  Q  P

DNA: TTCATGCGGCCCGTGCAGACCACCCAGGAAGAGGACGGCTGCTCCTGCAGA
AA:  F  M  R  P  V  Q  T  T  Q  E  E  D  G  C  S  C  R
```

FIG. 11 continued

```
DNA: TTCCCCGAGGAAGAAGAAGGCGGCTGCGAGCTGAGAGTGAAGTTCAGCAGA
AA:  F P E E E E G G C E L R V K F S R

DNA: TCCGCCGACGCCCTGCCTACCAGCAGGGACAGAACCAGCTGTACAACGAG
AA:  S A D A P A Y Q Q G Q N Q L Y N E

DNA: CTGAACCTGGGCAGACGGGAAGAGTACGACGTGCTGGACAAGCGGAGAGGC
AA:  L N L G R R E E Y D V L D K R R G

DNA: CGGGACCCTGAGATGGGCGGAAAGCCCAGAAGAAAGAACCCCCAGGAAGGC
AA:  R D P E M G G K P R R K N P Q E G

DNA: CTGTATAACGAACTGCAGAAGACAAGATGGCCGAGGCCTACAGCGAGATC
AA:  L Y N E L Q K D K M A E A Y S E I

DNA: GGAATGAAGGGCGAGCGGAGAAGAGGCAAGGGCCACGATGGCCTGTACCAG
AA:  G M K G E R R R G K G H D G L Y Q

DNA: GGCCTGAGCACCGCCACCAAGGACACCTATGACGCCCTGCACATGCAGGCC
AA:  G L S T A T K D T Y D A L H M Q A

DNA: CTGCCTCCAAGACTCGAGGGCGGCGGAGAGGGCAGAGGAAGTCTTCTAACA
AA:  L P P R L E G G G E G R G S L L T

DNA: TGCGGTGACGTGGAGGAGAATCCCGGCCCTAGGATGCTTCTCCTGGTGACA
AA:  C G D V E E N P G P R M L L L V T

DNA: AGCCTTCTGCTCTGTGAGTTACCACACCCAGCATTCCTCCTGATCCCACGC
AA:  S L L L C E L P H P A F L L I P R

DNA: AAAGTGTGTAACGGAATAGGTATTGGTGAATTTAAAGACTCACTCTCCATA
AA:  K V C N G I G I G E F K D S L S I

DNA: AATGCTACGAATATTAAACACTTCAAAAACTGCACCTCCATCAGTGGCGAT
AA:  N A T N I K H F K N C T S I S G D

DNA: CTCCACATCCTGCCGGTGGCATTTAGGGGTGACTCCTTCACACATACTCCT
AA:  L H I L P V A F R G D S F T H T P

DNA: CCTCTGGATCCACAGGAACTGGATATTCTGAAAACCGTAAAGGAAATCACA
AA:  P L D P Q E L D I L K T V K E I T

DNA: GGGTTTTGCTGATTCAGGCTTGGCCTGAAAACAGGACGGACCTCCATGCC
AA:  G F L L I Q A W P E N R T D L H A

DNA: TTTGAGAACCTAGAAATCATACGCGGCAGGACCAAGCAACATGGTCAGTTT
AA:  F E N L E I I R G R T K Q H G Q F

DNA: TCTCTTGCAGTCGTCAGCCTGAACATAACATCCTTGGGATTACGCTCCCTC
AA:  S L A V V S L N I T S L G L R S L

DNA: AAGGAGATAAGTGATGGAGATGTGATAATTTCAGGAAACAAAAATTTGTGC
AA:  K E I S D G D V I I S G N K N L C

DNA: TATGCAAATACAATAAACTGGAAAAAACTGTTTGGGACCTCCGGTCAGAAA
AA:  Y A N T I N W K K L F G T S G Q K
```

FIG. 11 continued

```
DNA: ACCAAAATTATAAGCAACAGAGGTGAAAACAGCTGCAAGGCCACAGGCCAG
 AA: T  K  I  I  S  N  R  G  E  N  S  C  K  A  T  G  Q

DNA: GTCTGCCATGCCTTGTGCTCCCCGAGGGCTGCTGGGGCCCGGAGCCCAGG
 AA: V  C  H  A  L  C  S  P  E  G  C  W  G  P  E  P  R

DNA: GACTGCGTCTCTTGCCGGAATGTCAGCCGAGGCAGGGAATGCGTGGACAAG
 AA: D  C  V  S  C  R  N  V  S  R  G  R  E  C  V  D  K

DNA: TGCAACCTTCTGGAGGGTGAGCCAAGGGAGTTTGTGGAGAACTCTGAGTGC
 AA: C  N  L  L  E  G  E  P  R  E  F  V  E  N  S  E  C

DNA: ATACAGTGCCACCCAGAGTGCCTGCCTCAGGCCATGAACATCACCTGCACA
 AA: I  Q  C  H  P  E  C  L  P  Q  A  M  N  I  T  C  T

DNA: GGACGGGGACCAGACAACTGTATCCAGTGTGCCCACTACATTGACGGCCCC
 AA: G  R  G  P  D  N  C  I  Q  C  A  H  Y  I  D  G  P

DNA: CACTGCGTCAAGACCTGCCCGGCAGGAGTCATGGGAGAAAACAACACCCTG
 AA: H  C  V  K  T  C  P  A  G  V  M  G  E  N  N  T  L

DNA: GTCTGGAAGTACGCAGACGCCGGCCATGTGTGCCACCTGTGCCATCCAAAC
 AA: V  W  K  Y  A  D  A  G  H  V  C  H  L  C  H  P  N

DNA: TGCACCTACGGATGCACTGGGCCAGGTCTTGAAGGCTGTCCAACGAATGGG
 AA: C  T  Y  G  C  T  G  P  G  L  E  G  C  P  T  N  G

DNA: CCTAAGATCCCGTCCATCGCCACTGGGATGGTGGGGGCCCTCCTCTTGCTG
 AA: P  K  I  P  S  I  A  T  G  M  V  G  A  L  L  L  L

DNA: CTGGTGGTGGCCCTGGGGATCGGCCTCTTCATGTGA
 AA: L  V  V  A  L  G  I  G  L  F  M  *
```

FIG. 12

T2A-EGFRt ctcgagggcggcggagagggcagaggaagtcttctaacatgcggtgacgtggaggagaatcccggccctaggatgcttctcc
tggtgacaagccttctgctctgtgagttaccacacccagcattcctcctgatcccacgcaaagtgtgtaacggaataggtattggtg
aatttaaagactcactctccataaatgctacgaatattaaacacttcaaaaactgcacctccatcagtggcgatctccacatcctgcc
ggtggcatttagggggtgactccttcacacatactcctcctctggatccacaggaactggatattctgaaaaccgtaaaggaaatca
cagggttttgctgattcaggcttggcctgaaaacaggacggacctccatgcctttgagaacctagaaatcatacgcggcaggac
caagcaacatggtcagttttctcttgcagtcgtcagcctgaacataacatccttgggattacgctccctcaaggagataagtgatgg
agatgtgataatttcaggaaacaaaaatttgtgctatgcaaatacaataaactggaaaaaactgtttgggacctccggtcagaaaa
ccaaaattataagcaacagaggtgaaaacagctgcaaggccacaggccaggtctgccatgccttgtgctcccccgagggctgc
tggggcccggagcccagggactgcgtctcttgccggaatgtcagccgaggcagggaatgcgtggacaagtgcaaccttctgg
agggtgagccaagggagtttgtggagaactctgagtgcatacagtgccacccagagtgcctgcctcaggccatgaacatcacc
tgcacaggacggggaccagacaactgtatccagtgtgcccactacattgacggccccactgcgtcaagacctgcccggcag
gagtcatgggagaaaacaacaccctggtctggaagtacgcagacgccggccatgtgtgccaccgtgccatccaaactgcacc
tacggatgcactgggccaggtcttgaaggctgtccaacgaatgggcctaagatcccgtccatcgccactgggatggtgggggc
cctcctcttgctgctggtggtggccctggggatcggcctcttcatgtga

FIG. 13

T2A-EGFRt

```
DNA: CTCGAGGGCGGCGGAGAGGGCAGAGGAAGTCTTCTAACATGCGGTGACGTG
AA:   L   E   G   G   G   E   G   R   G   S   L   L   T   C   G   D   V

DNA: GAGGAGAATCCCGGCCCTAGGATGCTTCTCCTGGTGACAAGCCTTCTGCTC
AA:   E   E   N   P   G   P   R   M   L   L   L   V   T   S   L   L   L

DNA: TGTGAGTTACCACACCCAGCATTCCTCCTGATCCCACGCAAAGTGTGTAAC
AA:   C   E   L   P   H   P   A   F   L   L   I   P   R   K   V   C   N

DNA: GGAATAGGTATTGGTGAATTTAAAGACTCACTCTCCATAAATGCTACGAAT
AA:   G   I   G   I   G   E   F   K   D   S   L   S   I   N   A   T   N

DNA: ATTAAACACTTCAAAAACTGCACCTCCATCAGTGGCGATCTCCACATCCTG
AA:   I   K   H   F   K   N   C   T   S   I   S   G   D   L   H   I   L

DNA: CCGGTGGCATTTAGGGGTGACTCCTTCACACATACTCCTCCTCTGGATCCA
AA:   P   V   A   F   R   G   D   S   F   T   H   T   P   P   L   D   P

DNA: CAGGAACTGGATATTCTGAAAACCGTAAAGGAAATCACAGGGTTTTTGCTG
AA:   Q   E   L   D   I   L   K   T   V   K   E   I   T   G   F   L   L

DNA: ATTCAGGCTTGGCCTGAAAACAGGACGGACCTCCATGCCTTTGAGAACCTA
AA:   I   Q   A   W   P   E   N   R   T   D   L   H   A   F   E   N   L

DNA: GAAATCATACGCGGCAGGACCAAGCAACATGGTCAGTTTTCTCTTGCAGTC
AA:   E   I   I   R   G   R   T   K   Q   H   G   Q   F   S   L   A   V

DNA: GTCAGCCTGAACATAACATCCTTGGGATTACGCTCCCTCAAGGAGATAAGT
AA:   V   S   L   N   I   T   S   L   G   L   R   S   L   K   E   I   S

DNA: GATGGAGATGTGATAATTTCAGGAAACAAAAATTTGTGCTATGCAAATACA
AA:   D   G   D   V   I   I   S   G   N   K   N   L   C   Y   A   N   T

DNA: ATAAACTGGAAAAAACTGTTTGGGACCTCCGGTCAGAAAACCAAAATTATA
AA:   I   N   W   K   K   L   F   G   T   S   G   Q   K   T   K   I   I

DNA: AGCAACAGAGGTGAAAACAGCTGCAAGGCCACAGGCCAGGTCTGCCATGCC
AA:   S   N   R   G   E   N   S   C   K   A   T   G   Q   V   C   H   A

DNA: TTGTGCTCCCCCGAGGGCTGCTGGGGCCCGGAGCCCAGGGACTGCGTCTCT
AA:   L   C   S   P   E   G   C   W   G   P   E   P   R   D   C   V   S

DNA: TGCCGGAATGTCAGCCGAGGCAGGGAATGCGTGGACAAGTGCAACCTTCTG
AA:   C   R   N   V   S   R   G   R   E   C   V   D   K   C   N   L   L

DNA: GAGGGTGAGCCAAGGGAGTTTGTGGAGAACTCTGAGTGCATACAGTGCCAC
AA:   E   G   E   P   R   E   F   V   E   N   S   E   C   I   Q   C   H

DNA: CCAGAGTGCCTGCCTCAGGCCATGAACATCACCTGCACAGGACGGGGACCA
AA:   P   E   C   L   P   Q   A   M   N   I   T   C   T   G   R   G   P

DNA: GACAACTGTATCCAGTGTGCCCACTACATTGACGGCCCCCACTGCGTCAAG
AA:   D   N   C   I   Q   C   A   H   Y   I   D   G   P   H   C   V   K
```

FIG. 13 continued

```
DNA: ACCTGCCCGGCAGGAGTCATGGGAGAAAACAACACCCTGGTCTGGAAGTAC
 AA:  T  C  P  A  G  V  M  G  E  N  N  T  L  V  W  K  Y

DNA: GCAGACGCCGGCCATGTGTGCCACCTGTGCCATCCAAACTGCACCTACGGA
 AA:  A  D  A  G  H  V  C  H  L  C  H  P  N  C  T  Y  G

DNA: TGCACTGGGCCAGGTCTTGAAGGCTGTCCAACGAATGGGCCTAAGATCCCG
 AA:  C  T  G  P  G  L  E  G  C  P  T  N  G  P  K  I  P

DNA: TCCATCGCCACTGGGATGGTGGGGGCCCTCCTCTTGCTGCTGGTGGTGGCC
 AA:  S  I  A  T  G  M  V  G  A  L  L  L  L  V  V  A

DNA: CTGGGGATCGGCCTCTTCATGTGA
 AA:  L  G  I  G  L  F  M  *
```

POLYNUCLEOTIDES ENCODING BISPECIFIC CHIMERIC ANTIGEN RECEPTORS

CROSS-REFERENCE TO RELATED APPLICATIONS

This application is a divisional of U.S. patent application Ser. No. 15/233,140 filed Aug. 10, 2016, now U.S. Pat. No. 10,189,903, which claims the benefit of priority under 35 U.S.C. § 120 as a continuation of U.S. patent application Ser. No. 14/376,610, filed Aug. 4, 2014, now U.S. Pat. No. 9,447,194, which is the National Phase of International Application No. PCT/US13/25953, filed Feb. 13, 2013, now expired, which designated the U.S. and that International Application was published under PCT Article 21(2) in English, which claims priority under 35 U.S.C. § 119(e) to U.S. provisional patent application No. 61/598,216, filed Feb. 13, 2012, the contents of each of which are herein incorporated by reference in their entirety.

REFERENCE TO SEQUENCE LISTING

The Sequence Listing submitted Jan. 4, 2019, as a text file named "SCHSequenceListing_ST25" created on Dec. 14, 2018 and having a size of 104,783 bytes, is hereby incorporated by reference.

FIELD OF INVENTION

The invention relates to chimeric antigen receptors and to genetically engineered cells using the same.

BACKGROUND OF THE INVENTION

Current immunotherapies are designed to target single antigens on cancer cells. However, for example, cancer cells are unstable and some cells may no longer possess the target antigen. These cells, referred to as antigen loss escape variants, escape destruction by the therapy and may continue to grow and spread unchecked. Therefore there is a need in the art for therapies which prevent or minimize therapeutic failures in cancer and other diseases.

SUMMARY OF THE INVENTION

In an embodiment, the invention provides a bispecific chimeric antigen receptor, comprising (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen, and wherein the bispecific chimeric antigen receptor is co-expressed with a therapeutic control.

In an embodiment, the invention further provides a combination of a bispecific chimeric antigen receptor and a therapeutic control, wherein the bispecific chimeric antigen receptor comprises (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen.

In an embodiment, the invention further provides a bispecific chimeric antigen receptor, comprising (a) at least two antigen-specific targeting regions, (b) an extracellular spacer domain, (c) a transmembrane domain, (d) at least one co-stimulatory domain and (e) an intracellular signaling domain, wherein each antigen-specific targeting region comprises an antigen-specific single chain Fv (scFv) fragment, and binds a different antigen, and wherein the bispecific chimeric antigen receptor is co-expressed with truncated epidermal growth factor receptor (EGFRt).

In an embodiment, the invention further provides a bispecific chimeric antigen receptor, comprising (a) at least two antigen-specific targeting regions, (b) a CD8αhinge extracellular spacer domain, (c) a CD8α transmembrane domain, (d) a 4-1BB co-stimulatory domain and (vi) a CD3 zeta intracellular signaling domain, wherein each antigen-specific targeting region comprises an antigen-specific single chain Fv (scFv) fragment, and binds a different antigen, wherein the bispecific chimeric antigen receptor is co-expressed with EGFRt and wherein the bispecific chimeric antigen receptor and EGFRt are linked via a T2A linker.

In an embodiment, also provided are pharmaceutical compositions comprising the above-described bispecific chimeric antigen receptors, a combination of the bispecific chimeric antigen receptors and therapeutic controls, polypeptides encoding the bispecific chimeric antigen receptors, vectors, viruses and genetically engineered cells comprising the bispecific chimeric antigen receptors, vectors, viruses and genetically engineered cells comprising a combination of the bispecific chimeric antigen receptors and therapeutic controls, or combinations thereof, and a pharmaceutically acceptable carrier.

BRIEF DESCRIPTION OF FIGURES

Exemplary embodiments are illustrated in the referenced figures. It is intended that the embodiments and figures disclosed herein are to be considered illustrative rather than restrictive.

FIGS. 2A and 2B. FIG. 2A depicts the components of an anti-CD19×CD20 CAR, and FIG. 2B depicts a complete cDNA packaged into an epHIV-7 lentivirus vector transfer plasmid, in accordance with an embodiment of the present invention.

FIG. 3 depicts, in accordance with an embodiment of the present invention, the nucleic acid sequence of a bispecific CAR CD19scFv-Gly4Ser1linker-CD20scFv-IgG4Hinge-CD28tm-41BB-CD3zeta-T2A-EGFRt_epHIV7 (SEQ ID NO: 1).

FIG. 4 depicts, in accordance with an embodiment of the present invention, the nucleic acid and amino acid sequences of a bispecific CAR CD19scFv-Gly4Ser1linker-CD20scFv-IgG4Hinge-CD28tm-41BB-CD3zeta-T2A-EGFRt_epHIV7 (SEQ ID NO: 2, which includes the nucleic acid sequence from SEQ ID NO:1 and the amino acid sequence from SEQ ID NO: 3).

FIG. 6A Schematic diagrams of wild type versus chimeric cytokine receptors. The IL-7Rα constitutive cytokine receptor (CγCR7) consists of the human IL-7 cytokine tethered to the full length human IL-7Rα chain via a $(G_4S)_2$ linker. The IL-2Rβ constitutive cytokine receptor (CγCR2) is identical to CγCR7 except that the IL-7Rα intracellular signaling domain is replaced with the human IL-2/IL-15Rβ cytoplasmic domain. FIG. 6B Diagram of the expression construct CγCR-T2A-CD19t.

FIG. 7 depicts, in accordance with an embodiment of the present invention, the nucleic acid and amino acid sequences (SEQ ID NO: 4 and SEQ ID NO: 5) of an embodiment of the invention, namely a backbone CAR comprising the hinge region of IgG4, the transmembrane domain of CD28, the costimulatory domain of 4-1BB and the cytoplasmic domain of CD3zeta.

FIG. 8 depicts, in accordance with an embodiment of the present invention, the nucleic acid sequence of an embodiment of the invention, namely GMCSFRss-CD19scFv-Gly4Serlinker-CD20scFv-huIgGHinge/CH2/CH3-CD28tm/CD28cyto-41BB-CD3zeta (SEQ ID NO: 7). GMCSFRss is the signal sequence from GMCSFR.

FIG. 9 depicts, in accordance with an embodiment of the present invention, the nucleic acid and amino acid sequences of an embodiment of the invention, namely GMCSFRss-CD19scFv-Gly4Serlinker-CD20scFv-huIgGHinge/CH2/CH3-CD28tm/CD28cyto-41BB-CD3zeta (SEQ ID NO: 8, which includes the nucleic acid sequence from SEQ ID NO: 7 and the amino acid sequence from SEQ ID NO: 9), GMCSFRss is the signal sequence from GMCSFR.

FIG. 10 depicts, in accordance with an embodiment of the present invention, the nucleic acid sequence of an embodiment of the invention, namely the GMCSFRss-CD19scFv-Gly4Serlinker-CD20scFv-CD8αHinge-CD8αtm-41BB-CD3zeta-T2A-EGFRt (SEQ ID NO: 10), GMCSFRss is the signal sequence from GMCSFR.

FIG. 11 depicts, in accordance with an embodiment of the present invention, the nucleic acid and amino acid sequences of an embodiment of the invention, namely GMCSFRss-CD19scFv-Gly4Serlinker-CD20scFv-CD8αHinge-CD8αtm-41BB-CD3zeta-T2A-EGFRt (SEQ ID NO: 11, which includes the nucleic acid sequence from SEQ ID NO: 10 and the amino acid sequence from SEQ ID NO: 12). GMCSFRss is the signal sequence from GMCSFR.

FIG. 12 depicts, in accordance with an embodiment of the present invention, the nucleic acid sequence of an embodiment of an invention namely T2A-EGFRt (SEQ ID NO: 13).

FIG. 13 depicts, in accordance with an embodiment of the present invention, the nucleic acid and amino acid sequences of an embodiment of the invention, namely T2A-EGFRt (SEQ ID NO: 14, which includes the nucleic acid sequence from SEQ ID NO: 13 and the amino acid sequence from SEQ ID NO: 15).

DETAILED DESCRIPTION OF THE INVENTION

Figure 1:
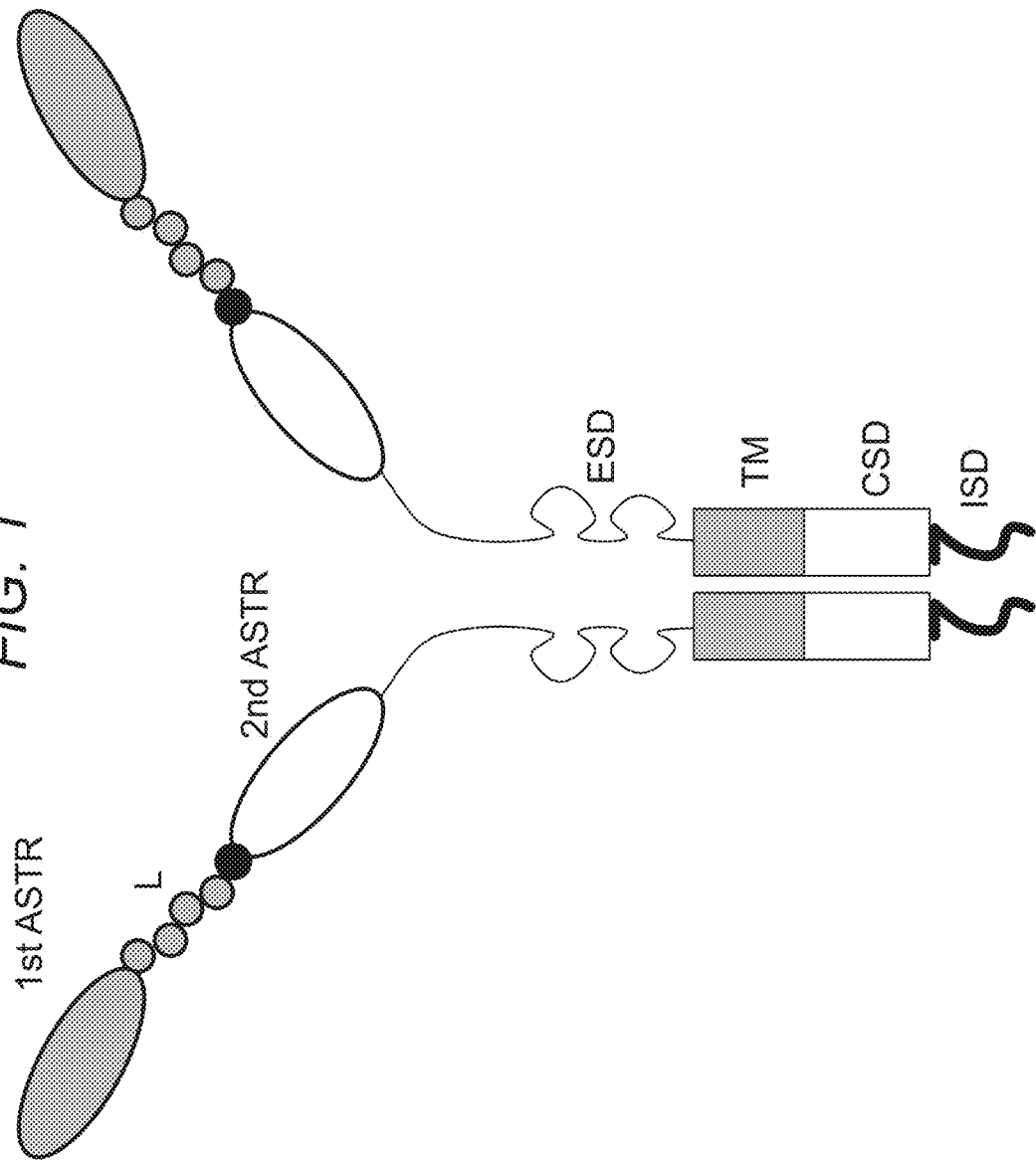
FIG. 1 depicts a schematic representation of a chimeric antigen receptor of the invention, in accordance with an embodiment of the present invention. ASTR is an antigen-specific targeting region, L is a linker. ESD is an extracellular spacer domain, TM is a transmembrane domain, CSD is a co-stimulatory domain, and ISD is an intracellular signaling domain.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The invention described herein provides chimeric antigen receptors. Chimeric antigen receptors are engineered receptors Which graft an immune specificity onto a genetically engineered cell. By housing specificities to multiple antigens in a single chimeric antigen receptor (CAR), various benefits may be achieved, including, among others, a significant reduction in effort as compared to making multiple T-cell products per patient.

Definitions

Components of the Chimeric Antigen Receptors

"Antigen-specific targeting region" (ASTR) as used herein refers to the region of the CAR which targets specific antigens. The CARs of the invention comprise at least two targeting regions which target at least two different antigens. In an embodiment, CARs comprise three or more targeting regions which target at least three or more different antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells hearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the invention. In fact, almost any molecule that binds a given antigen with high affinity can be used as an antigen-specific targeting region, as will be appreciated by those of skill in the art.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors or chimeric immunoreceptors. The CARs of the invention comprise at least two antigen-specific targeting regions, an extracellular domain, a transmembrane domain, one or more co-stimulatory domains, and an intracellular signaling domain. The two or more antigen-specific targeting regions target at least two different antigens and may be arranged in tandem and separated by linker sequences. In an embodiment, the extracellular spacer domain is optional. In another embodiment, the CAR is a bispecific CAR. A bispecific CAR is specific to two different antigens.

"Co-stimulatory domain" (CSD) as used herein refers to the portion of the CAR which enhances the proliferation, survival and/or development of memory cells. The CARs of the invention may comprise one or more co-stimulatory domains. Each co-stimulatory domain comprises the costimulatory domain of any one or more of, for example, members of the TNFR superfamily, CD28, CD137 (4-1BB), CD134 (OX40), Dap10, CD27, CD2, CD5, ICAM-1, LFA-1(CD11a/CD18), Lck, TNFR-I, TNFR-II, Fas, CD30, CD40 or combinations thereof. Other co-stimulatory domains (e.g., from other proteins) will be apparent to those of skill in the art and may be used in connection with alternate embodiments of the invention.

"Extracellular spacer domain" (ESD) as used herein refers to the hydrophilic region which is between the antigen-specific targeting region and the transmembrane domain. In some embodiments, the CARs of the invention comprise an extracellular spacer domain. In other embodiments, the CARs of the invention do not comprise an extracellular spacer domain. The extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof. Examples of extracellular spacer domains include but are not limited to CD8α hinge, and artificial spacers made of polypeptides which may be as small as, for example, Gly3 or CH1 and CH3 domains of IgGs (such as human IgG4). In some embodiments, the extracellular spacer domain is any one or more of (i) a hinge, CH2 and CH3 regions of IgG4, (ii) a hinge region of IgG4, (iii) a hinge and CH2 of IgG4, (iv) a hinge region of CD8α, (v) a hinge, CH2 and CH3 regions of IgG1, (vi) a hinge region of IgG1 or (vi) a hinge and CH2 region of IgG1. Other extracellular spacer domains will be apparent to those of skill in the art and may be used in connection with alternate embodiments of the invention.

"Intracellular signaling domain" (ISD) or "cytoplasmic domain" as used herein refer to the portion of the CAR which transduces the effector function signal and directs the cell to perform its specialized function. Examples of domains that transduce the effector function signal include but are not limited to the ζ chain of the T-cell receptor complex or any of its homologs (e.g., η chain, FcεR1γ and β chains, MB1 (Igα) chain, B29 (Igβ) chain, etc.), human CD3 zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. Other intracellular signaling domains will be apparent to those of skill in the art and may be used in connection with alternate embodiments of the invention.

"Linker" (L) or "linker domain" or "linker region" as used herein refer to an oligo- or polypeptide region from about 1 to 100 amino acids in length, which links together any of the domains/regions of the CAR of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), Thosea asigna virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ motif, which results in cleavage between the 2A glycine and the 2B proline. Other linkers will be apparent to those of skill in the art and may be used in connection with alternate embodiments of the invention.

"Transmembrane domain" (TMD) as used herein refers to the region of the CAR which crosses the plasma membrane. The transmembrane domain of the CAR of the invention is the transmembrane region of a transmembrane protein (for example Type I transmembrane proteins), an artificial hydrophobic sequence or a combination thereof. Other transmembrane domains will be apparent to those of skill in the art and may be used in connection with alternate embodiments of the invention.

Others

"Antigen loss escape variants" as used herein refer to cells which exhibit reduced or loss of expression of the target antigen, which antigens are targeted by the CARs of the invention.

"B-cell associated diseases" as used herein include B-cell immunodeficiencies, autoimmune diseases and/or excessive/uncontrolled cell proliferation associated with B-cells (including lymphomas and/or leukemias). Examples of such diseases, wherein bispecific CARs of the invention may be used for therapeutic approaches include but are not limited to systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemis, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinaemia and/or hyper IgM syndrome, as well as virally-mediated B-cell diseases such as EBV mediated lymphoproliferative disease, and chronic infections in which B-cells participate in the pathophysiology.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Co-express" as used herein refers to simultaneous expression of two or more genes. Genes may be nucleic acids encoding, for example, a single protein or a chimeric protein as a single polypeptide chain. For example, the CARs of the invention may be co-expressed with a therapeutic control (for example truncated epidermal growth factor (EGFRt)), wherein the CAR is encoded by a first polynucleotide chain and the therapeutic control is encoded by a second polynucleotide chain. In an embodiment, the first and second polynucleotide chains are linked by a nucleic acid sequence that encodes a cleavable linker. The polynucleotides encoding the CAR and the therapeutic control system may be linked by IRES sequences. Alternately, the CAR and the therapeutic control are encoded by two different polynucleotides that are not linked via a linker but are instead encoded by, for example, two different vectors. Further, the CARs of the invention may be co-expressed with a therapeutic control and CCR, a therapeutic control and DHFR (for example mutant DHFR) or a therapeutic control and CCR and DHFR (for example mutant DHFR). The CAR, therapeutic control and CCR may be co-expressed and encoded by first, second and third polynucleotide sequences, respectively, wherein the first, second and third polynucleotide sequences are linked via IRES sequences or sequences encoding cleavable linkers. Alternately, these sequences are not linked via linkers but instead are encoded via, for example, separate vectors. The CAR, therapeutic control and DHFR (for example mutant DHFR) may be co-expressed and encoded by first, second and fourth polynucleotide sequences, respectively, wherein the first, second and fourth polynucleotide sequences are linked via IRES sequences or via sequences encoding cleavable linkers. Alternately, these sequences are not linked via linkers but instead encoded via, for example, separate vectors. The CAR, therapeutic control, CCR and DHFR (for example mutant DHFR) may be co-expressed and encoded by first, second, third and fourth polynucleotide sequences, respectively, wherein the first, second, third and fourth polynucleotide sequences are linked via IRES sequences or sequences encoding cleavable linkers. Alternately, these sequences are not linked via linkers but instead are encoded via, for example, separate vectors. If the aforementioned sequences are encoded by separate vectors, these vectors may be simultaneously or sequentially transfected.

"Conditions", "disease conditions," "diseases" and "disease state" as used herein include physiological states in which diseased cells may be targeted with the CARs of the invention, expressing, for example, antibodies against specific antigens on the diseased cells. Examples of antigens which may be targeted include but are not limited to antigens expressed on B-cells (such as CD19 and CD20), antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

"Disease targeted by genetically modified cells" as used herein encompasses the targeting of any cell involved in any manner in any disease by the genetically modified cells of the invention, irrespective of whether the genetically modified cells target diseased cells or healthy cells to effectuate a therapeutically beneficial result. The genetically modified cells include but are not limited to genetically modified T-cells, NK cells, hematopoietic stem cells, pluripotent embryonic stem cells or embryonic stem cells. The genetically modified cells express the CARs of the invention, which CARs may target any of the antigens expressed on the surface of target cells. Examples of antigens which may be targeted include but are not limited to antigens expressed on B-cells; antigens expressed on carcinomas, sarcomas, lymphomas, leukemia, germ cell tumors, and blastomas; antigens expressed on various immune cells; and antigens expressed on cells associated with various hematologic diseases, autoimmune diseases, and/or inflammatory diseases. Other antigens that may be targeted will be apparent to those of skill in the art and may be targeted by the CARs of the invention in connection with alternate embodiments thereof.

"Effector function" refers to the specialized function of a differentiated cell. Effector function of a T-cell, for example, may be cytolytic activity or helper activity including the secretion of cytokines.

"Genetically modified cells", "redirected cells", "genetically engineered cells" or "modified cells" as used herein refer to cells that express the CAR of the invention.

"Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

"Immune response" as used herein refers to immunities including but not limited to innate immunity, humoral immunity, cellular immunity, immunity, inflammatory response, acquired (adaptive) immunity, autoimmunity and/or overactive immunity.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

"Naked DNA" as used herein refers to DNA encoding a CAR cloned in a suitable expression vector in proper orientation for expression. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments of the invention will be apparent to those of skill in the art.

"Single chain variable fragment", "single-chain antibody variable fragments" or "scFv" antibodies as used herein refer to forms of antibodies comprising the variable regions of only the heavy and light chains, connected by a linker peptide.

"Target cell" as used herein refers to cells which are involved in a disease and can be targeted by the genetically modified cells of the invention (including but not limited to genetically modified T-cells, NK cells, hematopoietic stem cells, pluripotent stem cells, and embryonic stem cells). Other target cells will be apparent to those of skill in the art and may be used in connection with alternate embodiments of the invention.

The terms "T-cell" and "T-lymphocyte" are interchangeable and used synonymously herein. Examples include but are not limited to naïve T cells, central memory T cells, effector memory T cells or combinations thereof.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

"Therapeutic controls" as used herein refers to agents that regulate cell proliferation, facilitate cell selection (for example selecting cells which express the chimeric antigen receptors of the invention), facilitate cell tracking or a combination thereof. In one embodiment, regulating cell proliferation comprises up-regulating cell proliferation to promote cell propagation. In another embodiment, regulating cell proliferation comprises down-regulating cell proliferation so as to reduce or inhibit cell propagation. In some embodiments, the agents that serve as therapeutic controls may promote enrichment of cells which express the bispecific chimeric antigen receptors which may result in a therapeutic advantage.

"Transduction" as used herein refers to the introduction of a foreign nucleic acid into a cell using a viral vector.

"Transfection" as used herein refers to the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, such as a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species "Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Tumor," as used herein refers to all neoplastic cell growth and proliferation, whether malignant or benign, and all pre-cancerous and cancerous cells and tissues.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

DESCRIPTION OF THE INVENTION

Chimeric Antigen Receptors

While not wishing to be limited by any one premise, it is believed that the chimeric antigen receptors (for example bispecific CARs) of the instant invention may overcome conventional therapeutic failures due to, for example, outgrowth of antigen loss escape variants that can arise in the course of various therapies when a single antigen is targeted. Accordingly, the invention is directed to, among other things, nucleic acid sequences and amino acid sequences encoding CARs, vectors comprising CARs, viruses comprising CARs, genetically modified cells comprising the CARs (redirected cells) and methods of making and using them. In some embodiments, the CARs are bispecific CARs. In other embodiments, the CARs target and bind three or more different antigens.

In general embodiments, the present invention relates to CARs (for example bispecific CARs), nucleic acid sequences encoding the CARs (for example bispecific CARs), the vectors comprising the nucleic acids encoding the CARs (for example bispecific CARs), viruses comprising the nucleic acid sequences encoding the CARs (for example bispecific CARs), host cells (such as genetically modified cells) expressing the CARs (for example bispecific CARs), combinations of CARs (for example bispecific CARs) and therapeutic controls and methods of making and using the CARs (for example bispecific CARs) as therapeutic agents.

The CARs of the invention target at least two different antigens. The CARs (such as bispecific CARs) are co-expressed with a therapeutic control; for instance, truncated epidermal growth factor receptor (EGFRt), chimeric cytokine receptors (CCR) and/or dihydroxyfolate receptor (DHFR) (e.g., mutant DHFR). The polynucleotides encoding the CAR and the therapeutic control(s) may be linked via IRES sequences or via polynucleotide sequences encoding cleavable linkers. The CARs of the invention are constructed so that they may be expressed in cells, which in turn proliferate in response to the presence of at least one molecule that interacts with at least one antigen-specific targeting region, for instance, an antigen.

In some embodiments, therapeutic controls for use with the CARs of the invention comprise any one or more of truncated epidermal growth factor receptor (EGFRt), thymidine kinase, cytosine deaminase, nitroreductase, xanthine-guanine phosphoribosyl transferase, human caspase 8, human caspase 9, purine nucleoside phosphorylase, linamarase/linamarin/glucose oxidase, deoxyribonucleoside kinase, horseradish peroxidase (HRP)/indole-3-acetic (IAA), Gamma-glutamylcysteine synthetase, CD20/alphaCD20, CD34/thymidine kinase chimera, dox-dependent caspase-2, mutant thymidine kinase (HSV-TKSR39) or AP1903/Fas system. In an embodiment, the CARs of the invention are linked to EGFRt via a cleavable linker or IRES sequences. In another embodiment, a bispecific CAR is linked to EGFRt via a cleavable linker or IRES sequences.

The CARs described herein may be synthesized as single polypeptide chains and may comprise at least two antigen-specific targeting regions, an extracellular spacer domain, a transmembrane domain, one or more co-stimulatory domains and an intracellular signaling domain. In this embodiment, the antigen-specific targeting regions are at the N-terminus, arranged in tandem and are separated by a linker peptide. The antigen-specific targeting region is linked to an extracellular spacer domain which is linked to the transmembrane domain. The transmembrane domain is linked to the co-stimulatory domain. The co-stimulatory domain is linked to the intracellular signaling domain which is at the C-terminus if more than one co-stimulatory domain is used, the multiple co-stimulatory domains may be arranged in tandem with the transmembrane domain at its N-terminus and the intracellular signaling domain at its C-terminus. Polynucleotides encoding these polypeptides may further comprise an N-terminal signal sequence which directs the CAR to the cell surface as a type I transmembrane protein. The antigen-specific targeting region may be extracellular-facing and the intracellular signaling domain may be cytoplasmic.

FIG. 1 shows a schematic of a chimeric antigen receptor of the invention.

In an embodiment, an extracellular spacer domain in the CAR is optional. In such a CAR, the antigen-specific targeting regions are at the N-terminus, arranged in tandem, and separated by a linker peptide. The antigen-specific targeting region may be linked to the transmembrane domain. The transmembrane domain may be linked to the co-stimulatory domain. The co-stimulatory domain may be linked to the intracellular signaling domain, which is at the C-terminus. If more than one co-stimulatory domain is used, the multiple co-stimulatory domains may be arranged in tandem with the transmembrane domain at its N-terminus and the intracellular signaling domain at its C-terminus. Polynucleotides encoding these polypeptides may further comprise an N-terminal signal sequence which directs the CAR to the cell surface as a type I transmembrane protein. The antigen-specific targeting region may be extracellular-facing and the intracellular signaling domain may be cytoplasmic.

Antigen-Specific Targeting Regions of Chimeric Antigen Receptors

The CARs of the invention may target several (such as two or more, three or more) different antigens. In an embodiment, the CAR is a bispecific CAR and targets two different antigens. As described above, the antigen-specific targeting regions of the CAR may be arranged in tandem and may be separated by linker peptides. The antigens targeted by the CAR may be antigens on single diseased cell (such as a cancerous B-cell) or antigens that are expressed on separate cells that each contribute to the disease. The antigens targeted by the CAR are antigens which are either directly or indirectly involved in the disease.

In a bispecific CAR, at least two different antigen-specific antibodies or fragments thereof or derivatives thereof may be cloned into the antigen-specific targeting region. The antibodies may be specific for any, but at least two, distinct antigens of choice. The antibody specific to the antigen may be the Fab fragment of the antibody or the single chain variable fragment (scFv) of the antibody.

For example, FIGS. 2A and 2B show an embodiment of the invention depicting a CAR specific to CD19 and CD20. Using methods well known to one skilled in the art, scFvs specific to multiple, but at least two different antigens, may be cloned upstream (i.e., to N-terminus) of the IgG4-CD28-zeta domains so long as the target-antigens are expressed on cells that are targetable by the genetically modified cells described below. Such techniques are explained fully in the literature. (Sambrook et al, "Molecular Cloning: A Laboratory Manual" (1989), Current Protocols in Molecular Biology. Volumes I-III [Ausubel, R. M., ed. (1994))], Cell Biology: A Laboratory Handbook. Volumes I-III [J. E. Celis, ed. (1994))], Current Protocols in Immunology. Volumes [Coligan, J. E., ed. (1994)], Oligonucleotide Synthesis. (M. J. Gait ed. 1984), Nucleic Acid Hybridization [B. D. Hames & S. J. Higgins eds. (1985)], Transcription And Translation [B. D. Hames & S. J. Higgins, eds. (1984)], Animal Cell Culture [R. I. Freshney, ed. (1986)], Immobilized Cells And Enzymes [IRL Press, (1986)], Practical Guide To Molecular Cloning B. Perbal (1984), Current Protocols in Immunology (J. E. Coligan, A. M. Kruisbeek, D. H. Margulies, E. M. Shevach and W. Strober, eds., 1991), Annual Review of Immunology as well as monographs in journals such as Advances in Immunology).

In one embodiment, each antigen-specific targeting region comprises the full-length IgG heavy chain (specific for the target antigen) having the $V_H$, CH1, hinge, and the CH2 and CH3 (Fc) Ig domains, if the $V_H$ domain alone is sufficient to confer antigen-specificity ("single-domain antibodies"). The full length IgG heavy chain may be linked to the co-stimulatory domain and the intracellular signaling domain via the appropriate transmembrane domain. If both, the $V_H$ and the $V_L$ domains, are necessary to generate a fully active antigen-specific targeting region, the $V_H$-containing CAR and the full-length lambda light chain (IgL) are both introduced into the cells to generate an active antigen-specific targeting region. In an embodiment, an extracellular spacer domain may be linked between the antigen-specific binding domain and the transmembrane domain. The cells include but are not limited to T-lymphocytes (T-cells), natural killer cells, hematopoietic stem cells and/or pluripotent embryonic/induced stem cells capable of giving rise to therapeutically relevant progeny.

In another embodiment, each antigen-specific targeting region of the CAR comprises at least two single chain antibody variable fragments (scFv), each specific for a different target antigen, says, in which the C-terminus of one variable domain ($V_H$ or $V_L$) is tethered to the N-terminus of the other ($V_L$ or $V_H$, respectively) via a polypeptide linker, have been developed without significantly disrupting antigen binding or specificity of the binding. (Chaudhary et al., A recombinant single-chain immunotoxin composed of anti-Tac variable regions and a truncated diphtheria toxin. 1990 *Proc. Natl. Acad. Sci.*, 87:9491; Bedzyk et al. Immunological and structural characterization of a high affinity anti-fluorescein single-chain antibody. 1990 *J. Biol. Chem.*, 265: 18615). The linker connects the N-terminus of the $V_H$ with the C-terminus of $V_L$ or the C-terminus of $V_H$ with the N-terminus of $V_L$. These scFvs lack the constant regions (Fc) present in the heavy and light chains of the native antibody. The says, specific for at least two different antigens, are arranged in tandem and linked to the co-stimulatory domain and the intracellular signaling domain via a transmembrane domain. In an embodiment, an extracellular spacer domain may be linked between the antigen-specific binding region and the transmembrane domain.

In another aspect, each scFv fragment may be fused to all or a portion of the constant domains of the heavy chain. The resulting antigen-specific targeting region, specific for at least two different antigens, is joined to the co-stimulatory domain and the intracellular signaling domain via a transmembrane domain, in an embodiment, an extracellular spacer domain may be linked between the antigen-specific binding domain and the transmembrane domain.

In a further embodiment, each antigen-specific targeting region of the CAR comprises a divalent (or bivalent) single-chain variable fragment (di-scFvs, bi-scFvs). In CARs comprising di-scFVs, two scFvs specific for each antigen are linked together by producing a single peptide chain with two $V_H$ and two $V_L$ regions, yielding tandem scFvs. (Xiong, Cheng-Yi; Natarajan, A; Shi, X B; Denardo, G L; Denardo, S J (2006). "Development of tumor targeting anti-MUC-1 multimer: effects of di-scFv unpaired cysteine location on PEGylation and tumor binding". *Protein Engineering Design and Selection* 19 (8): 359-367; Kufer, Peter; Lutterbüse, Ralf; Baeuerle, Patrick A. (2004). "A revival of bispecific antibodies". *Trends in Biotechnology* 22 (5): 238-

244). CARs comprising at least two antigen-specific targeting regions would express two scFvs specific for each of the two antigens. The resulting antigen-specific targeting region, specific for at least two different antigens, is joined to the co-stimulatory domain and the intracellular signaling domain via a transmembrane domain. In an embodiment, an extracellular spacer domain may be linked between the antigen-specific binding domain and the transmembrane domain.

In an additional embodiment, each antigen-specific targeting region of the CAR comprises a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used.

To create the CARs of the present invention, two or more individual antigen-specific targeting regions are connected to each other, either covalently or noncovalently, on a single protein molecule. An oligo- or polypeptide linker, an Fc hinge or membrane hinge region may be used to connect these domains to each other. The CARs of the present invention may comprise two or more of the different antigen-specific targeting regions connected together in different combinations. For example, two or more antigen-specific targeting regions containing immunoglobulin sequences (e.g. scFvs and/or single-domain antibodies) may be linked to each other.

Targets of Antigen-Specific Targeting Regions of Chimeric Antigen Receptors

In some embodiments, the antigen-specific targeting region of the CAR (for example bispecific CAR) targets antigens specific for cancer, inflammatory disease, neuronal-disorders, diabetes, cardiovascular disease, infectious diseases or a combination thereof. Examples of antigens which may be targeted by the CARs (for example bispecific CARs) of the invention include but are not limited to antigens expressed on B-cells, antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases. The CARs of the invention, which are specific for at least two different target antigens, may be capable of redirecting the effector function of the expressing-cells to either of both of the target antigens. This feature of the construct may overcome the issue of antigen loss escape variants when targeting, for example, genetically unstable B-cell lineage malignancies using single antigen-specificity.

Antigens specific for cancer which may be targeted by the CARs (for example bispecific CARs) of the invention include but are not limited to any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-1, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin. Other antigens specific for cancer will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

In some embodiments, the bispecific chimeric antigen receptors target and bind at least two different antigens. Examples of pairings of at least two antigens bound by the bispecific CARs of the invention include but are not limited to CD19 and CD20, CD19 and CD22, CD20 and L1-CAM, L1-CAM and GD2, EGFR and L1-CAM, EGFR and C-MET, EGFR and HER2, C-MET and HER2 and EGFR and ROR1. Other pairings of antigens specific for cancer will be apparent to those of skill in the art and may be used in connection with alternate embodiments of the invention. In yet other embodiments, the bispecific chimeric antigen receptor targets CD19 and CD20. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for inflammatory diseases which may be targeted by the CARs of the invention include but are not limited to any one or more of AOC3 (VAP-1), CAM-3001, CCL11 (eotaxin-1), CD125, CD147 (basigin), CD154 (CD40L), CD2, CD20, CD23 (IgE receptor), CD25 (α chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, Lama glama, LFA-1 (CD11a), MEDI-528, myostatin, OX-40, rhuMAb β7, scleroscin, SOST, TGF beta 1, TNF-α or VEGF-A. Other antigens specific for inflammatory diseases will be apparent to those of skill in the art and may be used in connection with alternate embodiments of the invention. Examples of CARs which target the above antigens include but are not limited to bispecific CARs, bispecific CARs co-expressed with EGFRt bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for neuronal disorders which may be targeted by the CARs of the invention include but are not limited to any one or more of beta amyloid or MABT5102A. Other antigens specific for neuronal disorders will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for diabetes which may be targeted by the CARs of the invention include but are not limited to any one or more of L-1β or CD3. Other antigens specific for diabetes or other metabolic disorders will be apparent to those of skill in the art and may be used in connection with alternate embodiments of the invention. Examples of CARs which target the above antigens include but are not limited to bispecific CARs, bispecific CAR co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for cardiovascular diseases which may be targeted by the CARs of the invention include but are not limited to any one or more of C5, cardiac myosin, CD41 (integrin alpha-IIb), fibrin II, beta chain, ITGB2 (CD18) and sphingosine-1-phosphate. Other antigens specific for cardiovascular diseases will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Antigens specific for infectious diseases which may be targeted by the CARs of the invention include but are not limited to any one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α. Other antigens specific for infectious diseases will be apparent to those of skill in the art and may be used in connection with alternate embodiments of the invention. Examples of CARs which target the above antigens include but are not limited to bispecific CARs, bispecific CARs co-expressed with EGFRt, bispecific CARs co-expressed with EGFRt and CCR, bispecific CARs co-expressed with EGFRt and DHFR (for example mutant DHFR) or bispecific CARs co-expressed with EGFRt and CDR and DHFR (for example mutant DHFR).

Further examples of target antigens include but are not limited to surface proteins found on cancer cells in a specific or amplified fashion (e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas), or viral proteins (e.g. gp120 and gp41 envelope proteins of HIV, envelope proteins from the Hepatitis B and C viruses, the glycoprotein B and other envelope glycoproteins of human cytomegalovirus, the envelope proteins from oncoviruses such as Kaposi's sarcoma-associated Herpes virus). Other potential targets of the CARs of the invention include CD4, where the ligand is the HIV gp120 envelope glycoprotein, and other viral receptors, for example ICAM, which is the receptor for the human rhinovirus, and the related receptor molecule for poliovirus.

Additional targets of the CARs of the invention include antigens involved in B-cell associated diseases. Yet further targets of the CARs of the invention will be apparent to those of skill in the art and may be used in connection with alternate embodiments of the invention.

Co-Stimulatory Domains of Chimeric Antigen Receptors

The CARs of the invention may also comprise a co-stimulatory domain. This domain may enhance cell proliferation, cell survival and development of memory cells. The CARs of the invention may comprise one or more co-stimulatory domains. Each co-stimulatory domain comprises the co-stimulatory domain of any one or more of, for example, members of the TNFR super family, CD28, CD137 (4-1BB), CD134 (OX40), Dap10, CD27, CD2, CD5, ICAM-1, Lck, TNFR-1, TNFR-II, Fas, CD30, CD40 or combinations thereof. Co-stimulatory domains from other proteins may also be used with the CARs of the invention. Additional co-stimulatory domains will be apparent to those of skill in the art and may be used in connection with alternate embodiments of the invention. If a CAR comprises more than one co-stimulatory domain, these domains may be arranged in tandem, optionally separated by a linker.

Extracellular Spacer Domain of Chimeric Antigen Receptor

The CARs of the invention may further comprise an extracellular spacer domain. In some embodiments, this domain facilitates proper protein folding. The extracellular spacer domain comprises a hydrophilic region which is attached to the antigen-specific targeting region and the transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions antibodies, artificial spacer sequences or combinations thereof. Examples of extracellular spacer domains include but are not limited to CD8α hinge, artificial spacers made of polypeptides such as Gly3, or CH1, CH3 domains of IgG's (such as human IgG4). Specifically, the extracellular spacer domain may be (i) a hinge, CH2 and CH3 regions of IgG4, (ii) a hinge region of IgG4, (iii) a hinge and CH2 of IgG4, (iv) a hinge region of CD8α, (v) a hinge, CH2 and CH3 regions of IgG1, (vi) a hinge region of IgG1 or (vi) a hinge and CH2 of IgG1 or a combination thereof. Additional extracellular spacer domains will be apparent to those of skill in the art and may be used in connection with alternate embodiments of the invention.

Transmembrane Domain of Chimeric Antigen Receptors

The CARs of the invention may also comprise a transmembrane domain. The transmembrane domain may comprise the transmembrane sequence from any protein which has a transmembrane domain, including any of the type I, type II or type III transmembrane proteins. The transmembrane domain of the CAR of the invention may also comprise an artificial hydrophobic sequence. The transmembrane domains of the CARs of the invention may be selected so as not to dimerize. Additional transmembrane domains will be apparent to those of skill in the art and may be used in connection with alternate embodiments of the invention.

Intracellular Signaling Domain of Chimeric Antigen Receptors

The CARs of the invention may also comprise an intracellular signaling domain. This domain may be cytoplasmic and may transduce the effector function signal and direct the cell to perform its specialized function. Examples of intracellular signaling domains include, but are not limited to, ζ chain of the T-cell receptor or any of its homologs (e.g., η chain, FcεR1γ and β chains. MB1 (Igα) chain, B29 (Igβ) chain, etc.). CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. Specifically, the intracellular signaling domain may be human CD3 zeta chain, FcγRIII, FcεRI, cytoplasmic tails of Fc receptors, immunoreceptor tyrosine-based activation motif (ITAM) bearing cytoplasmic receptors or combinations thereof. Additional intracellular signaling domains will be apparent to those of skill in the art and may be used in connection with alternate embodiments of the invention.

Linkers in Chimeric Antigen Receptors

In some embodiments, two or more components of the CARs of the invention are separated by one or more linkers. For example, in CARs comprising at least two antigen-specific targeting regions, the first targeting region on the CAR may be separated from the second targeting region on the CAR via a linker. Additionally, the CAR may be linked to therapeutic controls via a linker. Linkers are oligo- or polypeptides region from about 1 to 100 amino acids in length, that link together any of the domains/regions of the CAR of the invention. In some embodiments, the linkers may be for example, 5-12 amino acids in length, 5-15 amino acids in length or 5 to 20 amino acids in length. Linkers may be composed of flexible residues like glycine and serine so that the adjacent protein domains are free to move relative to one another. Longer linkers, for example those longer than 100 amino acids, may be used in connection with alternate embodiments of the invention, and may be selected to, for example, ensure that two adjacent domains do not sterically interfere with one another. Examples of linkers which may be used in the instant invention include but are not limited to 2A linkers (for example T2A), 2A-like linkers or functional equivalents thereof.

Therapeutic Controls

Therapeutic controls regulate cell proliferation, facilitate cell selection (for example selecting cells which express the chimeric antigen receptors of the invention) or a combination thereof. In one embodiment, regulating cell proliferation comprises up-regulating cell proliferation to promote cell propagation. In another embodiment, regulating cell proliferation comprises down-regulating cell proliferation so as to reduce or inhibit cell propagation. In some embodiments, the agents that serve as therapeutic controls may promote enrichment of cells which express the bispecific chimeric antigen receptors which may result in a therapeutic advantage. In some embodiments, agents which serve as therapeutic controls may biochemically interact with additional compositions so as to regulate the functioning of the therapeutic controls. For example, EGFRt (a therapeutic control) may biochemically interact with cetuximab so as to regulate the function of EGFRt in selection, tracking, cell ablation or a combination thereof.

Examples of therapeutic controls include but are not limited to any one or more of truncated epidermal growth factor receptor (EGFRt), thymidine kinase, cytosine deaminase, nitroreductase, xanthine-guanine phosphoribosyl transferase, human caspase 8, human caspase 9, purine nucleoside phosphorylase, linamarase/linamarin/glucose oxidase, deoxyribonucleoside kinase, horseradish peroxidase (HRP)/indole-3-acetic (IAA), Gamma-glutamylcysteine synthetase, CD20/alphaCD20, CD34/thymidine kinase chimera, dox-dependent caspase-2, mutant thymidine kinase (HSV-TKSR39), AP1903/Fas system, a chimeric cytokine receptor (CCR), a selection marker, and combinations thereof. In some embodiments, the therapeutic controls are co-expressed with the bispecific chimeric antigen receptor.

Examples of agents which regulate the functioning of the therapeutic controls include but are not limited to any one or more of HERCEPTIN®, methotrexate, cetuximab, thymidine analogs (for example ganciclovir), (E)-5-(2-bromovinyl)-2'-deoxyuridine (BVDU), 5-flurocytosine (5-FC), 5-(azaridin-1-yl)-2, 4-dinitrobenzamide (CB1954), 6-thioguanine, a synthetic dimerizing drug (for example API903), fludarabine phosphate, linamarin (lin), nucleoside analogs (for example BVDU, difluorodeoxycytidine (dFdC), 1-β-D-arabinofuranosylthymine (ara-T)), indole-3-acetic (IAA), 1-buthionine-S,R-sulfoximine (BSO), rituximab (RTX), doxycycline, tyrosine kinase inhibitors or combinations thereof. These agents may be administered before, during or after the use of the therapeutic controls.

As described above, the CARs of the invention may be synthesized as single polypeptide chains. If the CAR is a bispecific CAR, the polynucleotide sequence encoding the CAR may be, for example, in the following configuration in the N-terminal to C-terminal direction: N-terminal signal sequence—antigen-specific targeting region 1—linker—antigen-specific targeting region 2—extracellular spacer domain—transmembrane domain—co-stimulatory domain—intracellular signaling domain. In an embodiment, such a CAR may comprise two or more co-stimulatory domains.

Alternatively, the polynucleotide sequence encoding the CAR may be in the following configuration in the N-terminal to C-terminal direction: N-terminal signal sequence—antigen-specific targeting region 1—linker antigen-specific targeting region 2—transmembrane domain—co-stimulatory domain—intracellular signaling domain. In an embodiment, such a CAR may comprise two or more co-stimulatory domains.

If a CAR comprises more than two antigen-specific targeting regions, the polynucleotide sequence encoding the CAR may be in the following configuration in the N-terminal to C-terminal direction: N-terminal signal sequence—antigen-specific targeting region 1—linker—antigen-specific targeting region 2—linker—(antigen-specific targeting region)$_n$—transmembrane domain—co-stimulatory domain—intracellular signaling domain. Such a CAR may further comprise an extracellular spacer domain. Each antigen-specific targeting region may be separated by a linker. In an embodiment, such a CAR may comprise two or more co-stimulatory domains.

The invention provides a nucleic acid sequence of the backbone of an exemplary CAR of the invention comprising an extracellular spacer domain, a transmembrane domain, a co-stimulatory domain and an intracellular signaling domain. Specifically, an exemplary backbone for a may CAR comprise, in the N-terminus to C-terminus orientation, IgG4hinge-CD28tm-41BB-CD3zeta, wherein the extracellular spacer domain is the IgG4 hinge region, the transmembrane domain is the transmembrane region from CD28, the co-stimulatory domain is from 4-1BB and the intracellular signaling domain is from the CD3 zeta chain (FIG. 7). At least two or more antigen-specific targeting regions may be inserted N-terminal to the IgG4 hinge.

The invention provides nucleic acid sequences of an exemplary embodiment of the invention where the CAR is specific to CD19 and CD20. In one embodiment, the sequence encoding a bispecific anti-CD19×CD20 CAR is set forth in FIG. 3. FIG. 8 or FIG. 10. In another embodiment, the sequence encoding a bispecific anti-CD19×CD20 CAR is set forth in FIG. 4, FIG. 9 or FIG. 11. In this exemplary embodiment, the bispecific CAR comprises says specific for CD19 and CD20 with each scFv separated by a linker, joined to an extracellular spacer domain, which is joined to the co-stimulatory and intracellular signaling domains via a transmembrane domain. Although the exemplary CAR depicts a set of scFv sequences, any scFv specific for CD19 and CD20 may be used. In a particular embodiment, the bispecific CAR specific for CD19 and CD20 is CD19scFv- Gly4Serlinker-CD20scFv-IgG4-Hinge-CD28tm-41BB (cyto)-zeta(cyto) and is encoded by the sequences set forth in FIG. 3 and FIG. 4. This bispecific CAR comprises single chain Fv fragments specific for CD19 and CD20 linked by a Gly4Ser linker, an IgG4 hinge extracellular spacer domain, a CD28 transmembrane domain, a 41BB costimulatory domain and the cytoplasmic domain from CD3 zeta chain.

In another embodiment, the bispecific CAR specific for CD19 and CD20 comprises CD19scFv-Gly4serlinker-CD20scFv-huIgG4-hingeCH2CH3-CD28tm/cyto-41BB-zeta (FIG. 9-FIG. 10). This bispecific CAR comprises single chain Fv fragments specific for CD19 and CD20 linked by a Gly4Ser linker, a human IgG4 hinge, CH2 and CH3 extracellular spacer domain, a CD28 transmembrane domain, a 4-1BB costimulatory domain and the cytoplasmic domain from CD3 zeta chain.

In a further embodiment, the bispecific CAR specific for CD19 and CD20 is CD19-Gly4serlinker-CD20scFv-CD8αhinge-CD8α TM-41BBcostim-zetacyto (FIG. 11-FIG. 12). This bispecific CAR comprises single chain Fv fragments specific for CD19 and CD20 linked by a Gly4Ser linker, a CD8alpha hinge extracellular spacer domain, a CD8alpha transmembrane domain, a 41BB costimulatory domain and the cytoplasmic domain from CD3 zeta chain.

Truncated Epidermal Growth Factor Receptor (EGFRt)

Human epidermal growth factor receptor (huEGFR) (EGFR; ErbB-1, HER1 in humans) is a receptor tyrosine kinase of the ErbB family of growth factor receptors that is not expressed by cells of the hematopoietic and lymphopoietic systems. Ligand (EGF, TGF-α) binding occurs within N-terminal extracellular domains I and II of EGFR resulting from transition of receptor tyrosine kinase inactive monomers to active homodimers.

Extracellular domain III of EGFR contains the binding sites of antibodies (for example cetuximab (ERBITUX®), an IgG1 chimeric antibody). It is believed that human EGFR may be rendered incapable of binding ligands (EGF, TGF-α) by removal of domains I and II, and devoid of signaling activity by deletion of its cytoplasmic tail, while retaining an intact antibody binding site (for example cetuximab binding site), for example in extracellular domain III, IV or a combination thereof (Wang et al., A transgene-encoded cell surface polypeptide for selection, in vivo tracking, and ablation of engineered cells *Blood* 118(5)1255-1263).

A truncated EGFRt polypeptide described herein has at least three uses for genetic engineering of cell-based therapies: ex vivo cell purification, in vivo cell tracking, and cell ablation. In an embodiment, EGFRt, for use as a therapeutic control with the CARs of the invention, binds any one or more of EGFR-specific siRNA, a small molecule that targets EGFR, an anti-EGFR-antibody or a combination thereof. In another embodiment, EGFRt comprises the sequence set forth in FIG. 12 or FIG. 13 or sequences that are about 70%, about 75%, about 80%, about 85%, about 90% or about 95% homologous to the sequences set forth in FIG. 12 or FIG. 13.

In an embodiment of the invention, huEGFRt may be co-expressed with the CARs of the invention so as to purify cells expressing the CARs (for example ex vivo cell purification), track cells (for example in vitro or in vivo cell tracking) expressing the CARs or regulate cells (for example in vivo or in vitro or ex vivo) expressing the CARs by triggering cell ablation as required. In one embodiment, the CARs are bispecific CARs.

Chimeric Cytokine Receptor (CCR)

Based on the limitations of using exogenous γc cytokines in adoptive immunotherapy, the invention provides T cells with an intrinsic γc cytokine signaling mechanism. The utility of forced constitutive chimeric cytokine receptors IL-2/IL-15Rβ (CγCR2) and IL-7Rα (CγCR7) receptor signals were compared. As described below, the chimeric cytokine receptors have the ability to improve the survival, persistence, and in vivo engraftment of cytotoxic T cells (CTLs).

Accordingly, in an embodiment of the invention, the CARs of the invention may be co-expressed with CCR. For example, a bispecific CAR may be co-expressed with EGFRt and CCR. Alternately, a bispecific CAR may be co-expressed with CCR. Examples of chimeric cytokine receptor include but are not limited to IL-7 cytokine-linker-IL7Rα, IL-7 cytokine-linker-extracellular domain of IL-7Rα-transmembrane domain of IL-7Rα-cytoplasmic domain of IL-2Rβ, IL-7 cytokine-linker-IL2Rβ.

A CCR comprising IL-7 cytokine-linker-IL7Rα comprises an N-terminal signal sequence joined to the N-terminus of the IL-7 cytokine which is linked via a linker to extracellular, transmembrane and cytoplasmic domains of IL-7Rα (the alpha chain of the IL-7 receptor).

A CCR comprising IL-7 cytokine-linker-extracellular domain of IL-7Rα-transmembrane domain of IL-7Rα-cytoplasmic domain of IL-2Rβ comprises an N-terminal signal sequence joined to the N-terminus of the IL-7 cytokine which is linked via a linker to the extracellular domain and transmembrane domain of IL-7Rα and to the cytoplasmic domain of IL-2Rβ (the beta chain of the IL-2 receptor).

A CCR comprising IL-7 cytokine-linker-IL2Rβ comprises N-terminal signal sequence joined to the N-terminus of the IL-7 cytokine which is linked via a linker to extracellular, transmembrane and cytoplasmic domains of IL-2Rβ.

Dihydroxyfolate Receptor (DHFR)

Genetic modification of T cells to co-express a therapeutic transgene and a drug resistant transgene that confers resistance to lymphotoxic drugs provides the opportunity to select for therapeutic cells both in vivo and ex vivo. A mutated human enzyme transgene, dihydrofolate reductase double mutant (DHFR$^{FS}$; L22F, F31S), which confers resistance of engineered T cells to methotrexate (MTX), allowing selection of cells co-expressing a CD19-specific chimeric antigen receptor (CD19CAR) that specifically targets B-lineage tumor cells.

In an embodiment, the CARs of the invention (for example bispecific CARs) may be co-expressed with DHFR (for example mutant DHFR). In a further embodiment, the bispecific CAR may be co-expressed with EGFRt, CCR and DHFR (including mutant DHFR). Alternately, the bispecific CAR may be co-expressed with EGFRt and DHFR (including mutant DHFR).

Other selection markers that may be used with the CARs of the invention include but are not limited to methylated-DNA-protein-cysteine methyltransferase (MDMT), inosine monophosphate dehydrogenase II (IMDHP2) or a combination thereof. MDMT makes cells resistant to chemotherapy and therefore may be used if synergy between chemotherapy and T cell therapy is desired.

Vectors encoding the CARs of the invention are also provided herein. Vectors encoding CARs also encode EGFRt. In some embodiments, vectors encoding CARs and EGFRt also encode CCR or DHFR (for example mutant DHFR). In other embodiments, vectors encoding CARs and EGFRt also encode CCD and DHFR (for example mutant DHFR). In some specific embodiments, the vectors may encode a bispecific CAR and EGFRt, a bispecific CAR and EGFRt and CCR, a bispecific CAR and EGFRt and DHFR (for example mutant DHFR) or a bispecific CAR and EGFRt and CCR and DHFR (for example mutant DHFR). Vectors which may be used to express the CARs of the invention include but are not limited to lentivirus vectors, gamma retrovirus vectors, foamy virus vectors, AAV vectors, adeno virus vectors, engineered hybrid viruses, naked DNA (including but not limited to transposon mediated vectors, such as Sleeping Beauty, Piggybak, and Integrases such as Phi31.

Figure 5:
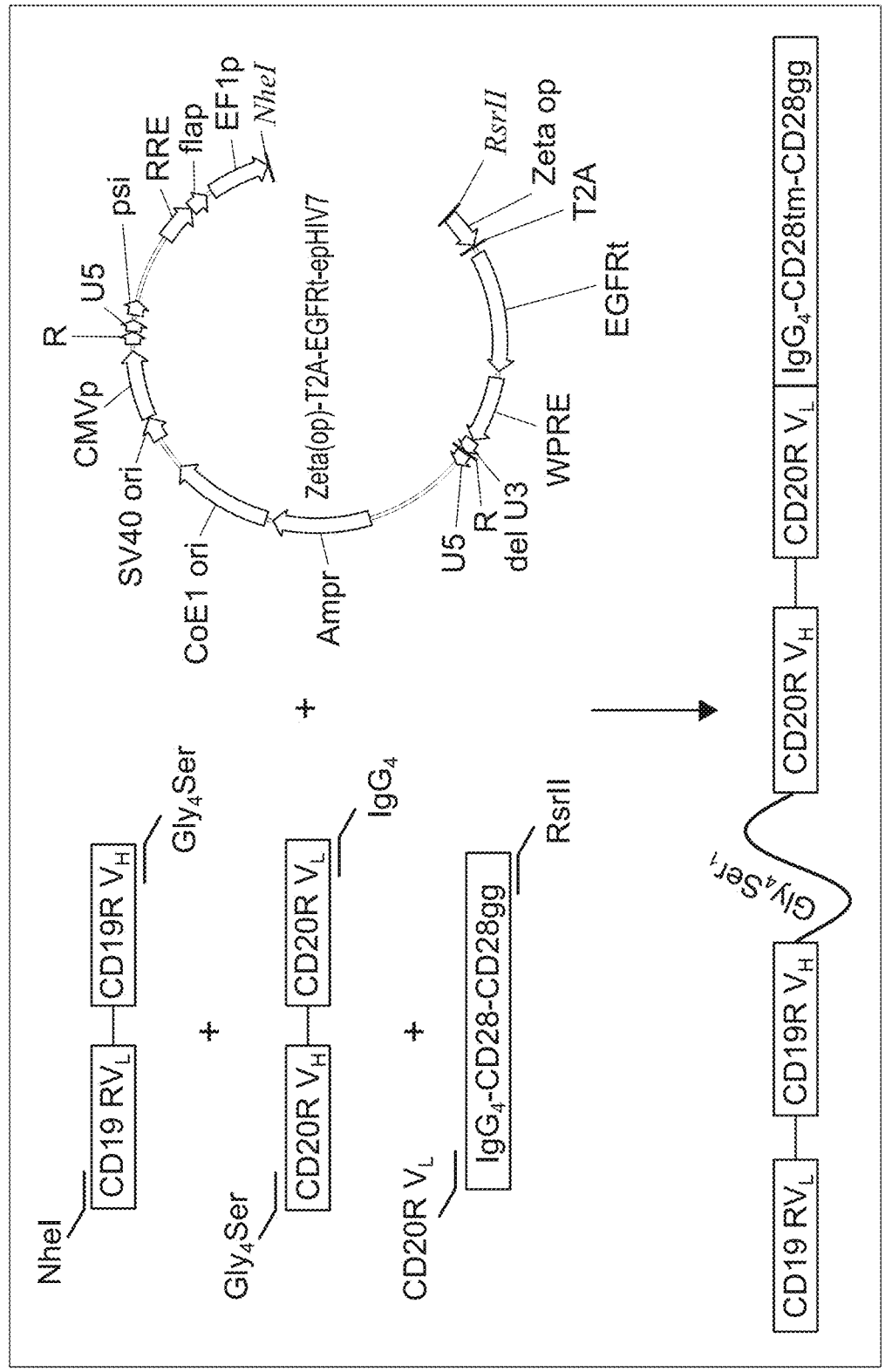
FIG. 5 depicts, in accordance with an embodiment of the present invention, a CD19scFv-Gly4Ser1linker-CD20scFv-IgG4hinge-CD28tm-CD28gg-CD3Zeta transgene construct.
Figure 6A:
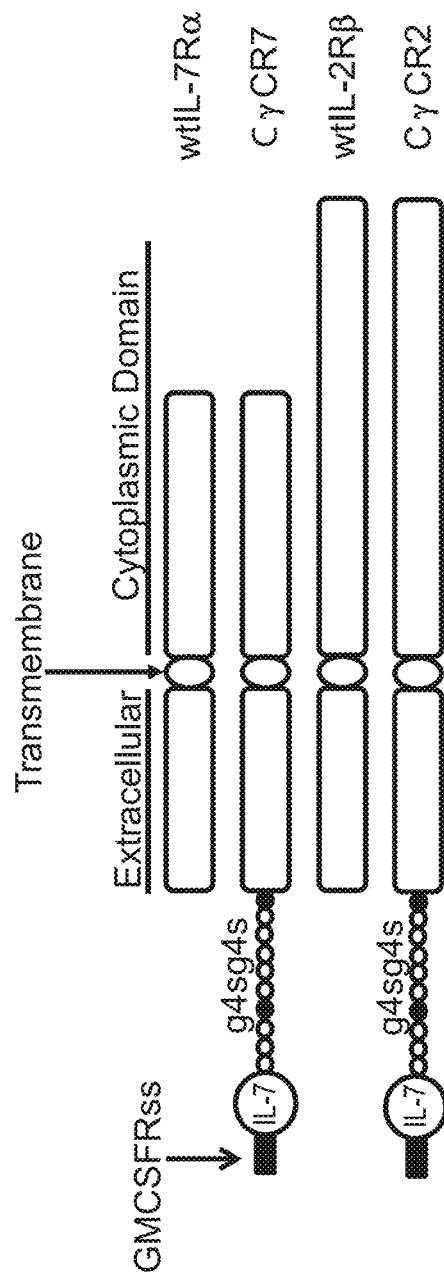
FIGS. 6A and 6B depict, in accordance with an embodiment of the present invention, development of a CγCR platform to support exogenous γc independent growth.
Figure 6B:
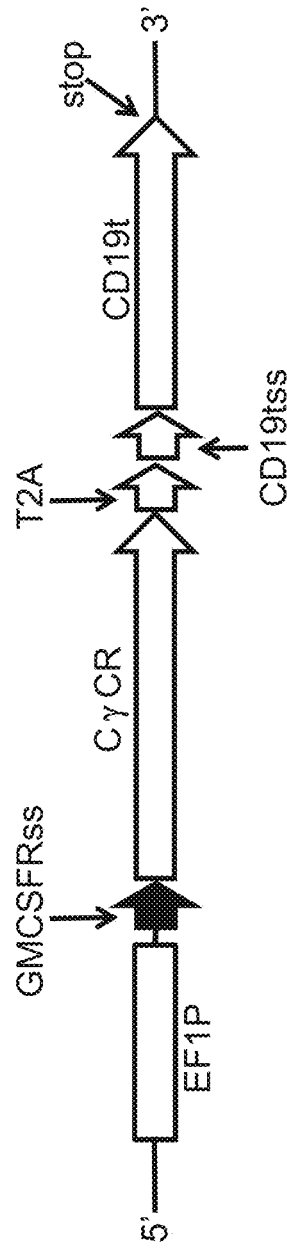

In an exemplary embodiment of the invention, the bispecific CAR specific to CD19 and CD20 disclosed herein is expressed via a lentiviral vector as illustrated in FIG. 5.

Genetically Engineered Cells of the Invention

The invention also provides genetically engineered cells which comprise and stably express the CAR of the invention. The CAR expressed by the genetically engineered cell may comprise at least two antigen-specific targeting regions, an extracellular domain, a transmembrane domain, one or more co-stimulatory domains and an intracellular signaling domain. The polynucleotide sequence encoding the CAR may also comprise an N-terminal signal sequence. In an embodiment, the CAR is a bispecific CAR. Each of the at least two antigen-specific targeting regions, extracellular spacer domain, transmembrane domain, one or more co-stimulatory domains and an intracellular signaling domain are described above. The antigen-specific targeting domains may be capable of specifically binding, in an MHC unrestricted manner, an antigen which is not normally bound by a T-cell receptor in that manner.

In an embodiment, the genetically engineered cells that express the CARs (for example bispecific CARs) of the invention co-express EGFRt. In a further embodiment, the genetically engineered cells that express the CARs (for example bispecific CARs) co-express EGFRt and CCR. In an additional embodiment, the genetically engineered cells that express the CARs (for example bispecific CARs) co-express EGFRt and DHFR (for example mutant DHFR). In another embodiment, the genetically engineered cells that express the CARs (for example bispecific CARs) co-express EGFRt, CCR and DHFR (for example mutant DHFR).

The genetically engineered cells express a CAR having at least two antigen-specific targeting regions which are specific for at least two different target antigens. In one embodiment, the antigen-specific targeting regions comprise target-specific antibodies or functional equivalents or fragments or derivatives thereof. The antigen-specific antibody may be the Fab fragment of the antibody or the single chain variable fragment (scFv) of the antibody.

Genetically engineered cells which may comprise and express the CARs of the invention include, but are not limited to, T-lymphocytes (T-cells), naïve T cells ($T_N$), memory T cells (for example, central memory T cells ($T_{CM}$), effector memory cells ($T_{EM}$)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone. CD4+ T-cells of the invention may produce IL-2, IFNγ, INFα and other T-cell effector cytokines when co-cultured in vitro with cells expressing the target antigens (for example CD20+ and/or CD19+ tumor cells). CD8$^+$ T-cells of the invention may lyse antigen-specific target cells when co-cultured in vitro with the target cells. In some embodiments, T cells may be any one or more of CD45RA$^+$ CD62L$^+$ naïve cells, CD45RO$^+$ CD62L$^+$ central memory cells, CD62L$^-$ effector memory cells or a combination thereof (Berger et al., Adoptive transfer of virus-specific and tumor-specific T cell immunity. *Curr Opin Immunol* 2009 21 (2) 224-232).

Genetically modified cells may be produced by stably transfecting cells with DNA encoding the CAR of the invention. DNA encoding the CAR of the invention (for example bispecific CAR) may also encode EGFRt, CCR and/or DHFR (for example mutant DHFR). In one embodiment, a first polynucleotide encodes the CAR (for example bispecific CAR) and is linked via IRES sequences or a polynucleotide that encodes a cleavable linker, to a second polynucleotide that encodes EGFRt. In another embodiment, the first polynucleotide encodes the CAR (for example bispecific CAR) and is linked via IRES sequences or a polynucleotide that encodes a cleavable linker, to a second polynucleotide that encodes EGFRt and the first or second polynucleotides are linked to a third polynucleotide that encodes CCR or DHFR (for example mutant DHFR), also via IRES sequences or a polynucleotide that encodes a cleavable linker. In a further embodiment, the first polynucleotide encodes the CAR (for example bispecific CAR) and is linked via IRES sequences or a polynucleotide that encodes a cleavable linker, to a second polynucleotide that encodes EGFRt and the first and second polynucleotides are linked to a third polynucleotide that encodes CCR and a fourth polynucleotide that encodes DHFR (for example mutant DHFR) via IRES sequences or a polynucleotide that encodes a cleavable linker. Viral vectors are commonly used to carry heterologous genes into cells (e.g., T-cells). Examples of viral vectors which may be used to generate genetically modified cells include but are not limited to SIN lentiviral vectors, retroviral vectors, foamy virus vectors, adeno-associated virus (AAV) vectors and/or plasmid transposons (e.g., sleeping beauty transposon system).

Various methods produce stable transfectants which express the CARs of the invention. In one embodiment, a method of stably transfecting and re-directing cells is by electroporation using naked DNA. By using naked DNA, the time required to produce redirected cells may be significantly reduced. Additional methods to genetically engineer cells using naked DNA encoding the CAR of the invention include but are not limited to chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). The transfected cells demonstrating presence of a single integrated un-rearranged vector and expression of the CAR may be expanded ex vivo. In one embodiment, the cells selected for ex vivo expansion are CD8$^+$ and demonstrates the capacity to specifically recognize and lyse antigen-specific target cells.

Viral transduction methods may also be used to generate redirected cells which express the CAR of the invention. Cell types that may be used to generate genetically modified cells expressing the bispecific CAR of the invention include but are not limited to T-lymphocytes (T-cells), natural killer cells, hematopoietic stem cells and/or pluripotent embryonic/induced stem cells capable of giving rise to therapeutically relevant progeny.

Stimulation of the T-cells by an antigen under proper conditions results in proliferation (expansion) of the cells and/or production of IL-2. The cells comprising the CAR of the invention will expand in number in response to the binding of one or more antigens to the antigen-specific targeting regions of the CAR. The invention also provides a method of making and expanding cells expressing a CAR. The method comprises transfecting or transducing the cells with the vector expressing the CAR and stimulating the cells with cells expressing the target antigens, recombinant target antigens, or an antibody to the receptor to cause the cells to proliferate, so as to make and expand T-cells. In an embodiment, the cells may be any one or more of T-lymphocytes (T-cells), natural killer (NK) cells, hematopoietic stem cells (HSCs) or pluripotent embryonic/induced stem cells capable of giving rise to therapeutically relevant progeny.

In an exemplary embodiment, the genetically engineered cells of the invention express a bispecific CAR which is specific for CD19 and CD20 antigens. In a further embodiment, a genetically engineered T-cell expresses the bispecific CARs CD19scFv-Gly4ser-linker-CD20scFv-huIgG4-hinge-CD28-41BB(cyto)-zeta(cyto) or CD19scFv-Gly4ser-linker-CD20scFv-huIgG4-hingeCH2CH3-CD28tm/cyto-zeta or CD19-Gly4serlinker-CD20scFv-CD8alphahinge-CD8alphaTM-41BBcostim-zetacyto.

In an exemplary embodiment, the invention provides a method of making and expanding T-cells expressing a CD19-specific and CD20-specific CAR. The method comprises using a lentivirus to transduce CD3×CD28 bead-stimulated purified central memory T-cells (such as T-cells from peripheral blood) with the vector expressing the CD19 and CD20 bispecific CAR, growing the T-cells in the presence of rhuIL-2 and/or IL-15 and restimulating the T-cells with $CD19^+$ and $CD20^+$ cells, recombinant CD19 and CD20, or an antibody to the receptor to cause the T-cells to proliferate, so as to make and expand CD19-specific and CD20-specific T-cells.

Therapeutic Methods of the Invention

The CARs of the invention may be used to overcome therapeutic failures arising from antigen loss escape variants, to reduce resistance to existing therapies and/or to treat diseases associated with the antigens targeted by the CARs.

Accordingly, the invention also provides methods for treating a disease associated with the antigen targeted by the CAR of the invention in a subject in need thereof. The method comprises providing a composition comprising the CAR of the invention and administering an effective amount of the composition so as to treat the disease associated with the antigen in the subject.

The invention also provides methods for overcoming therapeutic failures arising from antigen loss escape variants in disease states (e.g., B-cell diseases) in subjects in need thereof. The method comprises providing a composition comprising the CAR of the invention and administering an effective amount of the composition so as to treat the disease associated with the antigen in the subject.

In some embodiments, the composition comprises a polynucleotide encoding the CAR, a protein comprising the CAR or genetically modified cells comprising the CAR. In another embodiment, the genetically modified cells of the composition are T-lymphocytes (T-cells), naïve T cells ($T_N$), memory T cells (for example, central memory T cells ($T_{CM}$), effector memory cells ($T_{EM}$), natural killer (NK) cells, hematopoietic stem cells (HSCs) or pluripotent embryonic/ induced stem cells capable of giving rise to therapeutically relevant progeny, which express the CAR of the invention. The compositions of the invention may be administered alone or in conjunction with existing therapies. If other therapies are used in conjunction, the compositions of the invention may be administered concurrently or sequentially with the other the existing therapies.

Pharmaceutical Compositions

In various embodiments, the present invention provides pharmaceutical compositions comprising a pharmaceutically acceptable excipient and a therapeutically effective amount of the CAR (for example, bispecific CAR) of the invention. The CAR of the invention in the composition may be any one or more of a polynucleotide encoding the CAR, a protein comprising the CAR or genetically modified cells comprising the CAR. The composition may further comprise polynucleotides encoding EGFRt, CCR and/or DHFR (for example mutant DHFR), proteins co-expressed with the CAR including EGFRt, CCR and/or DHFR or genetically modified cells that express the CAR and co-express EGFRt, CCR and/or DHFR. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, intravenous, intramuscular, intraperitoneal, inhalation, transmucosal, transdermal, parenteral, implantable pump, continuous infusion, topical application, capsules and/or injections.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carder is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

FIG. 1 is a schematic representation of the bispecific chimeric antigen receptor of the invention. In an exemplary embodiment of the invention, FIGS. 2A and 2B depict the components of bispecific anti-CD19×anti-CD20 bispecific CAR. FIGS. 2A and 2B also depict a schematic of the complete cDNA packaged into epHIV-7 lentivirus vector transfer plasmid. FIG. 3 and FIG. 4 show the nucleic and amino acid sequences of an exemplary bispecific CAR, namely GMCSFss-CD19scFv-Gly4Ser1linker-CD20scFv-IgG4Hinge-CD28tm-41BBzeta-T2A-EGFRt_epHIV7.

Example 2

FIG. 5 is a schematic showing the vector construct of an exemplary CAR of the invention, namely, the CD19scFv-CD20scFv-IgG4-CD28tm-CD28costim-CD3zeta transgene construct. The CD19scFv-CD20scFv-IgG4-CD28tmCD28costim-CD3zeta transgene was assembled using the one-step isothermal DNA assembly method previously described by Gibson et. al. (Enzymatic assembly of DNA molecules up to several hundred kilobases. *Nature Methods*. 2009; 6:343-345). The $V_L$ and $V_H$ domains of the CD19 scFv construct was sequenced from a CD19CAR-CD28-Zeta transgene previously described. Schmitz N, Dreger P, Glass B, Sureda A. Allogeneic transplantation in lymphoma: current status. *Haematologica*. 2007; 92 (11): 1533-1548) through polymerase chain reaction (PCR). The $V_H$ and $V_L$ domains of the CD20 scFv were assembled by spliced-overlap polymerase chain reaction using a CD20R-CD28-Zeta transgene previously described (Michael Jensen et al., CD20 is a molecular target for scFvFc:zeta receptor redirected T-cells: implications for cellular immunotherapy of $CD20^+$ malignancy. *Biology of Blood and Marrow Transplant*. 1998; 4:75-83). The $V_H$ and the $V_L$ domains of CD19 scFv and CD20 scFv were linked with an 18-residue linker peptide as previously described. The IgG4-CD28tm-CD28costim domain was sequenced using the CD19R-CD28-CD3zeta transgene by PCR. The CD3zeta-T2A-EGFRt_epHIV7 lentiviral destination vector was prepared by NheI and RsrII restriction digestion of the CD19R-CD28 portion from a CD19R-CD28-Zeta-T2A-EGFRt_epHIV7 plasmid previously described (Seitaro Terakura et al., Generation of CD19-CAR modified CD8+ T-cells derived from virus-specific central memory T-cells. *Blood*. Oct. 26, 2011). The final CD19scFv-CD20scFv-IgG4-CD28tm-CD28costim-CD3zeta construct was assembled by the one-step isothermal Gibson DNA assembly method using the restriction digested Zeta-epHIV7 destination vector and the CD19scFv, CD20scFv, and IgG4-CD28tm-CD28costim-DNA fragments with primers for each containing a 30 bp overlap at the 5' terminus.

TABLE 1

Regulatory Elements Present in the bispecific CAR epHIV-7 Transfer Plasmid

| Regulatory Element | Function |
| --- | --- |
| U5 | 5' Unique sequence |
| Psi | Packaging signal |
| RRE | Rev-responsive element |
| flap | Contains polypurine track sequence and central termination sequence to facilitate nuclear import of pre-integration complex |
| EF1p Promoter | EF1-alpha Eukaryotic Promoter sequence driving expression of CD19xCD20 CAR |
| WPRE | Woodchuck hepatitis virus derived regulatory element to enhance viral RNA transportation |
| delU3 | 3' U3 with deletion to generate SIN vector |
| R | Repeat sequence within LTR |
| U5 | 3' U5 sequence in LTR |
| $Amp^R$ | Ampicillin-resistance gene |
| CoEl ori | Replication origin of plasmid |
| SV40 ori | Replication origin of SV40 |
| CMV promoter | CMV promoter to generate viral genome RNA |
| R | Repeat sequence within LTR |

Example 3

HEK 293T-cells were transfected with anti-CD19×CD20CAR-T2A-EGFRt epHIV-7 transfer plasmid or with anti-CD20×CD19CAR-T2A-EGFRt epHIV-7 transfer plasmid. Transfected cells were stained with biotinylated anti-Fc antibodies and streptavidin PE (SA-PE) and then were subjected to flow cytometric analysis for detection of expression of the above two CARs. Both the anti-CD19×CD20 CAR and the anti-CD20×CD19 CAR were expressed on transfected HEK 293T cells.

The epHIV-7 transfer plasmid co-expressed EGFRt with the above two bispecific CARs. EGFRt co-expression was detected on the same transfected cells using a combination of biotinylated anti-EGFR antibodies/SA-PE staining and flow cytometric analysis.

Example 4

Primary human peripheral blood derived T-cells were activated with OKT3 and then were lentivirally transduced with monospecific anti-CD19 CAR, monospecific anti-CD20 CAR or bispecific anti-CD19×CD20CAR-T2A-EGFRt epHIV7 lentivirus vector. epHIV7 lentivirus vector also encoded EGFRt together with monospecific anti-CD19 CAR, monospecific anti-CD20 CAR or bispecific anti-CD19×CD20. Thus, cells expressing the CARs co-expressed EGFRt. Transfected cells were stained with biotinylated anti-EGFR antibodies and SA-PE and then were subjected to flow cytometric analysis for detection of EGFRt expression and co-expression of monospecific or bispecific CARs. Of the cells transfected with monospecific anti-CD19 CAR, 51% expressed EGFRt; of the cells transfected with monospecific anti-CD20 CAR, 38.5% expressed EGFRt; of the cells transfected with the bispecific anti-CD19×CD20 CAR, 63.8% expressed EGFRt.

T cell receptor (TCR) complex in transfected cells was also detected in the same transfected cells using FITC-conjugated anti-TCRα and anti-TCRβ antibodies staining and flow cytometric analysis.

Example 5

H9 cells were genetically modified to express CD19, or CD20, or both CD19 and CD20. Cells were stained with anti-CD19 and anti-CD20 antibodies and then were subject to flow cytometric analysis to detect the expression of CD19 and CD20. Cytometric analysis confirmed the desired expression profile of $CD19^+CD20^-$, $CD19^-CD20^+$, and $CD19^+CD20^+$ H9 cells, namely, genetically engineered H9 cells expressed CD19, or CD20, or both CD19 and CD20 thereby simulating cancer target cells, which contain antigen-negative antigen loss escape variants. As described later, these cell lines were subsequently used as target cells to stimulate CAR-expressing T-cell lines, which act as effector cells to kill target cells.

Also, endogenous levels of CD19 and CD20 expression in SUP-B15 and DHL-6 cell lines was analyzed using anti-CD19 APC and anti-CD20 PE staining and flow cytometric analysis. SUP-B15 cell line expressed high level of CD19 with low level of CD20 (thus $CD19^+CD20^-$), and DHL-16 cell line expressed high level of CD20 with low level of CD19 (thus $CD19^-CD20^+$).

Example 6

A 4-hour chromium release assay was used to measure the lysis of the target cells by the effector cells. Effector cells are primary human T-cells lentivirally transduced to express monospecific anti-CD19 CAR, monospecific anti-CD20 CAR or bispecific anti-CD19×CD20 CAR. The bispecific anti-CD19×CD20 CAR effector T-cells effectively lysed all $CD19^+CD20^-$, $CD19^-CD20^+$, and $CD19^+CD20^+$ target cells, which include $CD19^+CD20^-$ H9 cells, $CD19^-CD20^+$ H9 cells, $CD19^+CD20^+$ H9 cells and SUP-B15 cells. At effector to target ratios of 1:1, 3:1, 10:1, and 30:1, about 25%, 45%, 50% and 60%, respectively, target cells were lysed.

In contrast, monospecific CAR expressing T-cell lines fail to lyse antigen-negative antigen loss escape variants, which escaped from the monospecific CAR effector cells. The anti-CD19 CAR effector T-cells failed to lyse $CD19^-CD20^+$ targets and the anti-CD20 CAR effector T-cells failed to lyse $CD19^+CD20^-$ targets.

Example 7

Bispecific CAR-expressing CD4 enriched T-cells were activated for cytokine secretion (Interferon gamma (IFN-g, IFN-γ)) upon stimulation by $CD19^+CD20^-$, $CD19^-CD20^+$, and $CD19^+CD20^+$ target cells, which include $CD19^+CD20^-$ H9 cells, $CD19^-CD20^+$ H9 cells, $CD19^+CD20^+$ H9 cells and SUP-B15 cells. IFN-γ content was measured by cytokine bead array of culture supernatants of T-cells and target cells after 24-hours of co-culture. Activated bispecific CAR-expressing CD4 enriched T-cells secreted at least 2500 μg/ml INF-g upon stimulation by every type of target cells. In contrast, monospecific CAR expressing T-cell lines were not activated for cytokine INF-g secretion upon stimulation by antigen-negative antigen loss escape variants, which escaped from the monospecific CAR effector cells. CD19 CAR T-cells failed to secrete IGN-γ upon co-culture with $CD19^-CD20^+$ target cells and CD20 CAR T-cells failed to secrete IGN-γ upon co-culture with $CD19^+CD20^-$ target cells.

| In-vitro Stimulation Assay | |
|---|---|
| Stimulators (3 × 10^5): | |
| TM-LCL | H9 parent |
| OKT3-TM-LCL | H9 CD19R |
| SUP-B15 | H9 CD20R |
| DHL-6 | H9 CD19/20R |
| Responders (1 × 10^6 on $S_1R_2D_{17}$): | |
| CD4 enriched mock | CD8 enriched mock |
| CD4 enriched CD19R | CD8 enriched CD19R |
| CD4 enriched CD20R | CD8 enriched CD20R |
| CD4 enriched CD19/20R | CD8 enriched CD19/20R |

Cells incubated for 24 hrs, and cell free supernatant will be harvested today for BioPlex assay Example 8

The example below describes a CD19 specific chimeric antigen receptor linked to truncated epidermal growth factor receptor (EGFRt) via a T2A sequence. EGFRt may be linked to and co-expressed with other chimeric antigen receptors, for example, bispecific chimeric antigen receptors.

Applicants demonstrated the utility of such a truncated EGFR (huEGFRt) expressed by transduced T cells for immunomagnetic purification using biotinylated cetuximab, cell tracking by flow cytometry and immunohistochemistry, and in vivo cell ablation after systemic cetuximab administration. In this exemplary embodiment, domain I and II of EGFRt have been deleted while domains III and IV have been retained.

The CD19CAR-T2A-EGFRt-epHIV7 lentiviral construct contains: (1) the chimeric antigen receptor (CAR) sequence consisting of the $V_H$ and $V_L$ gene segments of the CD19-specific FMC63 monoclonal antibody (mAb), an IgG4 hinge-$C_{H2}$-$C_{H3}$, the transmembrane, and cytoplasmic signaling domains of the co-stimulatory molecule CD28, and the cytoplasmic domain of the CD3 chain (Kowolik C K et al., CD28 costimulation provided through a CD19-specific chimeric antigen receptor enhances in vivo persistence and antitumor efficacy of adoptively transferred T cells. *Cancer Res.* 2006, 66 (22):10995-11004); (2) the self-cleaving T2A sequence (Szymczak A L. et al., Correction of multi-gene deficiency in vivo using a "self-cleaving" 2A peptide-based retroviral vector. *Nat Biotechnol* 2004; 22 (5) 589-594); and (3) the truncated EGFR sequence as indicated.

Immunomagnetic Enrichment of huEGFRt+ Human T Cells after Lentiviral Transduction The biotinylated cetuximab was used for either immunomagnetic selection or FACS sorting of huEGFRt+ cells. Applicants used biotinylated cetuximab in conjunction with commercially available antibiotin microbeads for the immunomagnetic selection of human T cells transduced with a self-inactivating lentivirus that directs the co-expression of CD19CAR and huEGFRt.

PBMCs or purified central memory ($CD45RO^+CD62L^+$ $T_{CM}$) or effector memory ($CD45RO^+CD62L^+$ $T_{EM}$) T-cell subsets were stimulated with anti-CD3/anti-CD28 beads and then transduced by lentiviral vector to generate a panel of primary human T-cell lines, of which 2.6%-40% expressed huEGFRt and CAR. The unselected cells were labeled with biotinylated cetuximab and anti-biotin microbeads; and then were separated to consistently obtain a selected cell population, of which 90% express huEGFRt and CAR.

Unselected T cells and selected fraction were stained with biotinylated-cetuximab and either PE-conjugated streptavidin or PE-conjugated anti-biotin Ab, and then were subject to flow cytometric analysis. Selection of $CD19CAR^+$ $EGFRt^+$ cells was performed either 3 days after transduction of OKT3 blasts (enriched from 38% to 98%), or after 1 rapid expansion cycle of transduced effector memory $CD62LCD45RO^+$-derived cells (enriched from 20% to 96%), after 3 rapid expansion cycles of transduced CMVpp65-specific TCM-derived cells (enriched from 12% to 91%), or after 2 rapid expansion cycles of transduced $CD8^+$TCM-derived cells (enriched from 3% to 97%). Selection of $CD19CAR^+EGFRt^+IMPDH2dm^+$ cells was performed after 1 rapid expansion cycle of transduced TCM-derived cells (enriched from 25 to 92%).

CD19CAR-T2A-EGFRt-IMPDH2dm constructs contained in lentiviral vectors include codon optimized sequence portions of the CD19-specific, CD28 co-stimulatory CAR (CD19CAR), followed by the self-cleavable T2A, and selection markers huEGFRt and IMPDH2dm (a double mutant of the inosine monophosphate dehydrogenase 2 gene that allows for cell survival upon addition of mycophenolate 27), along with the Elongation Factor 1 promoter sequences (EF-1p), the GM-CSF receptor alpha chain signal sequences (GMCSFRss), and the 3 nucleotide stop codon.

Before immunomagnetic selection, a proliferative advantage of huEGFRt− cells over huEGFRt+ cells was observed in cultures of unselected transduced T cells subjected to OKT3-mediated expansion. However, after immunomagnetic selection, the level of huEGFRt expression and the frequency of expressing cells remained stable over 3 consecutive 14-day cycles of OKT3-based expansion[14]. The fold expansion of $EGFRt^+$ cells after immunomagnetic selection was significantly enhanced over that of $huEGFRt^+$ cells in the unselected cultures.

These data demonstrate that huEGFRt can serve as a cell surface marker unique to transduced human T cells and enable subsequent cetuximab-based immunomagnetic purification of stable huEGFRt-expressing cell populations which also express CARs.

Tracking of Adoptively Transferred $huEGFRt^+$ T Cells Using Flow Cytometry and Immunohistochemistry To test the utility of huEGFRt for tracking the engraftment of adoptively transferred T cells, Applicants harvested blood and bone marrow specimens from NOD/Scid $IL-2R\gamma C^{null}$ mice engrafted with $CD19CAR^+EGFRt^+$ human T cells.

First, unfixed peripheral blood and bone marrow mononuclear cell samples were subjected to flow cytometric analysis after being stained with biotinylated cetuximab and PE-conjugated streptavidin. Although the level of human $CD45^+$ T-cell engraftment (20%-25%) was similar in animals administered either huEGFRt-negative or -positive T cells, double staining for human CD45 and EGFR allowed for the resolution of $huEGFRt^+$ (ie, transgeneexpressing) human cells from their huEGFRt-negative counterparts.

Second, Applicants sought to determine whether standard paraffin embedded fixed tissue specimens were amenable to detection of $huEGFRt^+$ T-cell infiltrates using EGFR-specific diagnostic kits. Applicants performed immunohistochemical analysis of paraffin-embedded femurs from engrafted mice and detected $huEGFRt^+$ cells in the bone marrow. These data support the utility of huEGFRt to serve as a tracking marker for quantifying the frequency and tissue distribution of adoptively transferred T cells.

Cetuximab Binding to huEGFRt Sensitizes Human T Cells to ADCC

A valuable feature of a cell surface selection/tracking marker would be its capacity to serve as a target for in vivo cell ablation. Applicants evaluated the extent to which Cetuximab bound to huEGFRt on T cells activates ADCC of $huEGFRt^+$ T cells in vitro, and whether Cetuximab administration could attenuate the engraftment of adoptively transferred $huEGFRt^+$ T cells in NOD/scid mice.

$^{51}Cr$-labeled $huEGFRt^+$ T cells as the target cells and human GM-CSF activated fresh PBMCs as effectors were co-cultured. Then, the addition of Cetuximab specifically sensitized $huEGFRt^+$ T cells to ADCC cytolysis by effectors. Lysis of $huEGFRt^+$ T cells was measured by 4-hour chromium release assay and results showed that Cetuximab addition significantly increased lysis from less than 5% to about 50%, 45%, 40% and 15% respectively at effector to target (effector:target) ratios 50:1, 25:1, 5:1 and 1:1.

In contrast, the addition of the CD20-specific mAb RITUXAN® (rituximab) had no effect on triggering ADCC of huEGFRt+ T cells in this assay.

Applicants next derived $huEGFRt^+$ CTLL-2 murine T cells that were additionally modified to secrete autocrine IL-2 and express the firefly luciferase biophotonic reporter, and adoptively transferred these $ffLuc^+huEGFRt^+$ CTLL-2 cells via intravenous injection to NOD/scid mice, which subsequently received Cetuximab or RITUXAN® (rituximab). The in vivo engraftment of transferred CTLL-2, as measured by in vivo biophotonic imaging, was significantly inhibited (97%, $P<0.05$) in mice that received ERBITUX® (cetuximab) (1 mg intraperitoneally daily). The Cetuximab-mediated elimination of the $ffLuc^+huEGFRt^+$ CTLL-2 cells occurred between 4 and 6 days. These data support the use of Cetuximab administration as a therapeutic control for patients receiving $huEGFRt^+$ T cells.

Example 9

This example describes T cells with an intrinsic γc cytokine signaling mechanism, and shows that chimeric cytokine receptors (CCR) IL-2/IL-15Rβ (CγCR2) and IL-7Rα (CγCR7) have the ability to improve the survival, persistence, and in vivo engraftment of cytotoxic T cells (CTLs). Truncated CD19 antigen (CD19t) was linked to CγCR via a T2A linker to show the expression of CγCR on the cell surface. The chimeric cytokine receptors described herein may be linked to the chimeric antigen receptors of the invention, such as bispecific CARs described herein.

To develop a cell-intrinsic, ligand-independent γc cytokine platform, Applicants engineered chimeric γc cytokine receptors (CγCR) comprised of the IL-7 cytokine tethered by ten amino acids to the extracellular domain of IL-7Rα. To engineer a CγCR that confers an IL-7R signal, IL-7 cytokine was tethered to the full length IL-7Rα chain (CγCR7). A CγCR that provides an IL-2/IL-15Rβ signal was engineered by tethering the IL-7 cytokine to the extracellular and transmembrane domain of IL-7Rα fused to the cytoplasmic domain of IL-2/IL-15Rβ (CγCR2). These single chain chimeric receptors are expected to require endogenous γc chain for signaling.

Constructs were then generated Where the CγCR transgenes were followed by the self-cleavable T2A sequence, and a cytoplasmically truncated CD19 antigen (CD19t). CγCR and CD19t are expressed as a single transcript and cleaved post-translationally at the C-terminus of the T2A self-cleaving peptide to yield two separate type 1 membrane proteins CγCR(T2A) and CD19t. Based on expression of two proteins from a single transcript, the ratio of CγCR (T2A) to CD19t expression is 1:1, therefore, cell surface CD19t is an indication of CγCR cell surface expression. Lentiviral transduction and expression of these constructs could then be measured by surface CD19t expression, such as that seen in both Jurkat and NK-92 cell lines.

A third CγCR was also engineered, having IL-7 cytokine tethered to a truncated IL-7Rα (CγCR7t), which is missing amino acids 1-126 from the extracellular domain of the IL-7Rα. A molecular model of CγCR7t dimerization with the endogenous γc chain is necessary for signal transduction. The lack of amino acids 1-126 of the extracellular domain of IL-7Rα renders the CγCR7t nonfunctional.

Truncated CγCR7 expression does not functionally signal or support cytokine independent cell growth. Flow cytometric detected cell-surface CD19t on lenti-transduced Jurkat (95% CD19t$^+$CγCR7t$^+$) and Teff cell lines (97% CD19t$^+$ CγCR7t$^+$). Western blot analysis of STAT5 phosphorylation within CγCR7t expressing Jurkat cell line did not detect obvious increase of phosphorylated STAT5 as compared to non-transduced control Jurkat cell line. Positive controls OKT3 stimulated PBMC cultured in 50 U/ml IL-2 and 10 ng/ml IL-15 and K562 showed activation of increased phosphorylated STAT5. Accordingly, expansion and viability of CTLs transduced with CγCR7t cultured for 20 days were still dependent on cytokines.

To determine if functional CγCRs such as CγCR2 and CγCR7 could support the growth of CD8$^+$ human primary T cells in the absence of exogenous cytokine, we measured the expansion of CTLs expressing each CγCR. Human primary T cells expressing CγCR7t were unable to expand in the absence of exogenous cytokine. Both CγCR2 and CγCR7 were able to support the survival and proliferation of the CD8$^+$ T cells through maintenance of viability, in a manner similar to that of parental cells cultured in 5 U/ml and 0.5 U/ml IL-2, respectively. The increased total cell expansion measured for CγCR2$^+$ versus CγCR7$^+$ CTL correlates with increased expression (i.e., MPI of 26 for CγCR7 versus 52 for CγCR2) of Ki67, a nuclear antigen protein present in G1, S, G2, and M phase of the cell cycle. Higher Bcl-2, an key antiapoptotic protein induced in response to IL-2 and IL-7 signaling, expression was observed for CγCR7$^+$ versus CγCR2$^+$ CTL, supporting the ability of CγCR7 to maintain the survival of the human primary T cells. Together this data suggests that, although both CγCRs support cytokine-independent T cell viability and expansion, CγCR2 provides a proliferative advantage while CγCR7 maintains survival for effector CD8$^+$ CTLs.

CγCR Expressing CD8$^+$ T Cells Exhibit Cytokine Independent Engraftment In Vivo Studies by our lab and others indicate that human CTL engraftment in NOD/Scid IL-2RγC$^{null}$ mice is dependent on exogenous administration of human IL-15 or IL-2. To test the potential of CγCR expression in CTLs to overcome this dependence, parental effector T cells, CγCR7$^+$ CTLs, and CγCR2$^+$ CTLs were injected into the tail vein of immunodeficient NOD/Scid IL-2RγC$^{null}$ mice in the absence of exogenous cytokine administration. Total engraftment was compared by harvesting at least four mice per group at day 8, 17, 24, and 48 and analyzing T cell levels in the blood and bone marrow.

In the blood, CγCR2$^+$ CTLs had impressive significant (P<0.007) exogenous cytokine independent engraftment compared to CγCR7$^+$ CTLs and the parental cells. In the bone marrow, both CγCR7$^+$ CTLs (P<0.03) and CγCR2$^+$ CTLs (P<0.0005) had significant exogenous cytokine independent engraftment compared to the parental cells. CγCR2$^+$ CTLs had higher engraftment compared to CγCR7$^+$ CTLs. This indicates that both CγCR7$^+$ CTLs and CγCR2$^+$ CTLs are capable of supporting exogenous cytokine independent engraftment but the total percentage of cells was different. The blood supported higher percent engraftment of CγCR2$^+$ CTLs compared to bone marrow. The bone marrow supported the engraftment of CγCR7$^+$ CTLs over a longer period of time. Importantly, the engraftment was not infinite as the cells were no longer present in the blood and bone marrow at day 48 in either group.

Cell intrinsic γc cytokine signals can replace the need for exogenous cytokine administration for the support of adoptively transferred CTLs. Providing cell intrinsic cytokine receptors can overcome the major limitation of adoptive immunotherapy; the long-term persistence of adoptively transferred CTL. This may eliminate the need for administration of exogenous cytokine, which may reduce toxicities and bystander effects on endogenous cell types.

Example 10

This example shows that CD19 chimeric antigen receptor linked to EGFRt and DHFR can be regulated by methotrexate. Using the methods described herein, the dihydroxyfolate receptor described herein may be linked to the bispecific chimeric antigen receptors of the invention.

Applicants developed a human selectable transgene using a variant of human dihydrofolate reductase (hDHFR) that would enable selection of T cells with the less toxic, pharmaceutically available drug methotrexate (MTX). MTX exerts its anti-proliferative effect through competitive inhibition of DHFR, a key enzyme essential for de nova synthesis of thymidylate nucleotides.

In the instant example, Applicants evaluated the potential of DHFR$^{FS}$ (hDHFR L22F/F31S variant) mediated in vitro selection of primary human T cells that co-express a CD19-specific chimeric antigen receptor (CD19CAR for targeting of CD19-expressing tumors). In this strategy, we hypothesized that exposure of a transduced mixed population of T cells to the lymphotoxic drug MTX should lead to elimination of untransduced T cells and selective expansion of DHFR$^{FS}$/CD19CAR T cells co-expressing T cells, increasing the anti-tumor efficacy of the T cell population as a whole. Here Applicants show that DHFR$^{FS}$-mediated selection of gene modified T cells enforced the CD19CAR therapeutic transgene expression, and allowed for the derivation of CAR$^+$ stable integrants in the presence of clinically attainable concentrations of MTX (e.g., 0.1 µM MTX).

To translate the hDHFR$^{FS}$ selection approach for potential therapeutic utility, Applicants designed a lentiviral vector co-expressing hDHFR$^{FS}$ in conjunction with a CD19-specific chimeric antigen receptor (CD19CAR) and a truncated human EGFR polypeptide as a tracking marker (huEGFRt) each separated by a ribosomal skip T2A sequence.

CTLL2 T cells were first transduced with this CD19CAR-huEGFRt-hDHFR$^{FS}$ lentiviral vector and evaluated for their resistance to MTX. Ten days after lenti-transduction, 7-8% of the cells were positive for CD19CAR and huEGFRt expression.

In the absence of MTX, the non-transduced and transduced CTLL2 cells expanded at an equivalent rate (21- and 27-fold respectively). After incubation with MTX (0-0.1 µM) for 8 days, a 7-fold expansion with 80% survival was observed with transduced cells, while exposure of non-transduced CTLL2 cells to ≥0.05 µM MTX resulted in strong inhibition of non-transduced CTLL2 cell expansion and viability.

Evaluation of huEGFRt expression levels of transduced CTLL2 cells after 8 days in culture with varying concentrations of MTX further revealed significant MTX-mediated enrichment of transgene-expressing huEGFRt$^+$ cells (49%, 93%, 98.5%, 99% at 0.01, 0.025, 0.05 and 0.1 µM MIX respectively).

To further characterize the maximum dose of MTX that could be tolerated by selected CTLL2 cells, transduced CTLL2 cells that had been cultured in 0.1 µM MTX for 8 days were re-plated at a wider range of MTX concentrations (up to 0.75 µM). These transduced and pre-MTX selected cells were able to expand 90-100 fold at MTX concentrations up to 0.25 µM, which is equivalent to non-transduced control CTLL2 expansion in the absence of MTX.

Applicants transduced primary human T cells with the same CD19CAR-huEGFRt-hDHFR$^{FS}$ lentiviral vector. Purified CD62L$^+$CD45RO$^+$ T cells were used as a starting population based on their potential for persistence after adoptive transfer. Ten days after transduction, these T cells were cultured in varying concentrations of MTX and assessed for cell number and viability over time. After 10 days, transduced and non-transduced T cells expanded equally (80-fold) in the absence of MTX. Furthermore, even at 0.1 µM MTX, transduced T cells maintained a viability of 63%, while non-transduced primary human T cells exhibited strong inhibition of both viability and fold-expansion starting at concentrations as low as 0.025 µM MTX.

Flow cytometric evaluation of transduced T cells after 10 days in culture with varying concentrations of MTX revealed significant MTX-mediated enrichment of transgene-expressing cells (e.g., 0.025 µM MTX enriched about 54% CD19CAR$^+$ and 79% EGFRt$^+$; 0.05 µM MTX enriched about 76% CD19CAR$^+$ and 89% EGFRt$^+$)

Comparison of CD19CAR and EGFRt expression at day 6 vs. day 10 of culture revealed the steady progression of this MTX/DHFR$^{FS}$-mediated selection over time (Day 0: 18% CD19CAR$^+$, 28% EGFRt$^+$; Day 6: 48% CD19CAR$^+$, 71% EGFRt$^+$; Day 10: 70% CD19CAR$^+$, 88% EGFRt$^+$).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A polynucleotide, which encodes a bispecific chimeric antigen receptor, comprising
   a. a nucleic acid sequence encoding at least two antigen-specific targeting regions, each antigen-specific targeting region comprising a single-domain antibody;
   b. a nucleic acid sequence encoding an extracellular spacer domain;
   c. a nucleic acid sequence encoding a transmembrane domain;
   d. a nucleic acid sequence encoding at least one co-stimulatory domain; and
   e. a nucleic acid sequence encoding an intracellular signaling domain.

2. The polynucleotide of claim 1, wherein the nucleic acid sequence encoding at least two antigen-specific targeting regions encodes at least two antigen-specific targeting regions which bind (i) CD19 and CD20, (ii) CD20 and L1-CAM, (iii) L1-CAM and GD2, (iv) EGFR and L1-CAM, (v) CD19 and CD22, (vi) EGFR and C-MET, (vii) EGFR and HER2, (viii) C-MET and HER2, or (ix) EGFR and ROR1;
   the nucleic acid sequence encoding an extracellular spacer domain encodes an extracellular space that comprises any one or more of an Fc fragment of an antibody, a hinge region of an antibody, a constant domain of heavy chain CH2 region of an antibody, a CH3 region of an antibody, and combinations thereof;
   the nucleic acid sequence encoding a transmembrane domain encodes a transmembrane domain that comprises any one or more of a transmembrane domain of a zeta chain of a T cell receptor complex, CD28, CD8a, and combinations thereof;
   the nucleic acid sequence encoding at least one co-stimulatory domain encodes at least one co-stimulatory domain that comprises a signaling domain from any one or more of CD28, CD137 (4-1BB), CD134 (OX40), Dap10, CD27, CD2, CD5, intercellular adhesion molecule 1 (ICAM-1), lymphocyte function-associated antigen 1 (LFA-1), Lck, tumor necrosis factor receptor type I (TNFR-I), TNFR-II, Fas, CD30, CD40 and combinations thereof;
   and the nucleic acid sequence encoding intracellular signaling domain encodes an intracellular signaling domain that comprises a signaling domain of one or more of a human CD3 zeta chain, FcγRIII, FcεRI, a cytoplasmic tail of a Fc receptor, an immunoreceptor tyrosine-based activation motif (ITAM) bearing cytoplasmic receptors, and combinations thereof.

3. The polynucleotide of claim 1, wherein the polynucleotide further comprises a nucleic acid sequence encoding a therapeutic control, and the therapeutic control comprises any one or more of: truncated epidermal growth factor receptor (EGFRt), thymidine kinase, cytosine deaminase, nitroreductase, xanthine-guanine phosphoribosyl transferase, human caspase 8, human caspase 9, purine nucleoside phosphorylase, linamarase/linamarin/glucose oxidase, deoxyribonucleoside kinase, horseradish peroxidase (HRP)/indole-3-acetic (IAA), gamma-glutamylcysteine synthetase, CD20/alphaCD20, CD34/thymidine kinase chimera, dox-depedent caspase-2, mutant thymidine kinase (HSV-TKSR39), AP1903/Fas system, a chimeric cytokine receptor (CCR), and a selection marker.

4. A vector comprising the polynucleotide of claim 1.

5. A virus comprising the polynucleotide of claim 1.

6. The virus of claim 5, wherein the virus is an RNA virus.

7. The virus of claim 5, wherein the virus is a retrovirus, an adenovirus, an adeno-associated virus, a lentivirus, a pox virus or a herpes virus.

8. A genetically engineered cell, comprising the polynucleotide of claim 1, a chimeric antigen receptor encoded by the polynucleotide of claim 1, or a combination of a bispecific chimeric antigen receptor and a therapeutic control as encoded by the polynucleotide of claim 1.

9. The genetically engineered cell of claim 8, wherein the cell is a T-lymphocyte (T-cell).

10. The genetically engineered cell of claim 9, wherein the cell is a nave T-cell, a central memory T-cell, an effector memory T-cell, or a combination thereof.

11. The genetically engineered cell of claim 8, wherein the cell is a natural killer (NK) cell, a hematopoietic stem cell (HSC), an embryonic stem cell, or a pluripotent stem cell.

12. A polynucleotide, which encodes a bispecific chimeric antigen receptor, comprising:
   a. a nucleic acid sequence encoding at least two antigen-specific targeting regions, each antigen-specific targeting region comprising a single-domain antibody and binding a different antigen;
   b. a nucleic acid sequence encoding an extracellular spacer domain;
   c. a nucleic acid sequence encoding a transmembrane domain;
   d. a nucleic acid sequence encoding at least one co-stimulatory domain; and
   e. a nucleic acid sequence encoding an intracellular signaling domain.

13. A vector comprising the polynucleotide of claim 12.

14. A virus comprising the polynucleotide of claim 12.

15. The virus of claim 14, wherein the virus is an RNA virus.

16. The virus of claim 14, wherein the virus is a retrovirus, an adenovirus, an adeno-associated virus, a lentivirus, a pox virus or a herpes virus.

17. A genetically engineered cell, comprising the polynucleotide of claim 12 or a chimeric antigen receptor encoded by the polynucleotide of claim 12.

18. The genetically engineered cell of claim 17, wherein the cell is a T-lymphocyte (T-cell).

19. The genetically engineered cell of claim 18, wherein the cell is a nave T-cell, a central memory T-cell, an effector memory T-cell, or a combination thereof.

20. The genetically engineered cell of claim 17, wherein the cell is a natural killer (NK) cell, a hematopoietic stem cell (HSC), an embryonic stem cell, or a pluripotent stem cell.

21. The polynucleotide of claim 12, wherein the polynucleotide further comprises a nucleic acid sequence encoding truncated epidermal growth factor receptor (EGFRt).

22. The genetically engineered cell of claim 17, wherein the cell further comprises truncated epidermal growth factor receptor (EGFRt) or a nucleic acid sequence encoding the EGFRt.

\* \* \* \* \*

SEQUENCE LISTING

```
<160> NUMBER OF SEQ ID NOS: 15

<210> SEQ ID NO 1
<211> LENGTH: 3273
<212> TYPE: DNA
<213> ORGANISM: Artificial Sequence
<220> FEATURE:
<223> OTHER INFORMATION:
     GMCSFRss-CD19scFv-Gly4Ser1linker-CD20scFv-IgG4Hinge-CD28tm-41BB-C
     D3zeta-T2A-EGFRt_epHIV7

<400> SEQUENCE: 1
```

-continued

```
atgctgctgc tggtgaccag cctgctgctg tgcgagctgc cccacccgc ctttctgctg      60
atccccatga cccagaccac ctccagcctg agcgccagcc tgggcgaccg ggtgaccatc     120
agctgccggg ccagccagga catcagcaag tacctgaact ggtatcagca gaagcccgac     180
ggcaccgtca agctgctgat ctaccacacc agccggctgc acagcggcgt gcccagccgg     240
tttagcggca gcggctccgg caccgactac agcctgacca tctccaacct ggaacaggaa     300
gatatcgcca cctactttg ccagcagggc aacacactgc cctacacctt ggcggcgga      360
acaaagctgg aaatcaccgg cagcacctcc ggcagcggca agcctggcag cggcgagggc     420
agcaccaagg gcgaggtgaa gctgcaggaa agcggccctg gcctggtggc ccccagccag     480
agcctgagcg tgacctgcac cgtgagcggc gtgagcctgc ccgactacgg cgtgagctgg     540
atccggcagc cccccaggaa gggcctggaa tggctgggcg tgatctgggg cagcgagacc     600
acctactaca cagcgccct gaagagccgg ctgaccatca tcaaggacaa cagcaagagc     660
caggtgttcc tgaagatgaa cagcctgcag accgacgaca ccgccatcta ctactgcgcc     720
aagcactact actacggcgg cagctacgcc atggactact ggggccaggg caccagcgtg     780
accgtgagca gcggaggtgg tggatccgag gtgcagctgc agcagtctgg ggctgagctg     840
gtgaagcctg ggcctcagt gaagatgtcc tgcaaggctt ctggctacac atttaccagt     900
tacaatatgc actgggtaaa gcagacacct ggacagggcc tggaatggat tggagctatt     960
tatccaggaa atggtgatac ttcctacaat cagaagttca aaggcaaggc cacattgact    1020
gcagacaaat cctccagcac agcctacatg cagctcagca gcctgacatc tgaggactct    1080
gcggactatt actgtgcaag atctaattat tacggtagta gctactggtt cttcgatgtc    1140
tggggcgcag ggaccacggt caccgtctcc tcaggcagta ctagcggtgg tggctccggg    1200
ggcggttccg gtggggcgg cagcagcgac attgtgctga cccaatctcc agctatcctg    1260
tctgcatctc caggggagaa ggtcacaatg acttgcaggg ccagctcaag tgtaaattac    1320
atggactggt accagaagaa gccaggatcc tcccccaaac cctggattta tgccacatcc    1380
aacctggctt ctggagtccc tgctcgcttc agtggcagtg ggtctgggac ctcttactct    1440
ctcacaatca gcagagtgga ggctgaagat gctgccactt attactgcca gcagtggagt    1500
tttaatccac ccacgttcgg aggggggacc aagctggaaa taaaagagag caagtacgga    1560
ccgcccctgc cccccttgcc tatgttctgg gtgctggtgg tggtcggagg cgtgctggcc    1620
tgctacagcc tgctggtcac cgtggccttc atcatctttt gggtgaaacg gggcagaaag    1680
aaactcctgt atatattcaa caaccatttt atgagaccag tacaaactac tcaagaggaa    1740
gatggctgta gctgccgatt ccagaagaa gaagaaggag gatgtgaact gcgggtgaag    1800
ttcagcagaa gcgccgacgc ccctgcctac cagcagggcc agaatcagct gtacaacgag    1860
ctgaacctgg gcagaaggga gagtacgac gtcctggata gcggagagg ccgggaccct     1920
gagatgggcg gcaagcctcg gcggaagaac ccccaggaag gcctgtataa cgaactgcag    1980
aaagacaaga tggccgaggc ctacagcgag atcggcatga agggcgagcg gaggcggggc    2040
aagggccacg acggcctgta tcagggcctg tccaccgcca ccaaggatac ctacgacgcc    2100
ctgcacatgc aggccctgcc cccaaggctc gagggcggcg gagagggcag aggaagtctt    2160
ctaacatgcg gtgacgtgga ggagaatccc ggccctagga tgcttctcct ggtgacaagc    2220
cttctgctct gtgagttacc acacccagca ttcctcctga tcccacgcaa agtgtgtaac    2280
ggaataggta ttggtgaatt taaagactca ctctccataa atgctacgaa tattaaacac    2340
```

-continued

```
ttcaaaaact gcacctccat cagtggcgat ctccacatcc tgccggtggc atttaggggt    2400
gactccttca cacatactcc tcctctggat ccacaggaac tggatattct gaaaaccgta    2460
aaggaaatca cagggttttt gctgattcag gcttggcctg aaaacaggac ggacctccat    2520
gcctttgaga acctagaaat catacgcggc aggaccaagc aacatggtca gttttctctt    2580
gcagtcgtca gcctgaacat aacatccttg ggattacgct ccctcaagga gataagtgat    2640
ggagatgtga taatttcagg aaacaaaaat ttgtgctatg caaatacaat aaactggaaa    2700
aaactgtttg gacctccgg tcagaaaacc aaaattataa gcaacagagg tgaaaacagc    2760
tgcaaggcca caggccaggt ctgccatgcc ttgtgctccc ccgagggctg ctggggcccg    2820
gagcccaggg actgcgtctc ttgccggaat gtcagccgag gcagggaatg cgtggacaag    2880
tgcaaccttc tggagggtga gccaaggag tttgtggaga actctgagtg catacagtgc    2940
cacccagagt gcctgcctca ggccatgaac atccctgca caggacgggg accagacaac    3000
tgtatccagt gtgcccacta cattgacggc ccccactgcg tcaagacctg cccggcagga    3060
gtcatgggag aaaacaacac cctggtctgg aagtacgcag acgccggcca tgtgtgccac    3120
ctgtgccatc caaactgcac ctacggatgc actgggccag tcttgaagg ctgtccaacg    3180 aatgggccta agatccgtc catcgccact gggatggtgg gggcctcct cttgctgctg    3240 gtggtggccc tggggatcgg cctcttcatg tga                                3273
```

```
<210> SEQ ID NO 2
<211> LENGTH: 3273
<212> TYPE: DNA
<213> ORGANISM: Artificial Sequence
<220> FEATURE:
<223> OTHER INFORMATION:
     GMCSFRss-CD19scFv-Gly4Ser1linker-CD20scFv-IgG4Hinge-CD28tm-41BB-C
     D3zeta-T2A-EGFRt_epHIV7
<220> FEATURE:
<221> NAME/KEY: CDS
<222> LOCATION: (1)..(3273)

<400> SEQUENCE: 2 atg ctg ctg ctg gtg acc agc ctg ctg ctg tgc gag ctg ccc cac ccc        48
Met Leu Leu Leu Val Thr Ser Leu Leu Leu Cys Glu Leu Pro His Pro
1               5                   10                  15 gcc ttt ctg ctg atc ccc atg acc cag acc acc tcc agc ctg agc gcc        96
Ala Phe Leu Leu Ile Pro Met Thr Gln Thr Thr Ser Ser Leu Ser Ala
            20                  25                  30 agc ctg ggc gac cgg gtg acc atc agc tgc cgg gcc agc cag gac atc       144
Ser Leu Gly Asp Arg Val Thr Ile Ser Cys Arg Ala Ser Gln Asp Ile
        35                  40                  45 agc aag tac ctg aac tgg tat cag cag aag ccc gac ggc acc gtc aag       192
Ser Lys Tyr Leu Asn Trp Tyr Gln Gln Lys Pro Asp Gly Thr Val Lys
    50                  55                  60 ctg ctg atc tac cac acc agc cgg ctg cac agc ggc gtg ccc agc cgg       240
Leu Leu Ile Tyr His Thr Ser Arg Leu His Ser Gly Val Pro Ser Arg
65                  70                  75                  80 ttt agc ggc agc ggc tcc ggc acc gac tac agc ctg acc atc tcc aac       288
Phe Ser Gly Ser Gly Ser Gly Thr Asp Tyr Ser Leu Thr Ile Ser Asn
                85                  90                  95 ctg gaa cag gaa gat atc gcc acc tac ttt tgc cag cag ggc aac aca       336
Leu Glu Gln Glu Asp Ile Ala Thr Tyr Phe Cys Gln Gln Gly Asn Thr
            100                 105                 110 ctg ccc tac acc ttt ggc ggc gga aca aag ctg gaa atc acc ggc agc       384
Leu Pro Tyr Thr Phe Gly Gly Gly Thr Lys Leu Glu Ile Thr Gly Ser
        115                 120                 125
```

-continued

| | | |
|---|---|---|
| acc tcc ggc agc ggc aag cct ggc agc ggc gag ggc agc acc aag ggc<br>Thr Ser Gly Ser Gly Lys Pro Gly Ser Gly Glu Gly Ser Thr Lys Gly<br>130                     135                    140 | 432 |
| gag gtg aag ctg cag gaa agc ggc cct ggc ctg gtg gcc ccc agc cag<br>Glu Val Lys Leu Gln Glu Ser Gly Pro Gly Leu Val Ala Pro Ser Gln<br>145                     150                 155                160 | 480 |
| agc ctg agc gtg acc tgc acc gtg agc ggc gtg agc ctg ccc gac tac<br>Ser Leu Ser Val Thr Cys Thr Val Ser Gly Val Ser Leu Pro Asp Tyr<br>                  165                    170                175 | 528 |
| ggc gtg agc tgg atc cgg cag ccc ccc agg aag ggc ctg gaa tgg ctg<br>Gly Val Ser Trp Ile Arg Gln Pro Pro Arg Lys Gly Leu Glu Trp Leu<br>                180                      185                  190 | 576 |
| ggc gtg atc tgg ggc agc gag acc acc tac tac aac agc gcc ctg aag<br>Gly Val Ile Trp Gly Ser Glu Thr Thr Tyr Tyr Asn Ser Ala Leu Lys<br>                  195                    200                205 | 624 |
| agc cgg ctg acc atc atc aag gac aac agc aag agc cag gtg ttc ctg<br>Ser Arg Leu Thr Ile Ile Lys Asp Asn Ser Lys Ser Gln Val Phe Leu<br>210                     215                    220 | 672 |
| aag atg aac agc ctg cag acc gac gac acc gcc atc tac tac tgc gcc<br>Lys Met Asn Ser Leu Gln Thr Asp Asp Thr Ala Ile Tyr Tyr Cys Ala<br>225                     230                    235                240 | 720 |
| aag cac tac tac tac ggc ggc agc tac gcc atg gac tac tgg ggc cag<br>Lys His Tyr Tyr Tyr Gly Gly Ser Tyr Ala Met Asp Tyr Trp Gly Gln<br>                  245                    250                255 | 768 |
| ggc acc agc gtg acc gtg agc agc gga ggt ggt gga tcc gag gtg cag<br>Gly Thr Ser Val Thr Val Ser Ser Gly Gly Gly Gly Ser Glu Val Gln<br>                  260                    265                270 | 816 |
| ctg cag cag tct ggg gct gag ctg gtg aag cct ggg gcc tca gtg aag<br>Leu Gln Gln Ser Gly Ala Glu Leu Val Lys Pro Gly Ala Ser Val Lys<br>                    275                    280                285 | 864 |
| atg tcc tgc aag gct tct ggc tac aca ttt acc agt tac aat atg cac<br>Met Ser Cys Lys Ala Ser Gly Tyr Thr Phe Thr Ser Tyr Asn Met His<br>                  290                    295                300 | 912 |
| tgg gta aag cag aca cct gga cag ggc ctg gaa tgg att gga gct att<br>Trp Val Lys Gln Thr Pro Gly Gln Gly Leu Glu Trp Ile Gly Ala Ile<br>305                     310                    315                320 | 960 |
| tat cca gga aat ggt gat act tcc tac aat cag aag ttc aaa ggc aag<br>Tyr Pro Gly Asn Gly Asp Thr Ser Tyr Asn Gln Lys Phe Lys Gly Lys<br>                  325                    330                335 | 1008 |
| gcc aca ttg act gca gac aaa tcc tcc agc aca gcc tac atg cag ctc<br>Ala Thr Leu Thr Ala Asp Lys Ser Ser Ser Thr Ala Tyr Met Gln Leu<br>                    340                    345                350 | 1056 |
| agc agc ctg aca tct gag gac tct gcg gac tat tac tgt gca aga tct<br>Ser Ser Leu Thr Ser Glu Asp Ser Ala Asp Tyr Tyr Cys Ala Arg Ser<br>                  355                    360                365 | 1104 |
| aat tat tac ggt agt agc tac tgg ttc ttc gat gtc tgg ggc gca ggg<br>Asn Tyr Tyr Gly Ser Ser Tyr Trp Phe Phe Asp Val Trp Gly Ala Gly<br>370                     375                    380 | 1152 |
| acc acg gtc acc gtc tcc tca ggc agt act agc ggt ggt ggc tcc ggg<br>Thr Thr Val Thr Val Ser Ser Gly Ser Thr Ser Gly Gly Gly Ser Gly<br>385                     390                    395                400 | 1200 |
| ggc ggt tcc ggt ggg ggc ggc agc agc gac att gtg ctg acc caa tct<br>Gly Gly Ser Gly Gly Gly Gly Ser Ser Asp Ile Val Leu Thr Gln Ser<br>                  405                    410                415 | 1248 |
| cca gct atc ctg tct gca tct cca ggg gag aag gtc aca atg act tgc<br>Pro Ala Ile Leu Ser Ala Ser Pro Gly Glu Lys Val Thr Met Thr Cys<br>                    420                    425                430 | 1296 |
| agg gcc agc tca agt gta aat tac atg gac tgg tac cag aag aag cca<br>Arg Ala Ser Ser Ser Val Asn Tyr Met Asp Trp Tyr Gln Lys Lys Pro<br>                  435                    440                445 | 1344 |

-continued

```
gga tcc tcc ccc aaa ccc tgg att tat gcc aca tcc aac ctg gct tct      1392
Gly Ser Ser Pro Lys Pro Trp Ile Tyr Ala Thr Ser Asn Leu Ala Ser
        450                 455                 460 gga gtc cct gct cgc ttc agt ggc agt ggg tct ggg acc tct tac tct      1440
Gly Val Pro Ala Arg Phe Ser Gly Ser Gly Ser Gly Thr Ser Tyr Ser
465                 470                 475                 480 ctc aca atc agc aga gtg gag gct gaa gat gct gcc act tat tac tgc      1488
Leu Thr Ile Ser Arg Val Glu Ala Glu Asp Ala Ala Thr Tyr Tyr Cys
                    485                 490                 495 cag cag tgg agt ttt aat cca ccc acg ttc gga ggg ggg acc aag ctg      1536
Gln Gln Trp Ser Phe Asn Pro Pro Thr Phe Gly Gly Gly Thr Lys Leu
            500                 505                 510 gaa ata aaa gag agc aag tac gga ccg ccc tgc ccc cct tgc cct atg      1584
Glu Ile Lys Glu Ser Lys Tyr Gly Pro Pro Cys Pro Pro Cys Pro Met
        515                 520                 525 ttc tgg gtg ctg gtg gtg gtc gga ggc gtg ctg gcc tgc tac agc ctg      1632
Phe Trp Val Leu Val Val Val Gly Gly Val Leu Ala Cys Tyr Ser Leu
530                 535                 540 ctg gtc acc gtg gcc ttc atc atc ttt tgg gtg aaa cgg ggc aga aag      1680
Leu Val Thr Val Ala Phe Ile Ile Phe Trp Val Lys Arg Gly Arg Lys
545                 550                 555                 560 aaa ctc ctg tat ata ttc aaa caa cca ttt atg aga cca gta caa act      1728
Lys Leu Leu Tyr Ile Phe Lys Gln Pro Phe Met Arg Pro Val Gln Thr
                    565                 570                 575 act caa gag gaa gat ggc tgt agc tgc cga ttt cca gaa gaa gaa gaa      1776
Thr Gln Glu Glu Asp Gly Cys Ser Cys Arg Phe Pro Glu Glu Glu Glu
            580                 585                 590 gga gga tgt gaa ctg cgg gtg aag ttc agc aga agc gcc gac gcc cct      1824
Gly Gly Cys Glu Leu Arg Val Lys Phe Ser Arg Ser Ala Asp Ala Pro
        595                 600                 605 gcc tac cag cag ggc cag aat cag ctg tac aac gag ctg aac ctg ggc      1872
Ala Tyr Gln Gln Gly Gln Asn Gln Leu Tyr Asn Glu Leu Asn Leu Gly
610                 615                 620 aga agg gaa gag tac gac gtc ctg gat aag cgg aga ggc cgg gac cct      1920
Arg Arg Glu Glu Tyr Asp Val Leu Asp Lys Arg Arg Gly Arg Asp Pro
625                 630                 635                 640 gag atg ggc ggc aag cct cgg cgg aag aac ccc cag gaa ggc ctg tat      1968
Glu Met Gly Gly Lys Pro Arg Arg Lys Asn Pro Gln Glu Gly Leu Tyr
                    645                 650                 655 aac gaa ctg cag aaa gac aag atg gcc gag gcc tac agc gag atc ggc      2016
Asn Glu Leu Gln Lys Asp Lys Met Ala Glu Ala Tyr Ser Glu Ile Gly
            660                 665                 670 atg aag ggc gag cgg agg cgg ggc aag ggc cac gac ggc ctg tat cag      2064
Met Lys Gly Glu Arg Arg Arg Gly Lys Gly His Asp Gly Leu Tyr Gln
        675                 680                 685 ggc ctg tcc acc gcc acc aag gat acc tac gac gcc ctg cac atg cag      2112
Gly Leu Ser Thr Ala Thr Lys Asp Thr Tyr Asp Ala Leu His Met Gln
690                 695                 700 gcc ctg ccc cca agg ctc gag ggc ggc gga gag ggc aga gga agt ctt      2160
Ala Leu Pro Pro Arg Leu Glu Gly Gly Gly Glu Gly Arg Gly Ser Leu
705                 710                 715                 720 cta aca tgc ggt gac gtg gag gag aat ccc ggc cct agg atg ctt ctc      2208
Leu Thr Cys Gly Asp Val Glu Glu Asn Pro Gly Pro Arg Met Leu Leu
                    725                 730                 735 ctg gtg aca agc ctt ctg ctc tgt gag tta cca cac cca gca ttc ctc      2256
Leu Val Thr Ser Leu Leu Leu Cys Glu Leu Pro His Pro Ala Phe Leu
            740                 745                 750 ctg atc cca cgc aaa gtg tgt aac gga ata ggt att ggt gaa ttt aaa      2304
Leu Ile Pro Arg Lys Val Cys Asn Gly Ile Gly Ile Gly Glu Phe Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 755 |     |     |     |     | 760 |     |     |     |     | 765 |     |     |     |      |
| gac | tca | ctc | tcc | ata | aat | gct | acg | aat | att | aaa | cac | ttc | aaa | aac | tgc | 2352 |
| Asp | Ser | Leu | Ser | Ile | Asn | Ala | Thr | Asn | Ile | Lys | His | Phe | Lys | Asn | Cys |      |
|     | 770 |     |     |     |     | 775 |     |     |     |     | 780 |     |     |     |     |      |
| acc | tcc | atc | agt | ggc | gat | ctc | cac | atc | ctg | ccg | gtg | gca | ttt | agg | ggt | 2400 |
| Thr | Ser | Ile | Ser | Gly | Asp | Leu | His | Ile | Leu | Pro | Val | Ala | Phe | Arg | Gly |      |
| 785 |     |     |     |     | 790 |     |     |     |     | 795 |     |     |     |     | 800 |      |
| gac | tcc | ttc | aca | cat | act | cct | cct | ctg | gat | cca | cag | gaa | ctg | gat | att | 2448 |
| Asp | Ser | Phe | Thr | His | Thr | Pro | Pro | Leu | Asp | Pro | Gln | Glu | Leu | Asp | Ile |      |
|     |     |     |     | 805 |     |     |     |     | 810 |     |     |     |     | 815 |     |      |
| ctg | aaa | acc | gta | aag | gaa | atc | aca | ggg | ttt | ttg | ctg | att | cag | gct | tgg | 2496 |
| Leu | Lys | Thr | Val | Lys | Glu | Ile | Thr | Gly | Phe | Leu | Leu | Ile | Gln | Ala | Trp |      |
|     |     |     | 820 |     |     |     |     | 825 |     |     |     |     | 830 |     |     |      |
| cct | gaa | aac | agg | acg | gac | ctc | cat | gcc | ttt | gag | aac | cta | gaa | atc | ata | 2544 |
| Pro | Glu | Asn | Arg | Thr | Asp | Leu | His | Ala | Phe | Glu | Asn | Leu | Glu | Ile | Ile |      |
|     |     | 835 |     |     |     |     | 840 |     |     |     |     | 845 |     |     |     |      |
| cgc | ggc | agg | acc | aag | caa | cat | ggt | cag | ttt | tct | ctt | gca | gtc | gtc | agc | 2592 |
| Arg | Gly | Arg | Thr | Lys | Gln | His | Gly | Gln | Phe | Ser | Leu | Ala | Val | Val | Ser |      |
|     | 850 |     |     |     |     | 855 |     |     |     |     | 860 |     |     |     |     |      |
| ctg | aac | ata | aca | tcc | ttg | gga | tta | cgc | tcc | ctc | aag | gag | ata | agt | gat | 2640 |
| Leu | Asn | Ile | Thr | Ser | Leu | Gly | Leu | Arg | Ser | Leu | Lys | Glu | Ile | Ser | Asp |      |
| 865 |     |     |     |     | 870 |     |     |     |     | 875 |     |     |     |     | 880 |      |
| gga | gat | gtg | ata | att | tca | gga | aac | aaa | aat | ttg | tgc | tat | gca | aat | aca | 2688 |
| Gly | Asp | Val | Ile | Ile | Ser | Gly | Asn | Lys | Asn | Leu | Cys | Tyr | Ala | Asn | Thr |      |
|     |     |     |     | 885 |     |     |     |     | 890 |     |     |     |     | 895 |     |      |
| ata | aac | tgg | aaa | aaa | ctg | ttt | ggg | acc | tcc | ggt | cag | aaa | acc | aaa | att | 2736 |
| Ile | Asn | Trp | Lys | Lys | Leu | Phe | Gly | Thr | Ser | Gly | Gln | Lys | Thr | Lys | Ile |      |
|     |     |     | 900 |     |     |     |     | 905 |     |     |     |     | 910 |     |     |      |
| ata | agc | aac | aga | ggt | gaa | aac | agc | tgc | aag | gcc | aca | ggc | cag | gtc | tgc | 2784 |
| Ile | Ser | Asn | Arg | Gly | Glu | Asn | Ser | Cys | Lys | Ala | Thr | Gly | Gln | Val | Cys |      |
|     |     | 915 |     |     |     |     | 920 |     |     |     |     | 925 |     |     |     |      |
| cat | gcc | ttg | tgc | tcc | ccc | gag | ggc | tgc | tgg | ggc | ccg | gag | ccc | agg | gac | 2832 |
| His | Ala | Leu | Cys | Ser | Pro | Glu | Gly | Cys | Trp | Gly | Pro | Glu | Pro | Arg | Asp |      |
|     | 930 |     |     |     |     | 935 |     |     |     |     | 940 |     |     |     |     |      |
| tgc | gtc | tct | tgc | cgg | aat | gtc | agc | cga | ggc | agg | gaa | tgc | gtg | gac | aag | 2880 |
| Cys | Val | Ser | Cys | Arg | Asn | Val | Ser | Arg | Gly | Arg | Glu | Cys | Val | Asp | Lys |      |
| 945 |     |     |     |     | 950 |     |     |     |     | 955 |     |     |     |     | 960 |      |
| tgc | aac | ctt | ctg | gag | ggt | gag | cca | agg | gag | ttt | gtg | gag | aac | tct | gag | 2928 |
| Cys | Asn | Leu | Leu | Glu | Gly | Glu | Pro | Arg | Glu | Phe | Val | Glu | Asn | Ser | Glu |      |
|     |     |     |     | 965 |     |     |     |     | 970 |     |     |     |     | 975 |     |      |
| tgc | ata | cag | tgc | cac | cca | gag | tgc | ctg | cct | cag | gcc | atg | aac | atc | acc | 2976 |
| Cys | Ile | Gln | Cys | His | Pro | Glu | Cys | Leu | Pro | Gln | Ala | Met | Asn | Ile | Thr |      |
|     |     |     | 980 |     |     |     |     | 985 |     |     |     |     | 990 |     |     |      |
| tgc | aca | gga | cgg | gga | cca | gac | aac | tgt | atc | cag | tgt | gcc | cac | tac | att | 3024 |
| Cys | Thr | Gly | Arg | Gly | Pro | Asp | Asn | Cys | Ile | Gln | Cys | Ala | His | Tyr | Ile |      |
|     |     | 995 |     |     |     |     | 1000 |    |     |     |     | 1005 |    |     |     |      |
| gac | ggc | ccc | cac | tgc | gtc | aag | acc | tgc | ccg | gca | gga | gtc | atg | gga |     | 3069 |
| Asp | Gly | Pro | His | Cys | Val | Lys | Thr | Cys | Pro | Ala | Gly | Val | Met | Gly |     |      |
|     | 1010 |    |     |     |     | 1015 |   |     |     |     | 1020 |   |     |     |     |      |
| gaa | aac | aac | acc | ctg | gtc | tgg | aag | tac | gca | gac | gcc | ggc | cat | gtg |     | 3114 |
| Glu | Asn | Asn | Thr | Leu | Val | Trp | Lys | Tyr | Ala | Asp | Ala | Gly | His | Val |     |      |
|     | 1025 |    |     |     |     | 1030 |   |     |     |     | 1035 |   |     |     |     |      |
| tgc | cac | ctg | tgc | cat | cca | aac | tgc | acc | tac | gga | tgc | act | ggg | cca |     | 3159 |
| Cys | His | Leu | Cys | His | Pro | Asn | Cys | Thr | Tyr | Gly | Cys | Thr | Gly | Pro |     |      |
|     | 1040 |    |     |     |     | 1045 |   |     |     |     | 1050 |   |     |     |     |      |
| ggt | ctt | gaa | ggc | tgt | cca | acg | aat | ggg | cct | aag | atc | ccg | tcc | atc |     | 3204 |
| Gly | Leu | Glu | Gly | Cys | Pro | Thr | Asn | Gly | Pro | Lys | Ile | Pro | Ser | Ile |     |      |
|     | 1055 |    |     |     |     | 1060 |   |     |     |     | 1065 |   |     |     |     |      |
| gcc | act | ggg | atg | gtg | ggg | gcc | ctc | ctc | ttg | ctg | ctg | gtg | gtg | gcc |     | 3249 |

```
Ala Thr Gly Met Val Gly Ala Leu Leu Leu Leu Leu Val Val Ala
         1070            1075                1080 ctg ggg atc ggc ctc ttc atg tga                              3273
Leu Gly Ile Gly Leu Phe Met
         1085                1090
```

<210> SEQ ID NO 3
<211> LENGTH: 1090
<212> TYPE: PRT
<213> ORGANISM: Artificial Sequence
<220> FEATURE:
<223> OTHER INFORMATION: Synthetic Construct

<400> SEQUENCE: 3

```
Met Leu Leu Leu Val Thr Ser Leu Leu Leu Cys Glu Leu Pro His Pro
1               5                   10                  15

Ala Phe Leu Leu Ile Pro Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Lys Tyr Leu Asn Trp Tyr Gln Gln Lys Pro Asp Gly Thr Val Lys
    50                  55                  60

Leu Leu Ile Tyr His Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Thr Gly Ser
        115                 120                 125

Thr Ser Gly Ser Gly Lys Pro Gly Ser Gly Glu Gly Ser Thr Lys Gly
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Gly Gly Gly Gly Ser Glu Val Gln
            260                 265                 270

Leu Gln Gln Ser Gly Ala Glu Leu Val Lys Pro Gly Ala Ser Val Lys
        275                 280                 285

Met Ser Cys Lys Ala Ser Gly Tyr Thr Phe Thr Ser Tyr Asn Met His
    290                 295                 300

Trp Val Lys Gln Thr Pro Gly Gln Gly Leu Glu Trp Ile Gly Ala Ile
305                 310                 315                 320

Tyr Pro Gly Asn Gly Asp Thr Ser Tyr Asn Gln Lys Phe Lys Gly Lys
                325                 330                 335
```

```
Ala Thr Leu Thr Ala Asp Lys Ser Ser Thr Ala Tyr Met Gln Leu
            340                 345                 350

Ser Ser Leu Thr Ser Glu Asp Ser Ala Asp Tyr Tyr Cys Ala Arg Ser
        355                 360                 365

Asn Tyr Tyr Gly Ser Ser Tyr Trp Phe Phe Asp Val Trp Gly Ala Gly
    370                 375                 380

Thr Thr Val Thr Val Ser Ser Gly Ser Thr Ser Gly Gly Ser Gly
385                 390                 395                 400

Gly Gly Ser Gly Gly Gly Ser Ser Asp Ile Val Leu Thr Gln Ser
            405                 410                 415

Pro Ala Ile Leu Ser Ala Ser Pro Gly Glu Lys Val Thr Met Thr Cys
        420                 425                 430

Arg Ala Ser Ser Ser Val Asn Tyr Met Asp Trp Tyr Gln Lys Lys Pro
    435                 440                 445

Gly Ser Ser Pro Lys Pro Trp Ile Tyr Ala Thr Ser Asn Leu Ala Ser
    450                 455                 460

Gly Val Pro Ala Arg Phe Ser Gly Ser Gly Ser Gly Thr Ser Tyr Ser
465                 470                 475                 480

Leu Thr Ile Ser Arg Val Glu Ala Glu Asp Ala Ala Thr Tyr Tyr Cys
            485                 490                 495

Gln Gln Trp Ser Phe Asn Pro Pro Thr Phe Gly Gly Gly Thr Lys Leu
        500                 505                 510

Glu Ile Lys Glu Ser Lys Tyr Gly Pro Pro Cys Pro Pro Cys Pro Met
    515                 520                 525

Phe Trp Val Leu Val Val Val Gly Gly Val Leu Ala Cys Tyr Ser Leu
    530                 535                 540

Leu Val Thr Val Ala Phe Ile Ile Phe Trp Val Lys Arg Gly Arg Lys
545                 550                 555                 560

Lys Leu Leu Tyr Ile Phe Lys Gln Pro Phe Met Arg Pro Val Gln Thr
            565                 570                 575

Thr Gln Glu Glu Asp Gly Cys Ser Cys Arg Phe Pro Glu Glu Glu
        580                 585                 590

Gly Gly Cys Glu Leu Arg Val Lys Phe Ser Arg Ser Ala Asp Ala Pro
    595                 600                 605

Ala Tyr Gln Gln Gly Gln Asn Gln Leu Tyr Asn Glu Leu Asn Leu Gly
    610                 615                 620

Arg Arg Glu Glu Tyr Asp Val Leu Asp Lys Arg Arg Gly Arg Asp Pro
625                 630                 635                 640

Glu Met Gly Gly Lys Pro Arg Arg Lys Asn Pro Gln Glu Gly Leu Tyr
            645                 650                 655

Asn Glu Leu Gln Lys Asp Lys Met Ala Glu Ala Tyr Ser Glu Ile Gly
        660                 665                 670

Met Lys Gly Glu Arg Arg Arg Gly Lys Gly His Asp Gly Leu Tyr Gln
    675                 680                 685

Gly Leu Ser Thr Ala Thr Lys Asp Thr Tyr Asp Ala Leu His Met Gln
    690                 695                 700

Ala Leu Pro Pro Arg Leu Glu Gly Gly Gly Glu Gly Arg Gly Ser Leu
705                 710                 715                 720

Leu Thr Cys Gly Asp Val Glu Glu Asn Pro Gly Pro Arg Met Leu Leu
            725                 730                 735

Leu Val Thr Ser Leu Leu Leu Cys Glu Leu Pro His Pro Ala Phe Leu
        740                 745                 750
```

Leu Ile Pro Arg Lys Val Cys Asn Gly Ile Gly Ile Gly Glu Phe Lys
            755                 760                 765

Asp Ser Leu Ser Ile Asn Ala Thr Asn Ile Lys His Phe Lys Asn Cys
770                 775                 780

Thr Ser Ile Ser Gly Asp Leu His Ile Leu Pro Val Ala Phe Arg Gly
785                 790                 795                 800

Asp Ser Phe Thr His Thr Pro Pro Leu Asp Pro Gln Glu Leu Asp Ile
                805                 810                 815

Leu Lys Thr Val Lys Glu Ile Thr Gly Phe Leu Leu Ile Gln Ala Trp
            820                 825                 830

Pro Glu Asn Arg Thr Asp Leu His Ala Phe Glu Asn Leu Glu Ile Ile
                835                 840                 845

Arg Gly Arg Thr Lys Gln His Gly Gln Phe Ser Leu Ala Val Val Ser
850                 855                 860

Leu Asn Ile Thr Ser Leu Gly Leu Arg Ser Leu Lys Glu Ile Ser Asp
865                 870                 875                 880

Gly Asp Val Ile Ile Ser Gly Asn Lys Asn Leu Cys Tyr Ala Asn Thr
                885                 890                 895

Ile Asn Trp Lys Lys Leu Phe Gly Thr Ser Gly Gln Lys Thr Lys Ile
            900                 905                 910

Ile Ser Asn Arg Gly Glu Asn Ser Cys Lys Ala Thr Gly Gln Val Cys
            915                 920                 925

His Ala Leu Cys Ser Pro Glu Gly Cys Trp Gly Pro Glu Pro Arg Asp
930                 935                 940

Cys Val Ser Cys Arg Asn Val Ser Arg Gly Arg Glu Cys Val Asp Lys
945                 950                 955                 960

Cys Asn Leu Leu Glu Gly Glu Pro Arg Glu Phe Val Glu Asn Ser Glu
                965                 970                 975

Cys Ile Gln Cys His Pro Glu Cys Leu Pro Gln Ala Met Asn Ile Thr
            980                 985                 990

Cys Thr Gly Arg Gly Pro Asp Asn Cys Ile Gln Cys Ala His Tyr Ile
            995                 1000                1005

Asp Gly Pro His Cys Val Lys Thr Cys Pro Ala Gly Val Met Gly
    1010                1015                1020

Glu Asn Asn Thr Leu Val Trp Lys Tyr Ala Asp Ala Gly His Val
    1025                1030                1035

Cys His Leu Cys His Pro Asn Cys Thr Tyr Gly Cys Thr Gly Pro
    1040                1045                1050

Gly Leu Glu Gly Cys Pro Thr Asn Gly Pro Lys Ile Pro Ser Ile
    1055                1060                1065

Ala Thr Gly Met Val Gly Ala Leu Leu Leu Leu Leu Val Val Ala
    1070                1075                1080

Leu Gly Ile Gly Leu Phe Met
    1085                1090

<210> SEQ ID NO 4
<211> LENGTH: 582
<212> TYPE: DNA
<213> ORGANISM: Artificial Sequence
<220> FEATURE:
<223> OTHER INFORMATION: IgG4hinge-CD28tm-41BB-CD3Zeta

<400> SEQUENCE: 4
gagagcaagt acggaccgcc ctgcccccct tgccctatgt tctgggtgct ggtggtggtc     60
ggaggcgtgc tggcctgcta cagcctgctg gtcaccgtgg ccttcatcat cttttgggtg    120

```
aaacggggca gaaagaaact cctgtatata ttcaaacaac catttatgag accagtacaa    180
actactcaag aggaagatgg ctgtagctgc cgatttccag aagaagaaga aggaggatgt    240
gaactgcggg tgaagttcag cagaagcgcc gacgcccctg cctaccagca gggccagaat    300
cagctgtaca acgagctgaa cctgggcaga agggaagagt acgacgtcct ggataagcgg    360
agaggccggg accctgagat gggcggcaag cctcggcgga agaaccccca ggaaggcctg    420
tataacgaac tgcagaaaga caagatggcc gaggcctaca gcgagatcgg catgaagggc    480
gagcggaggc ggggcaaggg ccacgacggc ctgtatcagg gcctgtccac cgccaccaag    540 gataccctacg acgccctgca catgcaggcc ctgccccaa gg                       582
```

```
<210> SEQ ID NO 5
<211> LENGTH: 582
<212> TYPE: DNA
<213> ORGANISM: Artificial Sequence
<220> FEATURE:
<223> OTHER INFORMATION: IgG4hinge-CD28tm-41BB-CD3Zeta
<220> FEATURE:
<221> NAME/KEY: CDS
<222> LOCATION: (1)..(582)

<400> SEQUENCE: 5
```

```
gag agc aag tac gga ccg ccc tgc ccc cct tgc cct atg ttc tgg gtg     48
Glu Ser Lys Tyr Gly Pro Pro Cys Pro Pro Cys Pro Met Phe Trp Val
1               5                   10                  15 ctg gtg gtg gtc gga ggc gtg ctg gcc tgc tac agc ctg ctg gtc acc    96
Leu Val Val Val Gly Gly Val Leu Ala Cys Tyr Ser Leu Leu Val Thr
                20                  25                  30 gtg gcc ttc atc atc ttt tgg gtg aaa cgg ggc aga aag aaa ctc ctg   144
Val Ala Phe Ile Ile Phe Trp Val Lys Arg Gly Arg Lys Lys Leu Leu
            35                  40                  45 tat ata ttc aaa caa cca ttt atg aga cca gta caa act act caa gag   192
Tyr Ile Phe Lys Gln Pro Phe Met Arg Pro Val Gln Thr Thr Gln Glu
        50                  55                  60 gaa gat ggc tgt agc tgc cga ttt cca gaa gaa gaa gaa gga gga tgt   240
Glu Asp Gly Cys Ser Cys Arg Phe Pro Glu Glu Glu Glu Gly Gly Cys
65                  70                  75                  80 gaa ctg cgg gtg aag ttc agc aga agc gcc gac gcc cct gcc tac cag   288
Glu Leu Arg Val Lys Phe Ser Arg Ser Ala Asp Ala Pro Ala Tyr Gln
                85                  90                  95 cag ggc cag aat cag ctg tac aac gag ctg aac ctg ggc aga agg gaa   336
Gln Gly Gln Asn Gln Leu Tyr Asn Glu Leu Asn Leu Gly Arg Arg Glu
            100                 105                 110 gag tac gac gtc ctg gat aag cgg aga ggc cgg gac cct gag atg ggc   384
Glu Tyr Asp Val Leu Asp Lys Arg Arg Gly Arg Asp Pro Glu Met Gly
        115                 120                 125 ggc aag cct cgg cgg aag aac ccc cag gaa ggc ctg tat aac gaa ctg   432
Gly Lys Pro Arg Arg Lys Asn Pro Gln Glu Gly Leu Tyr Asn Glu Leu
    130                 135                 140 cag aaa gac aag atg gcc gag gcc tac agc gag atc ggc atg aag ggc   480
Gln Lys Asp Lys Met Ala Glu Ala Tyr Ser Glu Ile Gly Met Lys Gly
145                 150                 155                 160 gag cgg agg cgg ggc aag ggc cac gac ggc ctg tat cag ggc ctg tcc   528
Glu Arg Arg Arg Gly Lys Gly His Asp Gly Leu Tyr Gln Gly Leu Ser
                165                 170                 175 acc gcc acc aag gat acc tac gac gcc ctg cac atg cag gcc ctg ccc   576
Thr Ala Thr Lys Asp Thr Tyr Asp Ala Leu His Met Gln Ala Leu Pro
            180                 185                 190 cca agg                                                              582
```

-continued

Pro Arg

<210> SEQ ID NO 6
<211> LENGTH: 194
<212> TYPE: PRT
<213> ORGANISM: Artificial Sequence
<220> FEATURE:
<223> OTHER INFORMATION: Synthetic Construct

<400> SEQUENCE: 6

```
Glu Ser Lys Tyr Gly Pro Pro Cys Pro Pro Cys Pro Met Phe Trp Val
1               5                   10                  15

Leu Val Val Val Gly Gly Val Leu Ala Cys Tyr Ser Leu Leu Val Thr
            20                  25                  30

Val Ala Phe Ile Ile Phe Trp Val Lys Arg Gly Arg Lys Lys Leu Leu
        35                  40                  45

Tyr Ile Phe Lys Gln Pro Phe Met Arg Pro Val Gln Thr Thr Gln Glu
    50                  55                  60

Glu Asp Gly Cys Ser Cys Arg Phe Pro Glu Glu Glu Glu Gly Gly Cys
65                  70                  75                  80

Glu Leu Arg Val Lys Phe Ser Arg Ser Ala Asp Ala Pro Ala Tyr Gln
                85                  90                  95

Gln Gly Gln Asn Gln Leu Tyr Asn Glu Leu Asn Leu Gly Arg Arg Glu
            100                 105                 110

Glu Tyr Asp Val Leu Asp Lys Arg Arg Gly Arg Asp Pro Glu Met Gly
        115                 120                 125

Gly Lys Pro Arg Arg Lys Asn Pro Gln Glu Gly Leu Tyr Asn Glu Leu
    130                 135                 140

Gln Lys Asp Lys Met Ala Glu Ala Tyr Ser Glu Ile Gly Met Lys Gly
145                 150                 155                 160

Glu Arg Arg Arg Gly Lys Gly His Asp Gly Leu Tyr Gln Gly Leu Ser
                165                 170                 175

Thr Ala Thr Lys Asp Thr Tyr Asp Ala Leu His Met Gln Ala Leu Pro
            180                 185                 190

Pro Arg
```

<210> SEQ ID NO 7
<211> LENGTH: 2910
<212> TYPE: DNA
<213> ORGANISM: Artificial Sequence
<220> FEATURE:
<223> OTHER INFORMATION:
    GMCSFRss-CD19scFv-Gly4serlinker-CD20scFv-huIgG4hinge/CH2/CH3-CD28
    tm/CD28cyto-41BB-CD3Zeta

<400> SEQUENCE: 7

| | | |
|---|---|---|
| atgctgctgc tggtgaccag cctgctgctg tgcgagctgc ccacccccgc ctttctgctg | 60 |
| atccccgaca tccagatgac ccagaccacc tccagcctga gcgccagcct gggcgaccgg | 120 |
| gtgaccatca gctgccgggc cagccaggac atcagcaagt acctgaactg gtatcagcag | 180 |
| aagcccgacg gcaccgtcaa gctgctgatc taccacacca gcggctgca cagcggcgtg | 240 |
| cccagccggt ttagcggcag cggctccggc accgactaca gcctgaccat ctccaacctg | 300 |
| gaacaggaag atatcgccac ctactttgc agcagggca acacactgcc ctacaccttt | 360 |
| ggcggcggaa caaagctgga aatcaccggc agcacctccg gcagcggcaa gcctggcagc | 420 |
| ggcgagggca gcaccaaggg cgaggtgaag ctgcaggaaa gcggcccctgg cctggtggcc | 480 |
| cccagccaga gcctgagcgt gacctgcacc gtgagcggcg tgagcctgcc cgactacggc | 540 |

```
gtgagctgga tccggcagcc ccccaggaag ggcctggaat ggctgggcgt gatctggggc    600
agcgagacca cctactacaa cagcgccctg aagagccggc tgaccatcat caaggacaac    660
agcaagagcc aggtgttcct gaagatgaac agcctgcaga ccgacgacac cgccatctac    720
tactgcgcca agcactacta ctacggcggc agctacgcca tggactactg gggccagggc    780
accagcgtga ccgtgagcag cggaggtggt ggatccgagg tgcagctgca gcagtctggg    840
gctgagctgt gaagcctggg gcctcagtg aagatgtcct gcaaggcttc tggctacaca    900
tttaccagtt acaatatgca ctgggtaaag cagacacctg gacagggcct ggaatggatt    960
ggagctattt atccaggaaa tggtgatact tcctacaatc agaagttcaa aggcaaggcc    1020
acattgactg cagacaaatc ctccagcaca gcctacatgc agctcagcag cctgacatct    1080
gaggactctg cggactatta ctgtgcaaga tctaattatt acggtagtag ctactggttc    1140
ttcgatgtct ggggcgcagg gaccacggtc accgtctcct caggcagtac tagcggtggt    1200
ggctccgggg gcggttccgg tggggcggc agcagcgaca ttgtgctgac ccaatctcca    1260
gctatcctgt ctgcatctcc aggggagaag gtcacaatga cttgcagggc cagctcaagt    1320
gtaaattaca tggactggta ccagaagaag ccaggatcct cccccaaacc ctggatttat    1380
gccacatcca acctggcttc tggagtccct gctcgcttca gtggcagtgg gtctgggacc    1440
tcttactctc tcacaatcag cagagtggag gctgaagatg ctgccactta ttactgccag    1500
cagtggagtt ttaatccacc cacgttcgga gggggaccca agctggaaat aaaagagagc    1560
aagtacggac cgccctgccc ccttgccct gccccgagt tcctgggcgg acccagcgtg    1620
ttcctgttcc cccccaagcc caaggacacc ctgatgatca gccggacccc cgaggtgacc    1680
tgcgtggtgg tggacgtgag ccaggaagat cccgaggtcc agttcaattg gtacgtggac    1740
ggcgtggaag tgcacaacgc caagaccaag cccagagagg aacagttcaa cagcacctac    1800
cgggtggtgt ctgtgctgac cgtgctgcac caggactggc tgaacggcaa agaatacaag    1860
tgcaaggtgt ccaacaaggg cctgcccagc agcatcgaaa agaccatcag caaggccaag    1920
ggccagcctc gcgagcccca ggtgtacacc ctgcctccct cccaggaaga gatgaccaag    1980
aaccaggtgt ccctgacctg cctggtgaag ggcttctacc ccagcgacat cgccgtggag    2040
tgggagagca acggccagcc tgagaacaac tacaagacca cccctcccgt gctggacagc    2100
gacggcagct tcttcctgta cagccggctg accgtggaca agagccggtg gcaggaaggc    2160
aacgtcttta gctgcagcgt gatgcacgag gccctgcaca accactacac ccagaagagc    2220
ctgagcctgt ccctgggcaa gatgttctgg gtgctggtgg tggtgggcgg ggtgctggcc    2280
tgctacagcc tgctggtgac agtggccttc atcatctttt gggtgcggag caagcggagc    2340
agaggcggcc acagcgacta catgaacatg acccccagac ggcctggccc cacccggaag    2400
cactaccagc cctacgcccc acccagggac tttgccgcct acagaagcaa cggggcaga    2460 aagaaactcc tgtatatatt caaacaacca tttatgagac cagtacaaac tactcaagag    2520
gaagatggct gtagctgccg attttccagaa gaagaagaag gaggatgtga actgcgggtg    2580
aagttcagca gaagcgccga cgcccctgcc taccagcagg gccagaatca gctgtacaac    2640
gagctgaacc tgggcagaag ggaagagtac gacgtcctgg ataagcggag aggccgggac    2700
cctgagatgg gcggcaagcc tcggcggaag aaccccccagg aaggcctgta taacgaactg    2760
cagaaagaca gatgccgga ggcctacagc gagatcggca tgaagggcga gcggaggcgg    2820
ggcaagggcc acgacggcct gtatcagggc ctgtccaccg ccaccaagga tacctacgac    2880
```

```
gccctgcaca tgcaggccct gcccccaagg                                        2910
```

<210> SEQ ID NO 8
<211> LENGTH: 2910
<212> TYPE: DNA
<213> ORGANISM: Artificial Sequence
<220> FEATURE:
<223> OTHER INFORMATION:
   GMCSFR-ssCD19scFv-Gly4serlinker-CD20scFv-huIgG4hinge/CH2/CH3-CD28
   tm/CD28cyto-41BB-CD3Zeta
<220> FEATURE:
<221> NAME/KEY: CDS
<222> LOCATION: (1)..(2910)

<400> SEQUENCE: 8

```
atg ctg ctg ctg gtg acc agc ctg ctg ctg tgc gag ctg ccc cac ccc    48
Met Leu Leu Leu Val Thr Ser Leu Leu Leu Cys Glu Leu Pro His Pro
1               5                   10                  15 gcc ttt ctg ctg atc ccc gac atc cag atg acc cag acc acc tcc agc    96
Ala Phe Leu Leu Ile Pro Asp Ile Gln Met Thr Gln Thr Thr Ser Ser
            20                  25                  30 ctg agc gcc agc ctg ggc gac cgg gtg acc atc agc tgc cgg gcc agc    144
Leu Ser Ala Ser Leu Gly Asp Arg Val Thr Ile Ser Cys Arg Ala Ser
        35                  40                  45 cag gac atc agc aag tac ctg aac tgg tat cag cag aag ccc gac ggc    192
Gln Asp Ile Ser Lys Tyr Leu Asn Trp Tyr Gln Gln Lys Pro Asp Gly
    50                  55                  60 acc gtc aag ctg ctg atc tac cac acc agc cgg ctg cac agc ggc gtg    240
Thr Val Lys Leu Leu Ile Tyr His Thr Ser Arg Leu His Ser Gly Val
65                  70                  75                  80 ccc agc cgg ttt agc ggc agc ggc tcc ggc acc gac tac agc ctg acc    288
Pro Ser Arg Phe Ser Gly Ser Gly Ser Gly Thr Asp Tyr Ser Leu Thr
                85                  90                  95 atc tcc aac ctg gaa cag gaa gat atc gcc acc tac ttt tgc cag cag    336
Ile Ser Asn Leu Glu Gln Glu Asp Ile Ala Thr Tyr Phe Cys Gln Gln
            100                 105                 110 ggc aac aca ctg ccc tac acc ttt ggc gga aca aag ctg gaa atc       384
Gly Asn Thr Leu Pro Tyr Thr Phe Gly Gly Gly Thr Lys Leu Glu Ile
        115                 120                 125 acc ggc agc acc tcc ggc agc ggc aag cct ggc agc ggc gag ggc agc    432
Thr Gly Ser Thr Ser Gly Ser Gly Lys Pro Gly Ser Gly Glu Gly Ser
    130                 135                 140 acc aag ggc gag gtg aag ctg cag gaa agc ggc cct ggc ctg gtg gcc    480
Thr Lys Gly Glu Val Lys Leu Gln Glu Ser Gly Pro Gly Leu Val Ala
145                 150                 155                 160 ccc agc cag agc ctg agc gtg acc tgc acc gtg agc ggc gtg agc ctg    528
Pro Ser Gln Ser Leu Ser Val Thr Cys Thr Val Ser Gly Val Ser Leu
                165                 170                 175 ccc gac tac ggc gtg agc tgg atc cgg cag ccc ccc agg aag ggc ctg    576
Pro Asp Tyr Gly Val Ser Trp Ile Arg Gln Pro Pro Arg Lys Gly Leu
            180                 185                 190 gaa tgg ctg ggc gtg atc tgg ggc agc gag acc acc tac tac aac agc    624
Glu Trp Leu Gly Val Ile Trp Gly Ser Glu Thr Thr Tyr Tyr Asn Ser
        195                 200                 205 gcc ctg aag agc cgg ctg acc atc atc aag gac aac agc aag agc cag    672
Ala Leu Lys Ser Arg Leu Thr Ile Ile Lys Asp Asn Ser Lys Ser Gln
    210                 215                 220 gtg ttc ctg aag atg aac agc ctg cag acc gac gac acc gcc atc tac    720
Val Phe Leu Lys Met Asn Ser Leu Gln Thr Asp Asp Thr Ala Ile Tyr
225                 230                 235                 240 tac tgc gcc aag cac tac tac tac ggc ggc agc tac gcc atg gac tac    768
Tyr Cys Ala Lys His Tyr Tyr Tyr Gly Gly Ser Tyr Ala Met Asp Tyr
```

|     |     |
| --- | --- |
| tgg ggc cag ggc acc agc gtg acc gtg agc agc gga ggt ggt gga tcc<br>Trp Gly Gln Gly Thr Ser Val Thr Val Ser Ser Gly Gly Gly Gly Ser<br>          260                  265              270 | 816 |
| gag gtg cag ctg cag cag tct ggg gct gag ctg gtg aag cct ggg gcc<br>Glu Val Gln Leu Gln Gln Ser Gly Ala Glu Leu Val Lys Pro Gly Ala<br>     275                 280               285 | 864 |
| tca gtg aag atg tcc tgc aag gct tct ggc tac aca ttt acc agt tac<br>Ser Val Lys Met Ser Cys Lys Ala Ser Gly Tyr Thr Phe Thr Ser Tyr<br>290               295                 300 | 912 |
| aat atg cac tgg gta aag cag aca cct gga cag ggc ctg gaa tgg att<br>Asn Met His Trp Val Lys Gln Thr Pro Gly Gln Gly Leu Glu Trp Ile<br>305               310               315             320 | 960 |
| gga gct att tat cca gga aat ggt gat act tcc tac aat cag aag ttc<br>Gly Ala Ile Tyr Pro Gly Asn Gly Asp Thr Ser Tyr Asn Gln Lys Phe<br>          325                 330             335 | 1008 |
| aaa ggc aag gcc aca ttg act gca gac aaa tcc tcc agc aca gcc tac<br>Lys Gly Lys Ala Thr Leu Thr Ala Asp Lys Ser Ser Ser Thr Ala Tyr<br>               340               345             350 | 1056 |
| atg cag ctc agc agc ctg aca tct gag gac tct gcg gac tat tac tgt<br>Met Gln Leu Ser Ser Leu Thr Ser Glu Asp Ser Ala Asp Tyr Tyr Cys<br>               355               360             365 | 1104 |
| gca aga tct aat tat tac ggt agt agc tac tgg ttc ttc gat gtc tgg<br>Ala Arg Ser Asn Tyr Tyr Gly Ser Ser Tyr Trp Phe Phe Asp Val Trp<br>370               375                 380 | 1152 |
| ggc gca ggg acc acg gtc acc gtc tcc tca ggc agt act agc ggt ggt<br>Gly Ala Gly Thr Thr Val Thr Val Ser Ser Gly Ser Thr Ser Gly Gly<br>385               390               395             400 | 1200 |
| ggc tcc ggg ggc ggt tcc ggt ggg ggc ggc agc agc gac att gtg ctg<br>Gly Ser Gly Gly Gly Ser Gly Gly Gly Gly Ser Ser Asp Ile Val Leu<br>               405               410             415 | 1248 |
| acc caa tct cca gct atc ctg tct gca tct cca ggg gag aag gtc aca<br>Thr Gln Ser Pro Ala Ile Leu Ser Ala Ser Pro Gly Glu Lys Val Thr<br>               420               425             430 | 1296 |
| atg act tgc agg gcc agc tca agt gta aat tac atg gac tgg tac cag<br>Met Thr Cys Arg Ala Ser Ser Ser Val Asn Tyr Met Asp Trp Tyr Gln<br>                  435               440             445 | 1344 |
| aag aag cca gga tcc tcc ccc aaa ccc tgg att tat gcc aca tcc aac<br>Lys Lys Pro Gly Ser Ser Pro Lys Pro Trp Ile Tyr Ala Thr Ser Asn<br>450               455               460 | 1392 |
| ctg gct tct gga gtc cct gct cgc ttc agt ggc agt ggg tct ggg acc<br>Leu Ala Ser Gly Val Pro Ala Arg Phe Ser Gly Ser Gly Ser Gly Thr<br>465               470               475             480 | 1440 |
| tct tac tct ctc aca atc agc aga gtg gag gct gaa gat gct gcc act<br>Ser Tyr Ser Leu Thr Ile Ser Arg Val Glu Ala Glu Asp Ala Ala Thr<br>               485               490             495 | 1488 |
| tat tac tgc cag cag tgg agt ttt aat cca ccc acg ttc gga ggg ggg<br>Tyr Tyr Cys Gln Gln Trp Ser Phe Asn Pro Pro Thr Phe Gly Gly Gly<br>                  500               505             510 | 1536 |
| acc aag ctg gaa ata aaa gag agc aag tac gga ccg ccc tgc ccc cct<br>Thr Lys Leu Glu Ile Lys Glu Ser Lys Tyr Gly Pro Pro Cys Pro Pro<br>               515               520             525 | 1584 |
| tgc cct gcc ccc gag ttc ctg ggc gga ccc agc gtg ttc ctg ttc ccc<br>Cys Pro Ala Pro Glu Phe Leu Gly Gly Pro Ser Val Phe Leu Phe Pro<br>530               535               540 | 1632 |
| ccc aag ccc aag gac acc ctg atg atc agc cgg acc ccc gag gtg acc<br>Pro Lys Pro Lys Asp Thr Leu Met Ile Ser Arg Thr Pro Glu Val Thr<br>545               550               555             560 | 1680 |
| tgc gtg gtg gtg gac gtg agc cag gaa gat ccc gag gtc cag ttc aat | 1728 |

```
                Cys Val Val Val Asp Val Ser Gln Glu Asp Pro Glu Val Gln Phe Asn
                                565                 570                 575 tgg tac gtg gac ggc gtg gaa gtg cac aac gcc aag acc aag ccc aga           1776
Trp Tyr Val Asp Gly Val Glu Val His Asn Ala Lys Thr Lys Pro Arg
            580                 585                 590 gag gaa cag ttc aac agc acc tac cgg gtg gtg tct gtg ctg acc gtg           1824
Glu Glu Gln Phe Asn Ser Thr Tyr Arg Val Val Ser Val Leu Thr Val
        595                 600                 605 ctg cac cag gac tgg ctg aac ggc aaa gaa tac aag tgc aag gtg tcc           1872
Leu His Gln Asp Trp Leu Asn Gly Lys Glu Tyr Lys Cys Lys Val Ser
    610                 615                 620 aac aag ggc ctg ccc agc agc atc gaa aag acc atc agc aag gcc aag           1920
Asn Lys Gly Leu Pro Ser Ser Ile Glu Lys Thr Ile Ser Lys Ala Lys
625                 630                 635                 640 ggc cag cct cgc gag ccc cag gtg tac acc ctg cct ccc tcc cag gaa           1968
Gly Gln Pro Arg Glu Pro Gln Val Tyr Thr Leu Pro Pro Ser Gln Glu
                645                 650                 655 gag atg acc aag aac cag gtg tcc ctg acc tgc ctg gtg aag ggc ttc           2016
Glu Met Thr Lys Asn Gln Val Ser Leu Thr Cys Leu Val Lys Gly Phe
            660                 665                 670 tac ccc agc gac atc gcc gtg gag tgg gag agc aac ggc cag cct gag           2064
Tyr Pro Ser Asp Ile Ala Val Glu Trp Glu Ser Asn Gly Gln Pro Glu
        675                 680                 685 aac aac tac aag acc acc cct ccc gtg ctg gac agc gac ggc agc ttc           2112
Asn Asn Tyr Lys Thr Thr Pro Pro Val Leu Asp Ser Asp Gly Ser Phe
    690                 695                 700 ttc ctg tac agc cgg ctg acc gtg gac aag agc cgg tgg cag gaa ggc           2160
Phe Leu Tyr Ser Arg Leu Thr Val Asp Lys Ser Arg Trp Gln Glu Gly
705                 710                 715                 720 aac gtc ttt agc tgc agc gtg atg cac gag gcc ctg cac aac cac tac           2208
Asn Val Phe Ser Cys Ser Val Met His Glu Ala Leu His Asn His Tyr
                725                 730                 735 acc cag aag agc ctg agc ctg tcc ctg ggc aag atg ttc tgg gtg ctg           2256
Thr Gln Lys Ser Leu Ser Leu Ser Leu Gly Lys Met Phe Trp Val Leu
            740                 745                 750 gtg gtg gtg ggc ggg gtg ctg gcc tgc tac agc ctg ctg gtg aca gtg           2304
Val Val Val Gly Gly Val Leu Ala Cys Tyr Ser Leu Leu Val Thr Val
        755                 760                 765 gcc ttc atc atc ttt tgg gtg cgg agc aag cgg agc aga ggc ggc cac           2352
Ala Phe Ile Ile Phe Trp Val Arg Ser Lys Arg Ser Arg Gly Gly His
    770                 775                 780 agc gac tac atg aac atg acc ccc aga cgg cct ggc ccc acc cgg aag           2400
Ser Asp Tyr Met Asn Met Thr Pro Arg Arg Pro Gly Pro Thr Arg Lys
785                 790                 795                 800 cac tac cag ccc tac gcc cca ccc agg gac ttt gcc gcc tac aga agc           2448
His Tyr Gln Pro Tyr Ala Pro Pro Arg Asp Phe Ala Ala Tyr Arg Ser
                805                 810                 815 aaa cgg ggc aga aag aaa ctc ctg tat ata ttc aaa caa cca ttt atg           2496
Lys Arg Gly Arg Lys Lys Leu Leu Tyr Ile Phe Lys Gln Pro Phe Met
            820                 825                 830 aga cca gta caa act act caa gag gaa gat ggc tgt agc tgc cga ttt           2544
Arg Pro Val Gln Thr Thr Gln Glu Glu Asp Gly Cys Ser Cys Arg Phe
        835                 840                 845 cca gaa gaa gaa gaa gga gga tgt gaa ctg cgg gtg aag ttc agc aga           2592
Pro Glu Glu Glu Glu Gly Gly Cys Glu Leu Arg Val Lys Phe Ser Arg
    850                 855                 860 agc gcc gac gcc cct gcc tac cag cag ggc cag aat cag ctg tac aac           2640
Ser Ala Asp Ala Pro Ala Tyr Gln Gln Gly Gln Asn Gln Leu Tyr Asn
865                 870                 875                 880
```

```
gag ctg aac ctg ggc aga agg gaa gag tac gac gtc ctg gat aag cgg        2688
Glu Leu Asn Leu Gly Arg Arg Glu Glu Tyr Asp Val Leu Asp Lys Arg
                885                 890                 895 aga ggc cgg gac cct gag atg ggc ggc aag cct cgg cgg aag aac ccc        2736
Arg Gly Arg Asp Pro Glu Met Gly Gly Lys Pro Arg Arg Lys Asn Pro
    900                 905                 910 cag gaa ggc ctg tat aac gaa ctg cag aaa gac aag atg gcc gag gcc        2784
Gln Glu Gly Leu Tyr Asn Glu Leu Gln Lys Asp Lys Met Ala Glu Ala
915                 920                 925 tac agc gag atc ggc atg aag ggc gag cgg agg cgg ggc aag ggc cac        2832
Tyr Ser Glu Ile Gly Met Lys Gly Glu Arg Arg Arg Gly Lys Gly His
            930                 935                 940 gac ggc ctg tat cag ggc ctg tcc acc gcc acc aag gat acc tac gac        2880
Asp Gly Leu Tyr Gln Gly Leu Ser Thr Ala Thr Lys Asp Thr Tyr Asp
945                 950                 955                 960 gcc ctg cac atg cag gcc ctg ccc cca agg                                2910
Ala Leu His Met Gln Ala Leu Pro Pro Arg
                965                 970

<210> SEQ ID NO 9
<211> LENGTH: 970
<212> TYPE: PRT
<213> ORGANISM: Artificial Sequence
<220> FEATURE:
<223> OTHER INFORMATION: Synthetic Construct

<400> SEQUENCE: 9

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240
```

```
Tyr Cys Ala Lys His Tyr Tyr Gly Gly Ser Tyr Ala Met Asp Tyr
                245                 250                 255

Trp Gly Gln Gly Thr Ser Val Thr Val Ser Ser Gly Gly Gly Ser
            260                 265                 270

Glu Val Gln Leu Gln Gln Ser Gly Ala Glu Leu Val Lys Pro Gly Ala
        275                 280                 285

Ser Val Lys Met Ser Cys Lys Ala Ser Gly Tyr Thr Phe Thr Ser Tyr
    290                 295                 300

Asn Met His Trp Val Lys Gln Thr Pro Gly Gln Gly Leu Glu Trp Ile
305                 310                 315                 320

Gly Ala Ile Tyr Pro Gly Asn Gly Asp Thr Ser Tyr Asn Gln Lys Phe
                325                 330                 335

Lys Gly Lys Ala Thr Leu Thr Ala Asp Lys Ser Ser Thr Ala Tyr
            340                 345                 350

Met Gln Leu Ser Ser Leu Thr Ser Glu Asp Ser Ala Asp Tyr Tyr Cys
        355                 360                 365

Ala Arg Ser Asn Tyr Tyr Gly Ser Ser Tyr Trp Phe Phe Asp Val Trp
    370                 375                 380

Gly Ala Gly Thr Thr Val Thr Val Ser Ser Gly Ser Thr Ser Gly Gly
385                 390                 395                 400

Gly Ser Gly Gly Gly Ser Gly Gly Gly Ser Ser Asp Ile Val Leu
                405                 410                 415

Thr Gln Ser Pro Ala Ile Leu Ser Ala Ser Pro Gly Glu Lys Val Thr
        420                 425                 430

Met Thr Cys Arg Ala Ser Ser Ser Val Asn Tyr Met Asp Trp Tyr Gln
    435                 440                 445

Lys Lys Pro Gly Ser Ser Pro Lys Pro Trp Ile Tyr Ala Thr Ser Asn
450                 455                 460

Leu Ala Ser Gly Val Pro Ala Arg Phe Ser Gly Ser Gly Ser Gly Thr
465                 470                 475                 480

Ser Tyr Ser Leu Thr Ile Ser Arg Val Glu Ala Glu Asp Ala Ala Thr
                485                 490                 495

Tyr Tyr Cys Gln Gln Trp Ser Phe Asn Pro Pro Thr Phe Gly Gly Gly
        500                 505                 510

Thr Lys Leu Glu Ile Lys Glu Ser Lys Tyr Gly Pro Pro Cys Pro Pro
    515                 520                 525

Cys Pro Ala Pro Glu Phe Leu Gly Gly Pro Ser Val Phe Leu Phe Pro
    530                 535                 540

Pro Lys Pro Lys Asp Thr Leu Met Ile Ser Arg Thr Pro Glu Val Thr
545                 550                 555                 560

Cys Val Val Val Asp Val Ser Gln Glu Asp Pro Glu Val Gln Phe Asn
                565                 570                 575

Trp Tyr Val Asp Gly Val Glu Val His Asn Ala Lys Thr Lys Pro Arg
            580                 585                 590

Glu Glu Gln Phe Asn Ser Thr Tyr Arg Val Val Ser Val Leu Thr Val
        595                 600                 605

Leu His Gln Asp Trp Leu Asn Gly Lys Glu Tyr Lys Cys Lys Val Ser
    610                 615                 620

Asn Lys Gly Leu Pro Ser Ser Ile Glu Lys Thr Ile Ser Lys Ala Lys
625                 630                 635                 640

Gly Gln Pro Arg Glu Pro Gln Val Tyr Thr Leu Pro Pro Ser Gln Glu
                645                 650                 655

Glu Met Thr Lys Asn Gln Val Ser Leu Thr Cys Leu Val Lys Gly Phe
```

```
                 660              665              670
Tyr Pro Ser Asp Ile Ala Val Glu Trp Glu Ser Asn Gly Gln Pro Glu
            675              680              685

Asn Asn Tyr Lys Thr Thr Pro Pro Val Leu Asp Ser Asp Gly Ser Phe
            690              695              700

Phe Leu Tyr Ser Arg Leu Thr Val Asp Lys Ser Arg Trp Gln Glu Gly
705              710              715              720

Asn Val Phe Ser Cys Ser Val Met His Glu Ala Leu His Asn His Tyr
            725              730              735

Thr Gln Lys Ser Leu Ser Leu Ser Leu Gly Lys Met Phe Trp Val Leu
            740              745              750

Val Val Val Gly Gly Val Leu Ala Cys Tyr Ser Leu Leu Val Thr Val
            755              760              765

Ala Phe Ile Ile Phe Trp Val Arg Ser Lys Arg Ser Arg Gly Gly His
            770              775              780

Ser Asp Tyr Met Asn Met Thr Pro Arg Arg Pro Gly Pro Thr Arg Lys
785              790              795              800

His Tyr Gln Pro Tyr Ala Pro Pro Arg Asp Phe Ala Ala Tyr Arg Ser
            805              810              815

Lys Arg Gly Arg Lys Lys Leu Leu Tyr Ile Phe Lys Gln Pro Phe Met
            820              825              830

Arg Pro Val Gln Thr Thr Gln Glu Glu Asp Gly Cys Ser Cys Arg Phe
            835              840              845

Pro Glu Glu Glu Glu Gly Gly Cys Glu Leu Arg Val Lys Phe Ser Arg
            850              855              860

Ser Ala Asp Ala Pro Ala Tyr Gln Gln Gly Gln Asn Gln Leu Tyr Asn
865              870              875              880

Glu Leu Asn Leu Gly Arg Arg Glu Glu Tyr Asp Val Leu Asp Lys Arg
            885              890              895

Arg Gly Arg Asp Pro Glu Met Gly Gly Lys Pro Arg Arg Lys Asn Pro
            900              905              910

Gln Glu Gly Leu Tyr Asn Glu Leu Gln Lys Asp Lys Met Ala Glu Ala
            915              920              925

Tyr Ser Glu Ile Gly Met Lys Gly Glu Arg Arg Arg Gly Lys Gly His
            930              935              940

Asp Gly Leu Tyr Gln Gly Leu Ser Thr Ala Thr Lys Asp Thr Tyr Asp
945              950              955              960

Ala Leu His Met Gln Ala Leu Pro Pro Arg
            965              970

<210> SEQ ID NO 10
<211> LENGTH: 3402
<212> TYPE: DNA
<213> ORGANISM: Artificial Sequence
<220> FEATURE:
<223> OTHER INFORMATION:
      GMCSFRss-CD19scFv-Gly4serlinker-CD20scFv-CD8alphaHinge-CD8alphaTM
      -41BB-CD3Zeta-T2A-EGFRt

<400> SEQUENCE: 10
atgctgctgc tggtgaccag cctgctgctg tgcgagctgc ccaccccgc ctttctgctg      60 atccccgaca tccagatgac ccagaccacc tccagcctga gcgccagcct gggcgaccgg    120
gtgaccatca gctgccgggc cagccaggac atcagcaagt acctgaactg gtatcagcag    180
aagcccgacg gcaccgtcaa gctgctgatc taccacacca gccggctgca cagcggcgtg    240
```

```
cccagccggt ttagcggcag cggctccggc accgactaca gcctgaccat ctccaacctg    300
gaacaggaag atatcgccac ctactttgc cagcagggca acacactgcc ctacaccttt    360
ggcggcggaa caaagctgga aatcaccggc agcacctccg gcagcggcaa gcctggcagc    420
ggcgagggca gcaccaaggg cgaggtgaag ctgcaggaaa gcggccctgg cctggtggcc    480
cccagccaga gcctgagcgt gacctgcacc gtgagcggcg tgagcctgcc cgactacggc    540
gtgagctgga tccggcagcc ccccaggaag ggcctggaat ggctgggcgt gatctggggc    600
agcgagacca cctactacaa cagcgccctg aagagccggc tgaccatcat caaggacaac    660
agcaagagcc aggtgttcct gaagatgaac agcctgcaga ccgacgacac cgccatctac    720
tactgcgcca agcactacta ctacggcggc agctacgcca tggactactg gggccagggc    780
accagcgtga ccgtgagcag cggaggtggt ggatccgagg tgcagctgca gcagtctggg    840
gctgagctgg tgaagcctgg ggcctcagtg aagatgtcct gcaaggcttc tggctacaca    900
tttaccagtt acaatatgca ctgggtaaag cagacacctg gacagggcct ggaatggatt    960
ggagctattt atccaggaaa tggtgatact tcctacaatc agaagttcaa aggcaaggcc   1020
acattgactg cagacaaatc ctccagcaca gcctacatgc agctcagcag cctgacatct   1080
gaggactctg cggactatta ctgtgcaaga tctaattatt acggtagtag ctactggttc   1140
ttcgatgtct ggggcgcagg gaccacggtc accgtctcct caggcagtac tagcggtggt   1200
ggctccgggg gcggttccgg tggggcggc agcagcgaca ttgtgctgac ccaatctcca   1260
gctatcctgt ctgcatctcc aggggagaag gtcacaatga cttgcagggc cagctcaagt   1320
gtaaattaca tggactggta ccagaagaag ccaggatcct cccccaaacc ctggatttat   1380
gccacatcca acctggcttc tggagtccct gctcgcttca gtggcagtgg gtctgggacc   1440
tcttactctc tcacaatcag cagagtggag gctgaagatg ctgccactta ttactgccag   1500
cagtggagtt ttaatccacc cacgttcgga gggggacca agctggaaat aaaagagagc   1560
aagtacggac cgcccgcccc ccttgcccct aagcctacca ccaccctgc ccctagacct   1620 ccaacacccg ccccaacaat cgccagccag cctctgtctc tgaggcccga ggcttgtaga   1680
ccagctgctg gcggagccgt gcacaccaga ggactggatt tcgcctgcga catctacatc   1740
tgggcccctc tggccggcac atgtggcgtg ctgctgctga gcctcgtgat caccaagcgg   1800
ggcagaaaga aactgctgta catctttaag cagcccttca tgcggcccgt gcagaccacc   1860
caggaagagg acggctgctc ctgcagattc cccgaggaag aagaaggcgg ctgcgagctg   1920
agagtgaagt tcagcagatc cgccgacgcc cctgcctacc agcagggaca gaaccagctg   1980
tacaacgagc tgaacctggg cagacgggaa gagtacgacg tgctggacaa gcggagaggc   2040
cgggaccctg agatgggcgg aaagcccaga agaaagaacc cccaggaagg cctgtataac   2100
gaactgcaga aagacaagat ggccgaggcc tacagcgaga tcggaatgaa gggcgagcgg   2160
agaagaggca aggccacga tggcctgtac cagggcctga gcaccgccac caaggacacc   2220
tatgacgccc tgcacatgca ggccctgcct ccaagactcg agggcggcgg agagggcaga   2280
ggaagtcttc taacatgcgg tgacgtggag gagaatcccg gccctaggat gcttctcctg   2340
gtgacaagcc ttctgctctg tgagttacca cacccagcat tcctcctgat cccacgcaaa   2400
gtgtgtaacg gaataggtat tggtgaattt aaagactcac tctccataaa tgctacgaat   2460
attaaacact tcaaaaactg cacctccatc agtggcgatc tccacatcct gccggtggca   2520 tttagggggtg actccttcac acatactcct cctctggatc cacaggaact ggatattctg   2580
aaaaccgtaa aggaaatcac aggggttttg ctgattcagg cttggcctga aaacaggacg   2640
```

-continued

```
gacctccatg cctttgagaa cctagaaatc atacgcggca ggaccaagca acatggtcag      2700
ttttctcttg cagtcgtcag cctgaacata acatccttgg gattacgctc cctcaaggag      2760
ataagtgatg gagatgtgat aatttcagga acaaaaatt tgtgctatgc aaatacaata      2820
aactggaaaa aactgtttgg gacctccggt cagaaaacca aaattataag caacagaggt      2880
gaaaacagct gcaaggccac aggccaggtc tgccatgcct tgtgctcccc cgagggctgc      2940
tggggcccgg agcccaggga ctgcgtctct gccggaatg tcagccgagg cagggaatgc      3000
gtggacaagt gcaaccttct ggagggtgag ccaagggagt tgtggagaa ctctgagtgc      3060 atacagtgcc acccagagtg cctgcctcag gccatgaaca tcacctgcac aggacgggga      3120
ccagacaact gtatccagtg tgcccactac attgacggcc ccactgcgt caagacctgc      3180 ccggcaggag tcatgggaga aaacaacacc ctggtctgga gtacgcaga cgccggccat      3240 gtgtgccacc tgtgccatcc aaactgcacc tacggatgca ctgggccagg tcttgaaggc      3300
tgtccaacga atgggcctaa gatcccgtcc atcgccactg gatggtggg ggccctcctc      3360 ttgctgctgg tggtggccct ggggatcggc ctcttcatgt ga                        3402
```

<210> SEQ ID NO 11
<211> LENGTH: 3402
<212> TYPE: DNA
<213> ORGANISM: Artificial Sequence
<220> FEATURE:
<223> OTHER INFORMATION:
    GMCSFRss-CD19scFv-Gly4serlinker-CD20scFv-CD8alphaHinge-CD8alphaTM
    -41BB-CD3Zeta-T2A-EGFRt
<220> FEATURE:
<221> NAME/KEY: CDS
<222> LOCATION: (1)..(3402)

<400> SEQUENCE: 11

```
atg ctg ctg ctg gtg acc agc ctg ctg ctg tgc gag ctg ccc cac ccc       48
Met Leu Leu Leu Val Thr Ser Leu Leu Leu Cys Glu Leu Pro His Pro
1               5                   10                  15 gcc ttt ctg ctg atc ccc gac atc cag atg acc cag acc acc tcc agc       96
Ala Phe Leu Leu Ile Pro Asp Ile Gln Met Thr Gln Thr Thr Ser Ser
            20                  25                  30 ctg agc gcc agc ctg ggc gac cgg gtg acc atc agc tgc cgg gcc agc      144
Leu Ser Ala Ser Leu Gly Asp Arg Val Thr Ile Ser Cys Arg Ala Ser
        35                  40                  45 cag gac atc agc aag tac ctg aac tgg tat cag cag aag ccc gac ggc      192
Gln Asp Ile Ser Lys Tyr Leu Asn Trp Tyr Gln Gln Lys Pro Asp Gly
    50                  55                  60 acc gtc aag ctg ctg atc tac cac acc agc cgg ctg cac agc ggc gtg      240
Thr Val Lys Leu Leu Ile Tyr His Thr Ser Arg Leu His Ser Gly Val
65                  70                  75                  80 ccc agc cgg ttt agc ggc agc ggc tcc ggc acc gac tac agc ctg acc      288
Pro Ser Arg Phe Ser Gly Ser Gly Ser Gly Thr Asp Tyr Ser Leu Thr
                85                  90                  95 atc tcc aac ctg gaa cag gaa gat atc gcc acc tac ttt tgc cag cag      336
Ile Ser Asn Leu Glu Gln Glu Asp Ile Ala Thr Tyr Phe Cys Gln Gln
            100                 105                 110 ggc aac aca ctg ccc tac acc ttt ggc ggc gga aca aag ctg gaa atc      384
Gly Asn Thr Leu Pro Tyr Thr Phe Gly Gly Gly Thr Lys Leu Glu Ile
        115                 120                 125 acc ggc agc acc tcc ggc agc ggc aag cct ggc agc ggc gag ggc agc      432
Thr Gly Ser Thr Ser Gly Ser Gly Lys Pro Gly Ser Gly Glu Gly Ser
    130                 135                 140 acc aag ggc gag gtg aag ctg cag gaa agc ggc cct ggc ctg gtg gcc      480
```

```
             Thr Lys Gly Glu Val Lys Leu Gln Glu Ser Gly Pro Gly Leu Val Ala
             145             150                 155                 160 ccc agc cag agc ctg agc gtg acc tgc acc gtg agc ggc gtg agc ctg            528
Pro Ser Gln Ser Leu Ser Val Thr Cys Thr Val Ser Gly Val Ser Leu
                165                 170                 175 ccc gac tac ggc gtg agc tgg atc cgg cag ccc ccc agg aag ggc ctg            576
Pro Asp Tyr Gly Val Ser Trp Ile Arg Gln Pro Pro Arg Lys Gly Leu
                180                 185                 190 gaa tgg ctg ggc gtg atc tgg ggc agc gag acc acc tac tac aac agc            624
Glu Trp Leu Gly Val Ile Trp Gly Ser Glu Thr Thr Tyr Tyr Asn Ser
                195                 200                 205 gcc ctg aag agc cgg ctg acc atc atc aag gac aac agc aag agc cag            672
Ala Leu Lys Ser Arg Leu Thr Ile Ile Lys Asp Asn Ser Lys Ser Gln
210                 215                 220 gtg ttc ctg aag atg aac agc ctg cag acc gac gac acc gcc atc tac            720
Val Phe Leu Lys Met Asn Ser Leu Gln Thr Asp Asp Thr Ala Ile Tyr
225                 230                 235                 240 tac tgc gcc aag cac tac tac tac ggc ggc agc tac gcc atg gac tac            768
Tyr Cys Ala Lys His Tyr Tyr Tyr Gly Gly Ser Tyr Ala Met Asp Tyr
                245                 250                 255 tgg ggc cag ggc acc agc gtg acc gtg agc agc gga ggt ggt gga tcc            816
Trp Gly Gln Gly Thr Ser Val Thr Val Ser Ser Gly Gly Gly Gly Ser
                260                 265                 270 gag gtg cag ctg cag cag tct ggg gct gag ctg gtg aag cct ggg gcc            864
Glu Val Gln Leu Gln Gln Ser Gly Ala Glu Leu Val Lys Pro Gly Ala
                275                 280                 285 tca gtg aag atg tcc tgc aag gct tct ggc tac aca ttt acc agt tac            912
Ser Val Lys Met Ser Cys Lys Ala Ser Gly Tyr Thr Phe Thr Ser Tyr
290                 295                 300 aat atg cac tgg gta aag cag aca cct gga cag ggc ctg gaa tgg att            960
Asn Met His Trp Val Lys Gln Thr Pro Gly Gln Gly Leu Glu Trp Ile
305                 310                 315                 320 gga gct att tat cca gga aat ggt gat act tcc tac aat cag aag ttc           1008
Gly Ala Ile Tyr Pro Gly Asn Gly Asp Thr Ser Tyr Asn Gln Lys Phe
                325                 330                 335 aaa ggc aag gcc aca ttg act gca gac aaa tcc tcc agc aca gcc tac           1056
Lys Gly Lys Ala Thr Leu Thr Ala Asp Lys Ser Ser Ser Thr Ala Tyr
                340                 345                 350 atg cag ctc agc agc ctg aca tct gag gac tct gcg gac tat tac tgt           1104
Met Gln Leu Ser Ser Leu Thr Ser Glu Asp Ser Ala Asp Tyr Tyr Cys
                355                 360                 365 gca aga tct aat tat tac ggt agt agc tac tgg ttc ttc gat gtc tgg           1152
Ala Arg Ser Asn Tyr Tyr Gly Ser Ser Tyr Trp Phe Phe Asp Val Trp
370                 375                 380 ggc gca ggg acc acg gtc acc gtc tcc tca ggc agt act agc ggt ggt           1200
Gly Ala Gly Thr Thr Val Thr Val Ser Ser Gly Ser Thr Ser Gly Gly
385                 390                 395                 400 ggc tcc ggg ggc ggt tcc ggt ggg ggc ggc agc agc gac att gtg ctg           1248
Gly Ser Gly Gly Gly Ser Gly Gly Gly Gly Ser Ser Asp Ile Val Leu
                405                 410                 415 acc caa tct cca gct atc ctg tct gca tct cca ggg gag aag gtc aca           1296
Thr Gln Ser Pro Ala Ile Leu Ser Ala Ser Pro Gly Glu Lys Val Thr
                420                 425                 430 atg act tgc agg gcc agc tca agt gta aat tac atg gac tgg tac cag           1344
Met Thr Cys Arg Ala Ser Ser Ser Val Asn Tyr Met Asp Trp Tyr Gln
                435                 440                 445 aag aag cca gga tcc tcc ccc aaa ccc tgg att tat gcc aca tcc aac           1392
Lys Lys Pro Gly Ser Ser Pro Lys Pro Trp Ile Tyr Ala Thr Ser Asn
450                 455                 460
```

```
ctg gct tct gga gtc cct gct cgc ttc agt ggc agt ggg tct ggg acc    1440
Leu Ala Ser Gly Val Pro Ala Arg Phe Ser Gly Ser Gly Ser Gly Thr
465                 470                 475                 480 tct tac tct ctc aca atc agc aga gtg gag gct gaa gat gct gcc act    1488
Ser Tyr Ser Leu Thr Ile Ser Arg Val Glu Ala Glu Asp Ala Ala Thr
                485                 490                 495 tat tac tgc cag cag tgg agt ttt aat cca ccc acg ttc gga ggg ggg    1536
Tyr Tyr Cys Gln Gln Trp Ser Phe Asn Pro Pro Thr Phe Gly Gly Gly
            500                 505                 510 acc aag ctg gaa ata aaa gag agc aag tac gga ccg ccc tgc ccc cct    1584
Thr Lys Leu Glu Ile Lys Glu Ser Lys Tyr Gly Pro Pro Cys Pro Pro
        515                 520                 525 tgc cct aag cct acc acc acc cct gcc cct aga cct cca aca ccc gcc    1632
Cys Pro Lys Pro Thr Thr Thr Pro Ala Pro Arg Pro Pro Thr Pro Ala
    530                 535                 540 cca aca atc gcc agc cag cct ctg tct ctg agg ccc gag gct tgt aga    1680
Pro Thr Ile Ala Ser Gln Pro Leu Ser Leu Arg Pro Glu Ala Cys Arg
545                 550                 555                 560 cca gct gct ggg gga gcc gtg cac acc aga gga ctg gat ttc gcc tgc    1728
Pro Ala Ala Gly Gly Ala Val His Thr Arg Gly Leu Asp Phe Ala Cys
                565                 570                 575 gac atc tac atc tgg gcc cct ctg gcc ggc aca tgt ggc gtg ctg ctg    1776
Asp Ile Tyr Ile Trp Ala Pro Leu Ala Gly Thr Cys Gly Val Leu Leu
            580                 585                 590 ctg agc ctc gtg atc acc aag cgg ggc aga aag aaa ctg ctg tac atc    1824
Leu Ser Leu Val Ile Thr Lys Arg Gly Arg Lys Lys Leu Leu Tyr Ile
        595                 600                 605 ttt aag cag ccc ttc atg cgg ccc gtg cag acc acc cag gaa gag gac    1872
Phe Lys Gln Pro Phe Met Arg Pro Val Gln Thr Thr Gln Glu Glu Asp
    610                 615                 620 ggc tgc tcc tgc aga ttc ccc gag gaa gaa gaa ggc ggc tgc gag ctg    1920
Gly Cys Ser Cys Arg Phe Pro Glu Glu Glu Glu Gly Gly Cys Glu Leu
625                 630                 635                 640 aga gtg aag ttc agc aga tcc gcc gac gcc cct gcc tac cag cag gga    1968
Arg Val Lys Phe Ser Arg Ser Ala Asp Ala Pro Ala Tyr Gln Gln Gly
                645                 650                 655 cag aac cag ctg tac aac gag ctg aac ctg ggc aga cgg gaa gag tac    2016
Gln Asn Gln Leu Tyr Asn Glu Leu Asn Leu Gly Arg Arg Glu Glu Tyr
            660                 665                 670 gac gtg ctg gac aag cgg aga ggc cgg gac cct gag atg ggc gga aag    2064
Asp Val Leu Asp Lys Arg Arg Gly Arg Asp Pro Glu Met Gly Gly Lys
        675                 680                 685 ccc aga aga aag aac ccc cag gaa ggc ctg tat aac gaa ctg cag aaa    2112
Pro Arg Arg Lys Asn Pro Gln Glu Gly Leu Tyr Asn Glu Leu Gln Lys
    690                 695                 700 gac aag atg gcc gag gcc tac agc gag atc gga atg aag ggc gag cgg    2160
Asp Lys Met Ala Glu Ala Tyr Ser Glu Ile Gly Met Lys Gly Glu Arg
705                 710                 715                 720 aga aga ggc aag ggc cac gat ggc ctg tac cag ggc ctg agc acc gcc    2208
Arg Arg Gly Lys Gly His Asp Gly Leu Tyr Gln Gly Leu Ser Thr Ala
                725                 730                 735 acc aag gac acc tat gac gcc ctg cac atg cag gcc ctg cct cca aga    2256
Thr Lys Asp Thr Tyr Asp Ala Leu His Met Gln Ala Leu Pro Pro Arg
            740                 745                 750 ctc gag ggc ggc gga gag ggc aga gga agt ctt cta aca tgc ggt gac    2304
Leu Glu Gly Gly Gly Glu Gly Arg Gly Ser Leu Leu Thr Cys Gly Asp
        755                 760                 765 gtg gag gag aat ccc ggc cct agg atg ctt ctc ctg gtg aca agc ctt    2352
Val Glu Glu Asn Pro Gly Pro Arg Met Leu Leu Leu Val Thr Ser Leu
    770                 775                 780
```

-continued

```
ctg ctc tgt gag tta cca cac cca gca ttc ctc ctg atc cca cgc aaa      2400
Leu Leu Cys Glu Leu Pro His Pro Ala Phe Leu Leu Ile Pro Arg Lys
785                 790                 795                 800 gtg tgt aac gga ata ggt att ggt gaa ttt aaa gac tca ctc tcc ata      2448
Val Cys Asn Gly Ile Gly Ile Gly Glu Phe Lys Asp Ser Leu Ser Ile
                805                 810                 815 aat gct acg aat att aaa cac ttc aaa aac tgc acc tcc atc agt ggc      2496
Asn Ala Thr Asn Ile Lys His Phe Lys Asn Cys Thr Ser Ile Ser Gly
        820                 825                 830 gat ctc cac atc ctg ccg gtg gca ttt agg ggt gac tcc ttc aca cat      2544
Asp Leu His Ile Leu Pro Val Ala Phe Arg Gly Asp Ser Phe Thr His
835                 840                 845 act cct cct ctg gat cca cag gaa ctg gat att ctg aaa acc gta aag      2592
Thr Pro Pro Leu Asp Pro Gln Glu Leu Asp Ile Leu Lys Thr Val Lys
    850                 855                 860 gaa atc aca ggg ttt ttg ctg att cag gct tgg cct gaa aac agg acg      2640
Glu Ile Thr Gly Phe Leu Leu Ile Gln Ala Trp Pro Glu Asn Arg Thr
865                 870                 875                 880 gac ctc cat gcc ttt gag aac cta gaa atc ata cgc ggc agg acc aag      2688
Asp Leu His Ala Phe Glu Asn Leu Glu Ile Ile Arg Gly Arg Thr Lys
                885                 890                 895 caa cat ggt cag ttt tct ctt gca gtc gtc agc ctg aac ata aca tcc      2736
Gln His Gly Gln Phe Ser Leu Ala Val Val Ser Leu Asn Ile Thr Ser
        900                 905                 910 ttg gga tta cgc tcc ctc aag gag ata agt gat gga gat gtg ata att      2784
Leu Gly Leu Arg Ser Leu Lys Glu Ile Ser Asp Gly Asp Val Ile Ile
915                 920                 925 tca gga aac aaa aat ttg tgc tat gca aat aca ata aac tgg aaa aaa      2832
Ser Gly Asn Lys Asn Leu Cys Tyr Ala Asn Thr Ile Asn Trp Lys Lys
    930                 935                 940 ctg ttt ggg acc tcc ggt cag aaa acc aaa att ata agc aac aga ggt      2880
Leu Phe Gly Thr Ser Gly Gln Lys Thr Lys Ile Ile Ser Asn Arg Gly
945                 950                 955                 960 gaa aac agc tgc aag gcc aca ggc cag gtc tgc cat gcc ttg tgc tcc      2928
Glu Asn Ser Cys Lys Ala Thr Gly Gln Val Cys His Ala Leu Cys Ser
                965                 970                 975 ccc gag ggc tgc tgg ggc ccg gag ccc agg gac tgc gtc tct tgc cgg      2976
Pro Glu Gly Cys Trp Gly Pro Glu Pro Arg Asp Cys Val Ser Cys Arg
        980                 985                 990 aat gtc agc cga ggc agg gaa tgc gtg gac aag tgc aac ctt ctg gag      3024
Asn Val Ser Arg Gly Arg Glu Cys Val Asp Lys Cys Asn Leu Leu Glu
    995                 1000                1005 ggt gag cca agg gag ttt gtg gag aac tct gag tgc ata cag tgc           3069
Gly Glu Pro Arg Glu Phe Val Glu Asn Ser Glu Cys Ile Gln Cys
        1010                1015                1020 cac cca gag tgc ctg cct cag gcc atg aac atc acc tgc aca gga           3114
His Pro Glu Cys Leu Pro Gln Ala Met Asn Ile Thr Cys Thr Gly
    1025                1030                1035 cgg gga cca gac aac tgt atc cag tgt gcc cac tac att gac ggc           3159
Arg Gly Pro Asp Asn Cys Ile Gln Cys Ala His Tyr Ile Asp Gly
    1040                1045                1050 ccc cac tgc gtc aag acc tgc ccg gca gga gtc atg gga gaa aac           3204
Pro His Cys Val Lys Thr Cys Pro Ala Gly Val Met Gly Glu Asn
    1055                1060                1065 aac acc ctg gtc tgg aag tac gca gac gcc ggc cat gtg tgc cac           3249
Asn Thr Leu Val Trp Lys Tyr Ala Asp Ala Gly His Val Cys His
    1070                1075                1080 ctg tgc cat cca aac tgc acc tac gga tgc act ggg cca ggt ctt           3294
Leu Cys His Pro Asn Cys Thr Tyr Gly Cys Thr Gly Pro Gly Leu
```

|  |  |  |  | 1085 |  |  |  | 1090 |  |  |  | 1095 |  |  |
|---|---|---|---|---|---|---|---|---|---|---|---|---|---|---|

```
gaa  ggc  tgt  cca  acg  aat  ggg  cct  aag  atc  ccg  tcc  atc  gcc  act           3339
Glu  Gly  Cys  Pro  Thr  Asn  Gly  Pro  Lys  Ile  Pro  Ser  Ile  Ala  Thr
     1100                1105                    1110 ggg  atg  gtg  ggg  gcc  ctc  ctc  ttg  ctg  ctg  gtg  gtg  gcc  ctg  ggg           3384
Gly  Met  Val  Gly  Ala  Leu  Leu  Leu  Leu  Leu  Val  Val  Ala  Leu  Gly
     1115                1120                    1125 atc  ggc  ctc  ttc  atg  tga                                                         3402
Ile  Gly  Leu  Phe  Met
     1130
```

<210> SEQ ID NO 12
<211> LENGTH: 1133
<212> TYPE: PRT
<213> ORGANISM: Artificial Sequence
<220> FEATURE:
<223> OTHER INFORMATION: Synthetic Construct

<400> SEQUENCE: 12

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Gly Gly Gly Gly Ser
            260                 265                 270

Glu Val Gln Leu Gln Gln Ser Gly Ala Glu Leu Val Lys Pro Gly Ala
        275                 280                 285

Ser Val Lys Met Ser Cys Lys Ala Ser Gly Tyr Thr Phe Thr Ser Tyr
```

```
                290                 295                 300
Asn Met His Trp Val Lys Gln Thr Pro Gly Gln Gly Leu Glu Trp Ile
305                 310                 315                 320

Gly Ala Ile Tyr Pro Gly Asn Gly Asp Thr Ser Tyr Asn Gln Lys Phe
                325                 330                 335

Lys Gly Lys Ala Thr Leu Thr Ala Asp Lys Ser Ser Thr Ala Tyr
                340                 345                 350

Met Gln Leu Ser Ser Leu Thr Ser Glu Asp Ser Ala Asp Tyr Tyr Cys
                355                 360                 365

Ala Arg Ser Asn Tyr Tyr Gly Ser Ser Tyr Trp Phe Phe Asp Val Trp
                370                 375                 380

Gly Ala Gly Thr Thr Val Thr Val Ser Ser Gly Ser Thr Ser Gly Gly
385                 390                 395                 400

Gly Ser Gly Gly Gly Ser Gly Gly Gly Ser Ser Asp Ile Val Leu
                405                 410                 415

Thr Gln Ser Pro Ala Ile Leu Ser Ala Ser Pro Gly Glu Lys Val Thr
                420                 425                 430

Met Thr Cys Arg Ala Ser Ser Ser Val Asn Tyr Met Asp Trp Tyr Gln
                435                 440                 445

Lys Lys Pro Gly Ser Ser Pro Lys Pro Trp Ile Tyr Ala Thr Ser Asn
                450                 455                 460

Leu Ala Ser Gly Val Pro Ala Arg Phe Ser Gly Ser Gly Ser Gly Thr
465                 470                 475                 480

Ser Tyr Ser Leu Thr Ile Ser Arg Val Glu Ala Glu Asp Ala Ala Thr
                485                 490                 495

Tyr Tyr Cys Gln Gln Trp Ser Phe Asn Pro Pro Thr Phe Gly Gly Gly
                500                 505                 510

Thr Lys Leu Glu Ile Lys Glu Ser Lys Tyr Gly Pro Pro Cys Pro Pro
                515                 520                 525

Cys Pro Lys Pro Thr Thr Thr Pro Ala Pro Arg Pro Pro Thr Pro Ala
                530                 535                 540

Pro Thr Ile Ala Ser Gln Pro Leu Ser Leu Arg Pro Glu Ala Cys Arg
545                 550                 555                 560

Pro Ala Ala Gly Gly Ala Val His Thr Arg Gly Leu Asp Phe Ala Cys
                565                 570                 575

Asp Ile Tyr Ile Trp Ala Pro Leu Ala Gly Thr Cys Gly Val Leu Leu
                580                 585                 590

Leu Ser Leu Val Ile Thr Lys Arg Gly Arg Lys Lys Leu Leu Tyr Ile
                595                 600                 605

Phe Lys Gln Pro Phe Met Arg Pro Val Gln Thr Thr Gln Glu Glu Asp
610                 615                 620

Gly Cys Ser Cys Arg Phe Pro Glu Glu Glu Glu Gly Gly Cys Glu Leu
625                 630                 635                 640

Arg Val Lys Phe Ser Arg Ser Ala Asp Ala Pro Ala Tyr Gln Gln Gly
                645                 650                 655

Gln Asn Gln Leu Tyr Asn Glu Leu Asn Leu Gly Arg Arg Glu Glu Tyr
                660                 665                 670

Asp Val Leu Asp Lys Arg Gly Arg Asp Pro Glu Met Gly Gly Lys
                675                 680                 685

Pro Arg Arg Lys Asn Pro Gln Glu Gly Leu Tyr Asn Glu Leu Gln Lys
                690                 695                 700

Asp Lys Met Ala Glu Ala Tyr Ser Glu Ile Gly Met Lys Gly Glu Arg
705                 710                 715                 720
```

-continued

```
Arg Arg Gly Lys Gly His Asp Gly Leu Tyr Gln Gly Leu Ser Thr Ala
            725                 730                 735

Thr Lys Asp Thr Tyr Asp Ala Leu His Met Gln Ala Leu Pro Pro Arg
            740                 745                 750

Leu Glu Gly Gly Glu Gly Arg Gly Ser Leu Leu Thr Cys Gly Asp
            755                 760                 765

Val Glu Glu Asn Pro Gly Pro Arg Met Leu Leu Val Thr Ser Leu
770                 775                 780

Leu Leu Cys Glu Leu Pro His Pro Ala Phe Leu Leu Ile Pro Arg Lys
785             790                 795                 800

Val Cys Asn Gly Ile Gly Ile Gly Glu Phe Lys Asp Ser Leu Ser Ile
            805                 810                 815

Asn Ala Thr Asn Ile Lys His Phe Lys Asn Cys Thr Ser Ile Ser Gly
            820                 825                 830

Asp Leu His Ile Leu Pro Val Ala Phe Arg Gly Asp Ser Phe Thr His
            835                 840                 845

Thr Pro Pro Leu Asp Pro Gln Glu Leu Asp Ile Leu Lys Thr Val Lys
            850                 855                 860

Glu Ile Thr Gly Phe Leu Leu Ile Gln Ala Trp Pro Glu Asn Arg Thr
865                 870                 875                 880

Asp Leu His Ala Phe Glu Asn Leu Glu Ile Ile Arg Gly Arg Thr Lys
                885                 890                 895

Gln His Gly Gln Phe Ser Leu Ala Val Val Ser Leu Asn Ile Thr Ser
            900                 905                 910

Leu Gly Leu Arg Ser Leu Lys Glu Ile Ser Asp Gly Asp Val Ile Ile
            915                 920                 925

Ser Gly Asn Lys Asn Leu Cys Tyr Ala Asn Thr Ile Asn Trp Lys Lys
930                 935                 940

Leu Phe Gly Thr Ser Gly Gln Lys Thr Lys Ile Ile Ser Asn Arg Gly
945                 950                 955                 960

Glu Asn Ser Cys Lys Ala Thr Gly Gln Val Cys His Ala Leu Cys Ser
            965                 970                 975

Pro Glu Gly Cys Trp Gly Pro Glu Pro Arg Asp Cys Val Ser Cys Arg
            980                 985                 990

Asn Val Ser Arg Gly Arg Glu Cys Val Asp Lys Cys Asn Leu Leu Glu
            995                 1000                1005

Gly Glu Pro Arg Glu Phe Val Glu Asn Ser Glu Cys Ile Gln Cys
    1010                1015                1020

His Pro Glu Cys Leu Pro Gln Ala Met Asn Ile Thr Cys Thr Gly
    1025                1030                1035

Arg Gly Pro Asp Asn Cys Ile Gln Cys Ala His Tyr Ile Asp Gly
    1040                1045                1050

Pro His Cys Val Lys Thr Cys Pro Ala Gly Val Met Gly Glu Asn
    1055                1060                1065

Asn Thr Leu Val Trp Lys Tyr Ala Asp Ala Gly His Val Cys His
    1070                1075                1080

Leu Cys His Pro Asn Cys Thr Tyr Gly Cys Thr Gly Pro Gly Leu
    1085                1090                1095

Glu Gly Cys Pro Thr Asn Gly Pro Lys Ile Pro Ser Ile Ala Thr
    1100                1105                1110

Gly Met Val Gly Ala Leu Leu Leu Leu Val Val Ala Leu Gly
    1115                1120                1125
```

```
<210> SEQ ID NO 13
<211> LENGTH: 1146
<212> TYPE: DNA
<213> ORGANISM: Artificial Sequence
<220> FEATURE:
<223> OTHER INFORMATION: T2A-EGFRt

<400> SEQUENCE: 13
ctcgagggcg gcggagaggg cagaggaagt cttctaacat gcggtgacgt ggaggagaat      60
cccggcccta ggatgcttct cctggtgaca agccttctgc tctgtgagtt accacaccca     120
gcattcctcc tgatcccacg caaagtgtgt aacggaatag gtattggtga atttaaagac     180
tcactctcca taaatgctac gaatattaaa cacttcaaaa actgcacctc catcagtggc     240
gatctccaca tcctgccggt ggcatttagg ggtgactcct tcacacatac tcctcctctg     300
gatccacagg aactggatat tctgaaaacc gtaaaggaaa tcacagggtt tttgctgatt     360
caggcttggc ctgaaaacag gacggacctc catgcctttg agaacctaga aatcatacgc     420
ggcaggacca gcaacatgg tcagttttct cttgcagtcg tcagcctgaa cataacatcc     480
ttgggattac gctccctcaa ggagataagt gatggagatg tgataatttc aggaaacaaa     540
aatttgtgct atgcaaatac aataaactgg aaaaaactgt ttgggacctc cggtcagaaa     600
accaaaatta taagcaacag aggtgaaaac agctgcaagg ccacaggcca ggtctgccat     660
gccttgtgct cccccgaggg ctgctggggc ccggagccca gggactgcgt ctcttgccgg     720
aatgtcagcc gaggcaggga atgcgtggac aagtgcaacc ttctggaggg tgagccaagg     780
gagtttgtgg agaactctga gtgcatacag tgccacccag agtgcctgcc tcaggccatg     840
aacatcacct gcacaggacg ggaccagac aactgtatcc agtgtgccca ctacattgac     900
ggcccccact cgtcaagac ctgcccggca ggagtcatgg gagaaaacaa caccctggtc     960
tggaagtacg cagacgccgg ccatgtgtgc cacctgtgcc atccaaactg cacctacgga    1020
tgcactgggc aggtcttga aggctgtcca acgaatgggc taagatcccg tccatcgcc    1080
actgggatgg tgggggccct cctcttgctg ctggtggtgg ccctgggat cggcctcttc    1140
atgtga                                                              1146

<210> SEQ ID NO 14
<211> LENGTH: 1146
<212> TYPE: DNA
<213> ORGANISM: Artificial Sequence
<220> FEATURE:
<223> OTHER INFORMATION: T2A-EGFRt
<220> FEATURE:
<221> NAME/KEY: CDS
<222> LOCATION: (1)..(1146)

<400> SEQUENCE: 14 ctc gag ggc ggc gga gag ggc aga gga agt ctt cta aca tgc ggt gac       48
Leu Glu Gly Gly Gly Glu Gly Arg Gly Ser Leu Leu Thr Cys Gly Asp
 1               5                  10                  15 gtg gag gag aat ccc ggc cct agg atg ctt ctc ctg gtg aca agc ctt       96
Val Glu Glu Asn Pro Gly Pro Arg Met Leu Leu Leu Val Thr Ser Leu
             20                  25                  30 ctg ctc tgt gag tta cca cac cca gca ttc ctc ctg atc cca cgc aaa      144
Leu Leu Cys Glu Leu Pro His Pro Ala Phe Leu Leu Ile Pro Arg Lys
         35                  40                  45 gtg tgt aac gga ata ggt att ggt gaa ttt aaa gac tca ctc tcc ata      192
```

-continued

| | | | | | | | | | | | | |
|---|---|---|---|---|---|---|---|---|---|---|---|---|
| Val | Cys | Asn | Gly | Ile | Gly | Ile | Gly | Glu | Phe | Lys | Asp | Ser | Leu | Ser | Ile |
| | 50 | | | | | 55 | | | | 60 | | |

```
aat gct acg aat att aaa cac ttc aaa aac tgc acc tcc atc agt ggc     240
Asn Ala Thr Asn Ile Lys His Phe Lys Asn Cys Thr Ser Ile Ser Gly
 65              70                  75                  80 gat ctc cac atc ctg ccg gtg gca ttt agg ggt gac tcc ttc aca cat     288
Asp Leu His Ile Leu Pro Val Ala Phe Arg Gly Asp Ser Phe Thr His
                 85                  90                  95 act cct cct ctg gat cca cag gaa ctg gat att ctg aaa acc gta aag     336
Thr Pro Pro Leu Asp Pro Gln Glu Leu Asp Ile Leu Lys Thr Val Lys
            100                 105                 110 gaa atc aca ggg ttt ttg ctg att cag gct tgg cct gaa aac agg acg     384
Glu Ile Thr Gly Phe Leu Leu Ile Gln Ala Trp Pro Glu Asn Arg Thr
        115                 120                 125 gac ctc cat gcc ttt gag aac cta gaa atc ata cgc ggc agg acc aag     432
Asp Leu His Ala Phe Glu Asn Leu Glu Ile Ile Arg Gly Arg Thr Lys
    130                 135                 140 caa cat ggt cag ttt tct ctt gca gtc gtc agc ctg aac ata aca tcc     480
Gln His Gly Gln Phe Ser Leu Ala Val Val Ser Leu Asn Ile Thr Ser
145                 150                 155                 160 ttg gga tta cgc tcc ctc aag gag ata agt gat gga gat gta ata att     528
Leu Gly Leu Arg Ser Leu Lys Glu Ile Ser Asp Gly Asp Val Ile Ile
                165                 170                 175 tca gga aac aaa aat ttg tgc tat gca aat aca ata aac tgg aaa aaa     576
Ser Gly Asn Lys Asn Leu Cys Tyr Ala Asn Thr Ile Asn Trp Lys Lys
            180                 185                 190 ctg ttt ggg acc tcc ggt cag aaa acc aaa att ata agc aac aga ggt     624
Leu Phe Gly Thr Ser Gly Gln Lys Thr Lys Ile Ile Ser Asn Arg Gly
        195                 200                 205 gaa aac agc tgc aag gcc aca ggc cag gtc tgc cat gcc ttg tgc tcc     672
Glu Asn Ser Cys Lys Ala Thr Gly Gln Val Cys His Ala Leu Cys Ser
    210                 215                 220 ccc gag ggc tgc tgg ggc ccg gag ccc agg gac tgc gtc tct tgc cgg     720
Pro Glu Gly Cys Trp Gly Pro Glu Pro Arg Asp Cys Val Ser Cys Arg
225                 230                 235                 240 aat gtc agc cga ggc agg gaa tgc gtg gac aag tgc aac ctt ctg gag     768
Asn Val Ser Arg Gly Arg Glu Cys Val Asp Lys Cys Asn Leu Leu Glu
                245                 250                 255 ggt gag cca agg gag ttt gtg gag aac tct gag tgc ata cag tgc cac     816
Gly Glu Pro Arg Glu Phe Val Glu Asn Ser Glu Cys Ile Gln Cys His
            260                 265                 270 cca gag tgc ctg cct cag gcc atg aac atc acc tgc aca gga cgg gga     864
Pro Glu Cys Leu Pro Gln Ala Met Asn Ile Thr Cys Thr Gly Arg Gly
        275                 280                 285 cca gac aac tgt atc cag tgt gcc cac tac att gac ggc ccc cac tgc     912
Pro Asp Asn Cys Ile Gln Cys Ala His Tyr Ile Asp Gly Pro His Cys
    290                 295                 300 gtc aag acc tgc ccg gca gga gtc atg gga gaa aac aac acc ctg gtc     960
Val Lys Thr Cys Pro Ala Gly Val Met Gly Glu Asn Asn Thr Leu Val
305                 310                 315                 320 tgg aag tac gca gac gcc ggc cat gtg tgc cac ctg tgc cat cca aac    1008
Trp Lys Tyr Ala Asp Ala Gly His Val Cys His Leu Cys His Pro Asn
                325                 330                 335 tgc acc tac gga tgc act ggg cca ggt ctt gaa ggc tgt cca acg aat    1056
Cys Thr Tyr Gly Cys Thr Gly Pro Gly Leu Glu Gly Cys Pro Thr Asn
            340                 345                 350 ggg cct aag atc ccg tcc atc gcc act ggg atg gtg ggg gcc ctc ctc    1104
Gly Pro Lys Ile Pro Ser Ile Ala Thr Gly Met Val Gly Ala Leu Leu
        355                 360                 365
```

```
ttg ctg ctg gtg gtg gcc ctg ggg atc ggc ctc ttc atg tga           1146
Leu Leu Leu Val Val Ala Leu Gly Ile Gly Leu Phe Met
370                 375                 380
```

<210> SEQ ID NO 15
<211> LENGTH: 381
<212> TYPE: PRT
<213> ORGANISM: Artificial Sequence
<220> FEATURE:
<223> OTHER INFORMATION: Synthetic Construct

<400> SEQUENCE: 15

```
Leu Glu Gly Gly Gly Glu Gly Arg Gly Ser Leu Leu Thr Cys Gly Asp
1               5                   10                  15

Val Glu Glu Asn Pro Gly Pro Arg Met Leu Leu Leu Val Thr Ser Leu
            20                  25                  30

Leu Leu Cys Glu Leu Pro His Pro Ala Phe Leu Leu Ile Pro Arg Lys
        35                  40                  45

Val Cys Asn Gly Ile Gly Ile Gly Glu Phe Lys Asp Ser Leu Ser Ile
    50                  55                  60

Asn Ala Thr Asn Ile Lys His Phe Lys Asn Cys Thr Ser Ile Ser Gly
65                  70                  75                  80

Asp Leu His Ile Leu Pro Val Ala Phe Arg Gly Asp Ser Phe Thr His
                85                  90                  95

Thr Pro Pro Leu Asp Pro Gln Glu Leu Asp Ile Leu Lys Thr Val Lys
            100                 105                 110

Glu Ile Thr Gly Phe Leu Leu Ile Gln Ala Trp Pro Glu Asn Arg Thr
        115                 120                 125

Asp Leu His Ala Phe Glu Asn Leu Glu Ile Ile Arg Gly Arg Thr Lys
    130                 135                 140

Gln His Gly Gln Phe Ser Leu Ala Val Val Ser Leu Asn Ile Thr Ser
145                 150                 155                 160

Leu Gly Leu Arg Ser Leu Lys Glu Ile Ser Asp Gly Asp Val Ile Ile
                165                 170                 175

Ser Gly Asn Lys Asn Leu Cys Tyr Ala Asn Thr Ile Asn Trp Lys Lys
            180                 185                 190

Leu Phe Gly Thr Ser Gly Gln Lys Thr Lys Ile Ile Ser Asn Arg Gly
        195                 200                 205

Glu Asn Ser Cys Lys Ala Thr Gly Gln Val Cys His Ala Leu Cys Ser
    210                 215                 220

Pro Glu Gly Cys Trp Gly Pro Glu Pro Arg Asp Cys Val Ser Cys Arg
225                 230                 235                 240

Asn Val Ser Arg Gly Arg Glu Cys Val Asp Lys Cys Asn Leu Leu Glu
                245                 250                 255

Gly Glu Pro Arg Glu Phe Val Glu Asn Ser Glu Cys Ile Gln Cys His
            260                 265                 270

Pro Glu Cys Leu Pro Gln Ala Met Asn Ile Thr Cys Thr Gly Arg Gly
        275                 280                 285

Pro Asp Asn Cys Ile Gln Cys Ala His Tyr Ile Asp Gly Pro His Cys
    290                 295                 300

Val Lys Thr Cys Pro Ala Gly Val Met Gly Glu Asn Asn Thr Leu Val
305                 310                 315                 320

Trp Lys Tyr Ala Asp Ala Gly His Val Cys His Leu Cys His Pro Asn
                325                 330                 335

Cys Thr Tyr Gly Cys Thr Gly Pro Gly Leu Glu Gly Cys Pro Thr Asn
            340                 345                 350
```

```
Gly Pro Lys Ile Pro Ser Ile Ala Thr Gly Met Val Gly Ala Leu Leu
        355                 360                 365

Leu Leu Leu Val Val Ala Leu Gly Ile Gly Leu Phe Met
    370                 375             380
```